United States Patent
Marzano et al.

(10) Patent No.: US 10,080,889 B2
(45) Date of Patent: *Sep. 25, 2018

(54) LOW INDUCTANCE AND LOW RESISTANCE HERMETICALLY SEALED FILTERED FEEDTHROUGH FOR AN AIMD

(71) Applicant: Greatbatch Ltd., Clarence, NY (US)

(72) Inventors: Thomas Marzano, East Amherst, NY (US); Robert A. Stevenson, Canyon Country, CA (US); Christine A. Frysz, Orchard Park, NY (US); Jason Woods, Carson City, NV (US); Richard L. Brendel, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 756 days.

This patent is subject to a terminal disclaimer.

(21) Appl. No.: 14/187,295

(22) Filed: Feb. 23, 2014

(65) Prior Publication Data

US 2014/0168917 A1   Jun. 19, 2014

Related U.S. Application Data

(63) Continuation-in-part of application No. 13/873,832, filed on Apr. 30, 2013, now Pat. No. 8,868,189, (Continued)

(51) Int. Cl.
*A61N 1/375* (2006.01)
*H01G 4/40* (2006.01)
(Continued)

(52) U.S. Cl.
CPC .............. *A61N 1/08* (2013.01); *A61N 1/375* (2013.01); *A61N 1/3718* (2013.01);
(Continued)

(58) Field of Classification Search
CPC ...... A61N 1/3754; A61N 1/3718; A61N 1/05; A61N 1/375; A61N 1/08; A61N 2001/086; H01G 4/35; H03H 1/0007
(Continued)

(56) References Cited

U.S. PATENT DOCUMENTS 3,681,612 A   8/1972   Kinzler et al.
3,745,430 A   7/1973   Kerr et al.
(Continued)

FOREIGN PATENT DOCUMENTS

EP   0243573   11/1987
EP   0145430   5/1991
(Continued)

OTHER PUBLICATIONS

Balanis, "Advanced Engineering Electromagnetics", 1989.
(Continued)

*Primary Examiner* — Christopher D Koharski
*Assistant Examiner* — Pamela M Bays
(74) *Attorney, Agent, or Firm* — Michael F. Scalise; Marc G. Martino

(57) ABSTRACT

A hermetically sealed filtered feedthrough includes a chip capacitor disposed on a circuit board on a device side. A first low impedance electrical connection is between a capacitor first end metallization and a conductor which is disposed through an insulator. A second low impedance electrical connection is between the capacitor second end metallization and a ferrule or housing. The second low impedance electrical connection may include an oxide-resistant electrical connection forming the hermetic seal between the insulator and the ferrule or housing and an electrical connection between and to the second end metallization and directly to the oxide-resistant electrical connection. Alternatively, the second low impedance electrical connection may include an
(Continued)

oxide-resistant metal addition attached directly to the ferrule or housing and an electrical connection between and to the second end metallization and directly to the oxide-resistant metal addition.

42 Claims, 44 Drawing Sheets

Related U.S. Application Data which is a continuation of application No. 13/528,052, filed on Jun. 20, 2012, now Pat. No. 8,433,410, which is a continuation of application No. 12/891,587, filed on Sep. 27, 2010, now Pat. No. 8,483,840, which is a continuation of application No. 12/407,402, filed on Mar. 19, 2009, now Pat. No. 8,195,295, application No. 14/187,295, which is a continuation-in-part of application No. 14/088,849, filed on Nov. 25, 2013, now Pat. No. 8,855,768, which is a continuation of application No. 13/408,020, filed on Feb. 29, 2012, now abandoned.

(60) Provisional application No. 61/841,419, filed on Jun. 30, 2013.

(51) Int. Cl.
*A61N 1/08* (2006.01)
*A61N 1/37* (2006.01)
*H01R 13/7195* (2011.01)
*H03H 1/00* (2006.01)
*H01R 13/52* (2006.01)
*H01G 2/02* (2006.01)
*H01G 2/10* (2006.01)
*H03H 7/01* (2006.01)

(52) U.S. Cl.
CPC .............. *A61N 1/3754* (2013.01); *H01G 2/02* (2013.01); *H01G 2/10* (2013.01); *H01G 4/40* (2013.01); *H01R 13/5224* (2013.01); *H01R 13/7195* (2013.01); *H03H 1/0007* (2013.01); *A61N 1/086* (2017.08); *H01R 2201/12* (2013.01); *H03H 7/1766* (2013.01); *H03H 2001/0042* (2013.01); *H03H 2001/0085* (2013.01)

(58) Field of Classification Search
USPC .................................................... 607/36, 37
See application file for complete search history.

(56) References Cited

U.S. PATENT DOCUMENTS

| | | | |
|---|---|---|---|
| 3,871,382 A | 3/1975 | Mann |
| 3,961,294 A | 6/1976 | Hollyday |
| 3,968,802 A | 7/1976 | Ballis |
| 3,980,975 A | 9/1976 | Maxon et al. |
| 4,188,598 A | 2/1980 | Hunt |
| 4,236,127 A | 11/1980 | Scherba |
| 4,295,467 A | 10/1981 | Mann et al. |
| 4,320,763 A | 3/1982 | Money |
| 4,424,551 A | 1/1984 | Stevenson et al. |
| 4,431,005 A | 2/1984 | McCormick |
| 4,437,474 A | 3/1984 | Peers-Trevarton et al. |
| 4,445,501 A | 5/1984 | Bresler |
| 4,572,198 A | 2/1986 | Codrington |
| 4,585,001 A | 4/1986 | Belt |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,689,621 A | 8/1987 | Kleinberg |
| 4,712,555 A | 12/1987 | Thornander et al. |
| 4,746,864 A | 5/1988 | Satoh et al. |
| 4,754,752 A | 7/1988 | Ginsburg et al. |
| 4,757,820 A | 7/1988 | Itoh |
| 4,766,381 A | 8/1988 | Conturo et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,064 A | 8/1989 | Segawa et al. |
| 4,858,623 A | 8/1989 | Bradshaw et al. |
| 4,859,950 A | 8/1989 | Keren |
| 4,932,411 A | 6/1990 | Fritschy et al. |
| 4,940,052 A | 7/1990 | Mann et al. |
| 4,960,106 A | 10/1990 | Kubokawa et al. |
| 4,977,298 A | 12/1990 | Fujiyama |
| 4,989,608 A | 2/1991 | Ratner |
| 4,991,580 A | 2/1991 | Moore |
| 5,019,075 A | 5/1991 | Spears et al. |
| 5,039,965 A | 8/1991 | Higgins |
| 5,044,375 A | 9/1991 | Bach et al. |
| 5,052,404 A | 10/1991 | Hodgson et al. |
| 5,063,348 A | 11/1991 | Kuhara et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Shturman |
| 5,197,468 A | 3/1993 | Proctor et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,222,506 A | 6/1993 | Patrick et al. |
| 5,246,438 A | 9/1993 | Langberg |
| 5,251,120 A | 10/1993 | Smith |
| 5,268,810 A | 12/1993 | Dimarco et al. |
| 5,271,400 A | 12/1993 | Dumoulin et al. |
| 5,300,108 A | 4/1994 | Rebell et al. |
| 5,306,291 A | 4/1994 | Kroll et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,331,505 A | 7/1994 | Wilheim |
| 5,333,095 A | 7/1994 | Stevenson et al. |
| 5,334,045 A | 8/1994 | Cappa et al. |
| 5,334,193 A | 8/1994 | Nardella |
| 5,348,010 A | 9/1994 | Schnall et al. |
| 5,352,979 A | 10/1994 | Conturo |
| 5,358,515 A | 10/1994 | Hurter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,404,880 A | 4/1995 | Throne |
| 5,413,104 A | 5/1995 | Buijs et al. |
| 5,419,325 A | 5/1995 | Dumoulin et al. |
| 5,428,337 A | 6/1995 | Vinclarelli et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,450,090 A | 9/1995 | Gels et al. |
| 5,451,232 A | 9/1995 | Rhinehart et al. |
| 5,462,055 A | 10/1995 | Casey et al. |
| 5,466,254 A | 11/1995 | Helland |
| 5,476,095 A | 12/1995 | Schnall et al. |
| 5,476,483 A | 12/1995 | Bornzin et al. |
| 5,491,300 A | 2/1996 | Huppenthal et al. |
| 5,493,259 A | 2/1996 | Blalock et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |

(56) References Cited

U.S. PATENT DOCUMENTS

| | | |
|---|---|---|
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,623,724 A | 4/1997 | Gurkovich et al. |
| 5,629,622 A | 5/1997 | Scampini |
| 5,650,759 A | 7/1997 | Hittman et al. |
| 5,662,108 A | 9/1997 | Budd et al. |
| 5,682,897 A | 11/1997 | Pomeranz |
| 5,683,435 A | 11/1997 | Truex et al. |
| 5,685,878 A | 11/1997 | Falwell et al. |
| 5,697,958 A | 12/1997 | Paul et al. |
| 5,699,801 A | 12/1997 | Atalar et al. |
| 5,700,548 A | 12/1997 | Warnier et al. |
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |
| 5,735,884 A | 4/1998 | Thompson et al. |
| 5,735,887 A | 4/1998 | Barreras et al. |
| 5,741,321 A | 4/1998 | Brennen |
| 5,751,539 A | 5/1998 | Stevenson et al. |
| 5,757,252 A | 5/1998 | Cho et al. |
| 5,759,202 A | 6/1998 | Schroeppel |
| 5,765,779 A | 6/1998 | Hancock et al. |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,782,891 A | 7/1998 | Hassler et al. |
| 5,788,980 A | 8/1998 | Nabahi et al. |
| 5,792,055 A | 8/1998 | McKinnon |
| 5,800,467 A | 9/1998 | Park et al. |
| 5,822,174 A | 10/1998 | Yamate et al. |
| 5,824,026 A | 10/1998 | Diaz et al. |
| 5,824,029 A | 10/1998 | Weijand et al. |
| 5,833,608 A | 11/1998 | Acker |
| 5,836,992 A | 11/1998 | Thompson et al. |
| 5,840,031 A | 11/1998 | Crowley |
| 5,851,226 A | 12/1998 | Skubitz et al. |
| 5,855,995 A | 1/1999 | Haq et al. |
| 5,864,234 A | 1/1999 | Luedeke |
| 5,868,674 A | 2/1999 | Glowinski et al. |
| 5,879,347 A | 3/1999 | Saadat |
| 5,891,134 A | 4/1999 | Goble et al. |
| 5,896,267 A | 4/1999 | Hittman et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,929,729 A | 7/1999 | Swarup |
| 5,938,609 A | 8/1999 | Pomeranz |
| 5,938,692 A | 8/1999 | Rudie |
| 5,959,336 A | 9/1999 | Barsan |
| 5,959,829 A | 9/1999 | Stevenson et al. |
| 5,964,705 A | 10/1999 | Truwit et al. |
| 5,973,906 A | 10/1999 | Stevenson et al. |
| 5,973,907 A | 10/1999 | Reed |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,031,710 A | 2/2000 | Wolf et al. |
| 6,041,496 A | 3/2000 | Haq et al. |
| 6,045,532 A | 4/2000 | Eggers et al. |
| 6,052,614 A | 4/2000 | Morris et al. |
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,137,161 A | 10/2000 | Gilliland et al. |
| 6,141,594 A | 10/2000 | Flynn et al. |
| 6,146,743 A | 11/2000 | Haq et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,198,972 B1 | 3/2001 | Hartlaub et al. |
| 6,209,764 B1 | 4/2001 | Hartlaub et al. |
| 6,226,545 B1 | 5/2001 | Gilderdale |
| 6,236,205 B1 | 5/2001 | Lüdeke et al. |
| 6,238,390 B1 | 5/2001 | Tu et al. |
| 6,252,761 B1 | 6/2001 | Branchevsky |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,280,385 B1 | 8/2001 | Melzer et al. |
| 6,284,080 B1 | 9/2001 | Haq et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,373,673 B1 | 4/2002 | Anthony |
| 6,390,996 B1 | 5/2002 | Halperin et al. |
| 6,395,637 B1 | 5/2002 | Park et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,433,653 B1 | 8/2002 | Matsumura et al. |
| 6,456,481 B1 | 9/2002 | Stevenson |
| 6,459,935 B1 | 10/2002 | Piersma |
| 6,470,545 B1 | 10/2002 | Branchevsky |
| 6,473,291 B1 | 10/2002 | Stevenson |
| 6,473,314 B1 | 10/2002 | Custer et al. |
| 6,486,529 B2 | 11/2002 | Chi et al. |
| 6,493,591 B1 | 12/2002 | Stokes |
| 6,512,666 B1 | 1/2003 | Duva |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Dal Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,615,483 B2 | 9/2003 | Lindegren |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,660,116 B2 | 12/2003 | Wolf |
| 6,675,033 B1 | 1/2004 | Lardo et al. |
| 6,675,036 B2 | 1/2004 | Kreger et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,694,583 B2 | 2/2004 | Branchevsky |
| 6,697,675 B1 | 2/2004 | Safarevich et al. |
| 6,701,176 B1 | 3/2004 | Halperin et al. |
| 6,714,809 B2 | 3/2004 | Lee et al. |
| 6,728,575 B2 | 4/2004 | Hedberg |
| 6,728,579 B1 | 4/2004 | Lindgren et al. |
| 6,759,388 B1 | 7/2004 | Marchant et al. |
| 6,765,779 B2 | 7/2004 | Stevenson |
| 6,765,780 B2 | 7/2004 | Brendel et al. |
| 6,768,630 B2 | 7/2004 | Togashi |
| 6,771,067 B2 | 8/2004 | Kellman et al. |
| 6,795,730 B2 | 9/2004 | Connelly et al. |
| 6,806,806 B2 | 10/2004 | Anthony |
| 6,823,215 B2 | 11/2004 | Obel et al. |
| 6,829,509 B1 | 12/2004 | MacDonald et al. |

(56) References Cited

U.S. PATENT DOCUMENTS

| | | |
|---|---|---|
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,930,242 B1 | 8/2005 | Helfer et al. |
| 6,931,283 B1 | 8/2005 | Magnusson |
| 6,931,286 B2 | 8/2005 | Sigg et al. |
| 6,934,588 B1 | 8/2005 | Brand et al. |
| 6,944,489 B2 | 9/2005 | Zeijlemaker et al. |
| 6,944,507 B2 | 9/2005 | Fröberg et al. |
| 6,949,929 B2 | 9/2005 | Gray et al. |
| 6,950,696 B2 | 9/2005 | Björling et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,999,818 B2 | 2/2006 | Stevenson et al. |
| 7,012,192 B2 | 3/2006 | Stevenson et al. |
| 7,013,180 B2 | 3/2006 | Dougherty et al. |
| 7,015,393 B2 | 3/2006 | Weiner et al. |
| 7,038,900 B2 | 5/2006 | Stevenson et al. |
| 7,039,455 B1 | 5/2006 | Brosovich et al. |
| 7,046,499 B1 | 5/2006 | Imani et al. |
| 7,047,073 B2 | 5/2006 | Höijer et al. |
| 7,050,855 B2 | 5/2006 | Zeijlemaker et al. |
| 7,068,491 B1 | 6/2006 | Burdon et al. |
| 7,091,412 B2 | 8/2006 | Wang et al. |
| 7,092,766 B1 | 8/2006 | Salys et al. |
| 7,110,227 B2 | 9/2006 | Anthony et al. |
| 7,113,387 B2 | 9/2006 | Stevenson et al. |
| 7,123,013 B2 | 10/2006 | Gray |
| 7,127,294 B1 | 10/2006 | Wang et al. |
| 7,148,783 B2 | 12/2006 | Parsche et al. |
| 7,149,578 B2 | 12/2006 | Edvardsson |
| 7,149,773 B2 | 12/2006 | Haller et al. |
| 7,155,271 B2 | 12/2006 | Halperin et al. |
| 7,162,302 B2 | 1/2007 | Wang et al. |
| 7,164,572 B1 | 1/2007 | Burdon et al. |
| 7,164,950 B2 | 1/2007 | Kroll et al. |
| 7,174,219 B2 | 2/2007 | Wahlstrand et al. |
| 7,199,995 B2 | 4/2007 | Stevenson |
| 7,236,816 B2 | 6/2007 | Kumar et al. |
| 7,236,834 B2 | 6/2007 | Christopherson et al. |
| 7,276,474 B2 | 10/2007 | Marchant et al. |
| 7,301,748 B2 | 11/2007 | Anthony et al. |
| 7,310,216 B2 | 12/2007 | Stevenson et al. |
| 7,319,905 B1 | 1/2008 | Morgan et al. |
| 7,322,832 B2 | 1/2008 | Kronich et al. |
| 7,327,553 B2 | 2/2008 | Brendel |
| 7,363,090 B2 | 4/2008 | Halperin et al. |
| 7,369,898 B1 | 5/2008 | Kroll et al. |
| 7,387,928 B2 | 6/2008 | Cheung |
| 7,388,378 B2 | 6/2008 | Gray et al. |
| 7,422,568 B2 | 9/2008 | Yang et al. |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,480,988 B2 | 1/2009 | Ok et al. |
| 7,495,884 B2 | 2/2009 | Togashi |
| 7,517,769 B2 | 4/2009 | Van Schuylenbergh et al. |
| 7,529,590 B2 | 5/2009 | MacDonald |
| 7,561,906 B2 | 7/2009 | Atalar et al. |
| 7,586,728 B2 | 9/2009 | Anthony |
| 7,593,208 B2 | 9/2009 | Anthony et al. |
| 7,675,729 B2 | 3/2010 | Anthony et al. |
| 7,679,926 B2 | 3/2010 | Hsu et al. |
| 7,689,288 B2 | 3/2010 | Stevenson et al. |
| 7,693,576 B1 | 4/2010 | Lavie et al. |
| 7,702,387 B2 | 4/2010 | Stevenson et al. |
| 7,719,854 B2 | 5/2010 | Youker et al. |
| 7,729,770 B2 | 6/2010 | Cabelka et al. |
| 7,733,621 B2 | 6/2010 | Anthony et al. |
| 7,812,691 B1 | 10/2010 | Fisk et al. |
| 7,839,146 B2 | 11/2010 | Gray |
| 7,844,319 B2 | 11/2010 | Susil et al. |
| 7,844,343 B2 | 11/2010 | Wahlstrand et al. |
| 7,853,324 B2 | 12/2010 | Stevenson et al. |
| 7,899,551 B2 | 3/2011 | Westlund et al. |
| 7,901,761 B1 | 3/2011 | Jiang et al. |
| 7,957,806 B2 | 6/2011 | Stevenson et al. |
| 7,989,080 B2 | 8/2011 | Greenberg et al. |
| 8,000,804 B1 | 8/2011 | Wessendorf et al. |
| 8,043,454 B1 | 10/2011 | Jiang et al. |
| 8,095,224 B2 | 1/2012 | Truex et al. |
| 8,163,397 B2 | 4/2012 | Ok et al. |
| 8,219,208 B2 | 7/2012 | Stevenson et al. |
| 8,301,249 B2 | 10/2012 | Min |
| 8,763,245 B1 | 7/2014 | Lucisano et al. |
| 9,014,808 B2 * | 4/2015 | Stevenson ............ A61N 1/3718 361/302 |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0013928 A1 | 1/2003 | Saruwatari |
| 2003/0013948 A1 | 1/2003 | Russell |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0053284 A1 | 3/2003 | Stevenson et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0171792 A1 | 9/2003 | Zarinetchi et al. |
| 2003/0179536 A1 | 9/2003 | Stevenson et al. |
| 2003/0204217 A1 | 10/2003 | Greatbatch |
| 2003/0208252 A1 | 11/2003 | O'Boyle et al. |
| 2003/0212373 A1 | 11/2003 | Hall et al. |
| 2003/0213605 A1 | 11/2003 | Brendel et al. |
| 2004/0015079 A1 | 1/2004 | Berger et al. |
| 2004/0034338 A1 | 2/2004 | Thierfelder et al. |
| 2004/0088012 A1 | 5/2004 | Kroll et al. |
| 2004/0167392 A1 | 8/2004 | Halperin et al. |
| 2004/0210289 A1 | 10/2004 | Wang et al. |
| 2004/0230271 A1 | 11/2004 | Wang et al. |
| 2004/0249428 A1 | 12/2004 | Wang et al. |
| 2004/0263173 A1 | 12/2004 | Gray |
| 2004/0263174 A1 | 12/2004 | Gray et al. |
| 2005/0007718 A1 | 1/2005 | Stevenson et al. |
| 2005/0070972 A1 | 3/2005 | Wahlstrand et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0197677 A1 | 9/2005 | Stevenson |
| 2005/0201039 A1 | 9/2005 | Stevenson et al. |
| 2005/0215914 A1 | 9/2005 | Bornzin et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0248340 A1 | 11/2005 | Berkcan et al. |

(56) References Cited

U.S. PATENT DOCUMENTS

| | | |
|---|---|---|
| 2005/0248907 A1 | 11/2005 | Stevenson et al. |
| 2006/0009819 A1 | 1/2006 | Przybyszewski |
| 2006/0025820 A1 | 2/2006 | Phillips et al. |
| 2006/0030774 A1 | 2/2006 | Gray et al. |
| 2006/0032665 A1 | 2/2006 | Ice |
| 2006/0041294 A1 | 2/2006 | Gray |
| 2006/0085043 A1 | 4/2006 | Stevenson |
| 2006/0100506 A1 | 5/2006 | Halperin et al. |
| 2006/0119361 A1 | 6/2006 | Karmarkar et al. |
| 2006/0200218 A1 | 9/2006 | Wahlstrand |
| 2006/0211979 A1 | 9/2006 | Smith et al. |
| 2006/0212096 A1 | 9/2006 | Stevenson |
| 2006/0221543 A1 | 10/2006 | Stevenson et al. |
| 2006/0229693 A1 | 10/2006 | Bauer et al. |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0259093 A1 | 11/2006 | Stevenson et al. |
| 2006/0271138 A1 | 11/2006 | MacDonald |
| 2007/0035910 A1 | 2/2007 | Stevenson |
| 2007/0043399 A1 | 2/2007 | Stevenson et al. |
| 2007/0083244 A1 | 4/2007 | Stevenson et al. |
| 2007/0088416 A1 | 4/2007 | Atalar et al. |
| 2007/0093142 A1 | 4/2007 | MacDonald et al. |
| 2007/0106332 A1 | 5/2007 | Denker et al. |
| 2007/0112398 A1 | 5/2007 | Stevenson et al. |
| 2007/0123949 A1 | 5/2007 | Dabney et al. |
| 2007/0167867 A1 | 7/2007 | Wolf |
| 2007/0168005 A1 | 7/2007 | Gray |
| 2007/0168006 A1 | 7/2007 | Gray |
| 2007/0179554 A1 | 8/2007 | Lyer et al. |
| 2007/0179577 A1 | 8/2007 | Marshall et al. |
| 2007/0203529 A1 | 8/2007 | Iyer et al. |
| 2007/0208383 A1 | 9/2007 | Williams |
| 2007/0250743 A1 | 10/2007 | Matsubara et al. |
| 2007/0255332 A1 | 11/2007 | Cabelka et al. |
| 2007/0255377 A1 | 11/2007 | Marshall et al. |
| 2007/0288058 A1 | 12/2007 | Halperin et al. |
| 2007/0299490 A1 | 12/2007 | Yang et al. |
| 2008/0004670 A1 | 1/2008 | McVenes et al. |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0049410 A1 | 2/2008 | Kawaguchi et al. |
| 2008/0051854 A1 | 2/2008 | Bulkes et al. |
| 2008/0071313 A1 | 3/2008 | Stevenson et al. |
| 2008/0116997 A1 | 5/2008 | Dabney et al. |
| 2008/0132986 A1 | 6/2008 | Gray et al. |
| 2008/0132987 A1 | 6/2008 | Westlund et al. |
| 2008/0140149 A1 | 6/2008 | John et al. |
| 2008/0158746 A1 | 7/2008 | Anthony et al. |
| 2008/0161886 A1 | 7/2008 | Stevenson et al. |
| 2008/0195180 A1 | 8/2008 | Stevenson et al. |
| 2008/0195186 A1 | 8/2008 | Li et al. |
| 2008/0195187 A1 | 8/2008 | Li et al. |
| 2008/0221638 A1 | 9/2008 | Wedan et al. |
| 2008/0239622 A1 | 10/2008 | Hsu et al. |
| 2008/0243218 A1 | 10/2008 | Bottomley et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0262584 A1 | 10/2008 | Bottomley et al. |
| 2008/0262592 A1 | 10/2008 | Jordan et al. |
| 2008/0264685 A1 | 10/2008 | Park et al. |
| 2008/0269591 A1 | 10/2008 | Halperin et al. |
| 2008/0277153 A1 | 11/2008 | Teshome et al. |
| 2009/0036944 A1 | 2/2009 | Fonte |
| 2009/0097219 A1 | 4/2009 | Cho et al. |
| 2009/0099440 A1 | 4/2009 | Viohl |
| 2009/0099555 A1 | 4/2009 | Viohl et al. |
| 2009/0107717 A1 | 4/2009 | Hsu et al. |
| 2009/0116167 A1 | 5/2009 | Stevenson et al. |
| 2009/0128976 A1 | 5/2009 | Anthony |
| 2009/0139760 A1 | 6/2009 | Tanaka |
| 2009/0163980 A1 | 6/2009 | Stevenson |
| 2009/0180237 A1 | 7/2009 | Hou et al. |
| 2009/0187229 A1 | 7/2009 | Lavie |
| 2009/0236141 A1 | 9/2009 | Kim et al. |
| 2009/0243756 A1 | 10/2009 | Stevenson et al. |
| 2009/0270948 A1 | 10/2009 | Nghiem et al. |
| 2009/0281592 A1 | 11/2009 | Vase |
| 2009/0312835 A1 | 12/2009 | Stevenson |
| 2010/0010602 A1 | 1/2010 | Wedan et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0046135 A1 | 2/2010 | Niki et al. |
| 2010/0046137 A1 | 2/2010 | Adachi |
| 2010/0076538 A1 | 3/2010 | Desai et al. |
| 2010/0109958 A1 | 5/2010 | Haubrich et al. |
| 2010/0109966 A1 | 5/2010 | Mateychuk et al. |
| 2010/0114276 A1 | 5/2010 | Min et al. |
| 2010/0114277 A1 | 5/2010 | Zhao et al. |
| 2010/0138192 A1 | 6/2010 | Min |
| 2010/0149042 A1 | 6/2010 | Utsi et al. |
| 2010/0151113 A1 | 6/2010 | Shelton |
| 2010/0160989 A1 | 6/2010 | Legay |
| 2010/0174348 A1 | 7/2010 | Bulkes et al. |
| 2010/0174349 A1 | 7/2010 | Stevenson et al. |
| 2010/0198312 A1 | 8/2010 | Stevenson et al. |
| 2010/0217262 A1 | 8/2010 | Stevenson et al. |
| 2010/0217264 A1 | 8/2010 | Odom et al. |
| 2010/0217341 A1 | 8/2010 | John et al. |
| 2010/0234907 A1 | 9/2010 | Dobak |
| 2011/0043297 A1 | 2/2011 | Stevenson et al. |

FOREIGN PATENT DOCUMENTS

| | | |
|---|---|---|
| EP | 0466424 | 1/1992 |
| EP | 0557127 | 8/1993 |
| EP | 0673621 | 9/1995 |
| EP | 0498996 | 3/1997 |
| EP | 1021730 | 4/2003 |
| EP | 0930509 | 3/2004 |
| EP | 1469910 | 12/2006 |
| EP | 1883449 | 1/2009 |
| EP | 2025361 | 2/2009 |
| JP | 60141034 | 7/1985 |
| JP | 61181925 | 8/1986 |
| JP | 62233905 | 10/1987 |
| JP | 4071536 | 3/1992 |
| JP | 6054823 | 3/1994 |
| JP | 06070902 | 3/1994 |
| JP | 6176962 | 6/1994 |
| JP | 7272975 | 10/1995 |
| JP | 9094238 | 4/1997 |
| JP | 11239572 | 9/1999 |
| JP | 2004254257 | 9/2004 |
| JP | 2004289760 | 10/2004 |
| JP | 2005117606 | 4/2005 |
| JP | 2007129565 | 5/2007 |
| WO | 8704080 | 7/1987 |
| WO | 9210213 | 6/1992 |
| WO | 9423782 | 10/1994 |
| WO | 9740396 | 10/1997 |
| WO | 9852461 | 11/1998 |
| WO | 9919739 | 4/1999 |
| WO | 0010456 | 3/2000 |
| WO | 0025672 | 5/2000 |
| WO | 02083016 | 10/2002 |
| WO | 2003037424 | 5/2003 |
| WO | 2003063946 | 8/2003 |
| WO | 2003063952 | 8/2003 |
| WO | 2003063953 | 8/2003 |
| WO | 2003063955 | 8/2003 |
| WO | 2003063956 | 8/2003 |
| WO | 2003063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |

(56) References Cited

FOREIGN PATENT DOCUMENTS

| WO | 2007047966 | 4/2007 |
|---|---|---|
| WO | 2007089988 | 8/2007 |
| WO | 2007102893 | 9/2007 |
| WO | 2007145671 | 12/2007 |
| WO | 2008077037 | 6/2008 |
| WO | 2008111986 | 9/2008 |
| WO | 2010008833 | 1/2010 |

OTHER PUBLICATIONS

Clement, et al., "Estimation of Effective Lead Loop Area for Implantable Pulse Generators and Cardioverter/Defibrillators for Determination of Susceptibility to Radiated Electromagnetic Interference", AAMI EMC Task Force, Apr. 12, 2004, 10 pages.

Ennis, et al., "Cautions About the Use of Equivalent Series Resistance (ESR) in Specifying Capacitors", Mar. 8, 1993, 58-64.

EPSEARCH, "10167031.3", Sep. 19, 2012, Sep. 19, 2012.

EPSEARCH, "10167045.3", Oct. 10, 2012, Oct. 10, 2012.

Gabriel, et al., "Dielectric Properties of Biological Tissues: Literature Survey", 1996.

Gabriel, et al., "Dielectric Properties of Biological Tissues: Measurements and the Frequency Range 0 Hz to 20 GHz", Phys. Med. Biol. 41, 1996, 1996, 2251-2269.

Gabriel, et al., "The Dielectric Properties of Biological Tissues: Parametric Models for the Dielectric Spectrum of Tissues", Parametric Models for the Dielectric Spectrum of Tissues Phys. Med. Bio. 41, 1996, 2271-2293.

Johnson, et al., "Characterization of the Relationship between MR-Induced Distal Tip Heating in Cardiac Pacing Leads and Electrical Performance of Novel Filtered Tip Assemblies", 17th Scientific Meeting & Exhibition of the International Society for Magnetic Resonance in Medicine, Honolulu, Hawaii, Apr. 2009, 307.

Konings, et al., "Heating Around Intravascular Guidewires by Resonating RF Waves", Journal of Magnetic Resonance Imaging, 2000, 79-85.

Luchinger, "Safety Aspects of Cardiac Pacemakers in Magnetic Resonance Imaging", A dissertation submitted to the Swiss Federal Institute of Technology Zurich, Switzerland, 2002, 2002.

Luchinger, "Safety Aspects of Cardiac Pacemakers in Magnetic Resonance Imaging", A dissertation submitted to the Swiss Federal Institute of Technology Zurich., 2002.

Roguin, et al., "Modern Pacemaker and Implantable Cardioverter/ Defibrillator systems Can Be Magnetic Resonance Imaging Safe", Journal of the American Heart Association, Aug. 4, 2004, 475-482.

Search, "European Search Report for EP12157697.9", dated Jul. 5, 2012.

Shellock, et al., "Comparative Analyses of MR-Induced Distal Heating in Novel Filtered Cardiac Pacing Leads UsingTwo Geometric Configurations", 17th Scientific Meeting & Exhibition of the International Society for Magnetic Resonance in Medicine, Honolulu, Hawaii, Apr. 2009, 3014.

Shellock, "MRI Issues for Neuromodulation Devices", Institute for Magnetic Resonance Safety Education, and Research (IMRSER).

Susil, et al., "Multifunctional Interventional Devices for MRI: A Combined Electrophysiology/MRI Catheter", 2002, 594-600.

Susil, et al., "U.S. Appl. No. 60/283,725", Multifunctional Interventional Devices for Use in MRI, Apr. 13, 2001.

Weiner, et al., "U.S. Appl. No. 60/269,817", Electromagnetic Interference immune Cardiac Assist System, Feb. 20, 2001.

Wilk, et al., "High-K Gate Dielectrics: Current Status and Materials Properties Considerations", Journal of Applied Physi s, vol. 89, No. 10, May 15, 2001, 5243-5275.

* cited by examiner

FIG. 12  $f_r = \dfrac{1}{2\pi\sqrt{LC}}$  Where $f_r$ = resonance frequency
$L$ = Inductance
$C$ = Capacitance

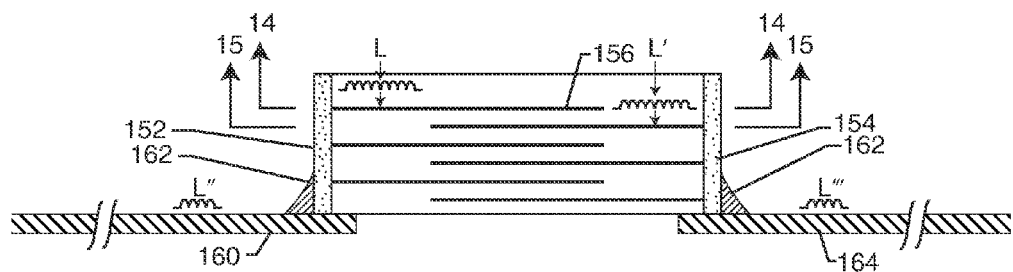
FIG. 13
PRIOR ART
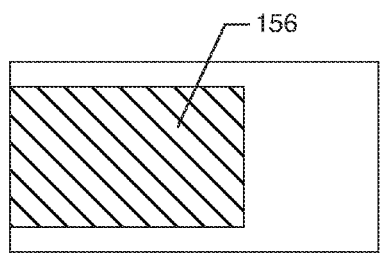 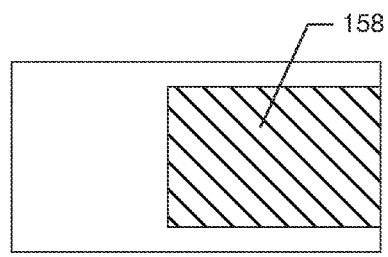
FIG. 14
PRIOR ART
FIG. 15
PRIOR ART

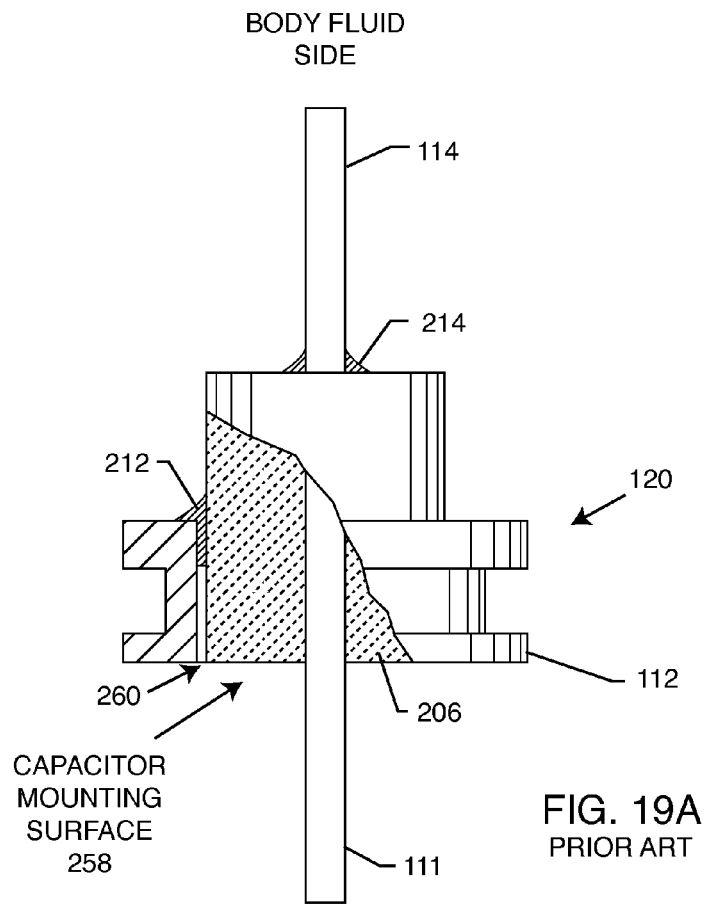
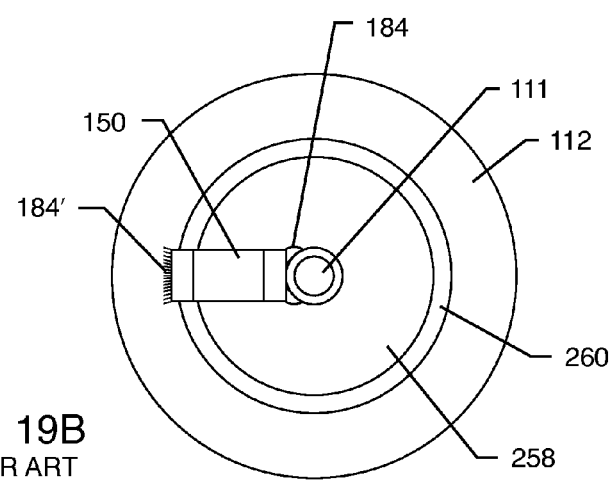

EMI HIGH FREQUENCY MODEL

LOW FREQUENCY MODEL

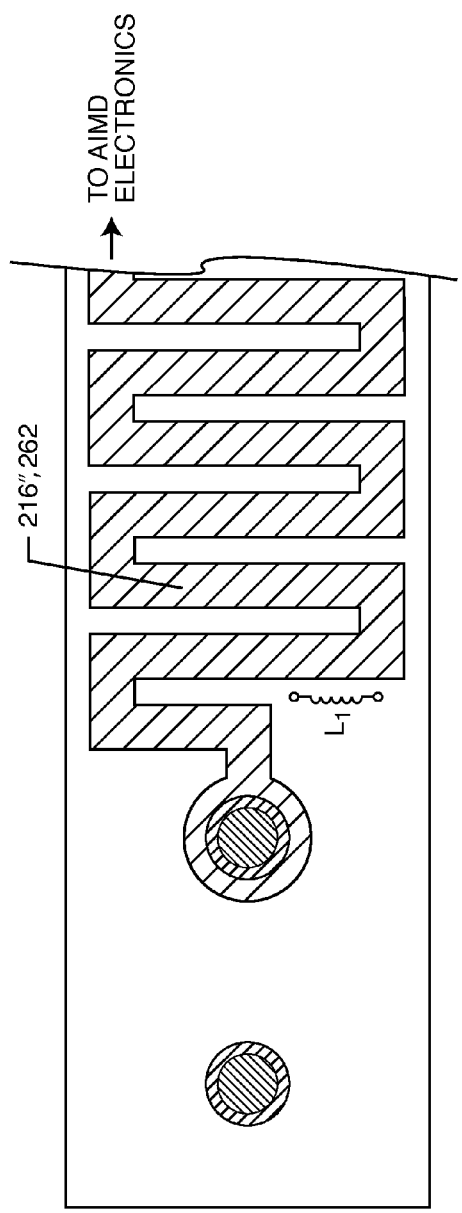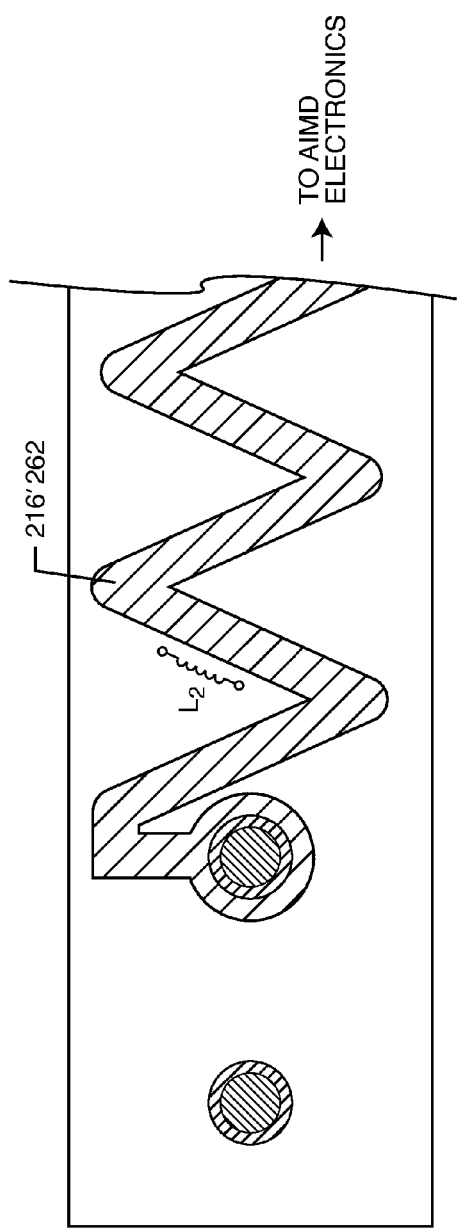

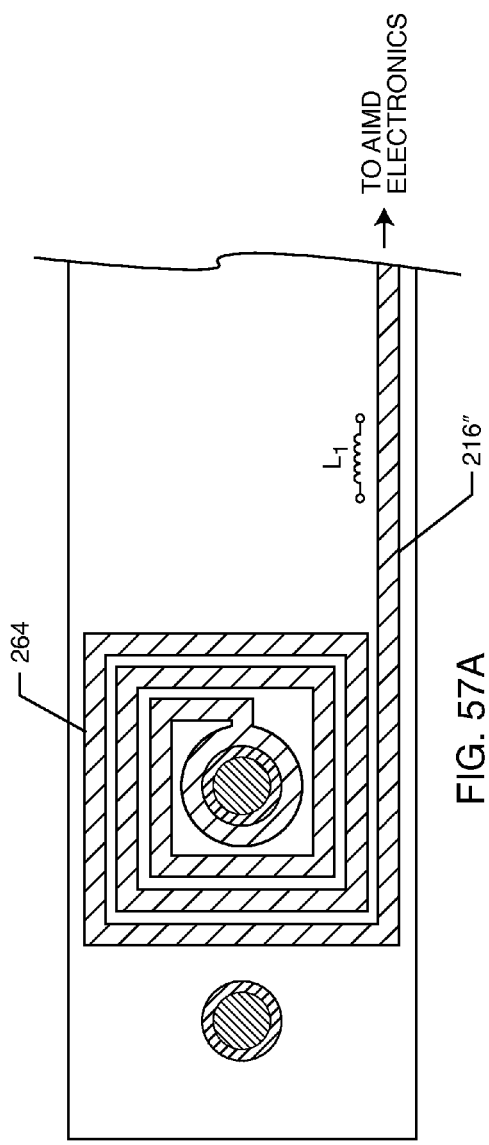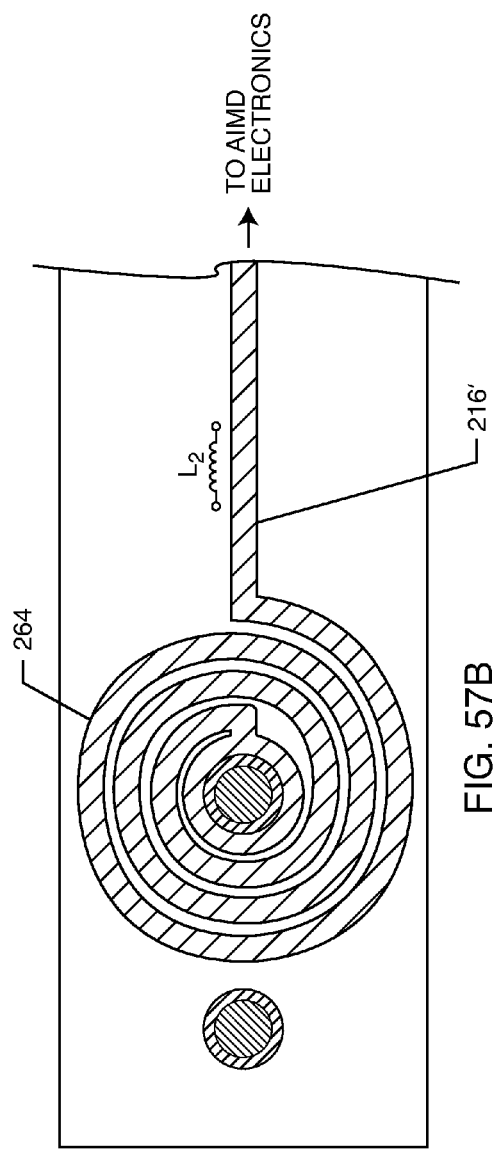

LOW INDUCTANCE AND LOW RESISTANCE HERMETICALLY SEALED FILTERED FEEDTHROUGH FOR AN AIMD

CROSS-REFERENCE TO RELATED APPLICATIONS

The present application claims priority to provisional application Ser. No. 61/841,419, filed on Jun. 30, 2013. The present application also claims priority to and is a continuation-in-part application to both U.S. application Ser. No. 13/873,832, filed on Apr. 30, 2013 and U.S. application Ser. No. 14/088,849, filed on Nov. 25, 2013, now U.S. Pat. No. 8,855,768. The present application is also a continuation of U.S. application Ser. No. 13/528,052, filed on Jun. 20, 2012, now U.S. Pat. No. 8,433,410, issued on Apr. 30, 2013, which is a continuation of U.S. application Ser. No. 13/408,020, filed on Feb. 29, 2012, now abandoned, which is a continuation of U.S. application Ser. No. 12/891,587, filed on Sep. 27, 2010, now U.S. Pat. No. 8,483,840, issued on Jul. 9, 2013, which is a continuation of U.S. application Ser. No. 12/407,402, filed on Mar. 19, 2009, now U.S. Pat. No. 8,195,295, issued on Jun. 5, 2012; the contents of which all applications are fully incorporated herein with these references.

FIELD OF THE INVENTION

The present invention generally relates to filtered feedthroughs for active implantable medical devices. More particularly, the present invention relates to a low inductance and low resistance hermetically sealed filtered feedthrough utilizing chip capacitors.

BACKGROUND OF THE INVENTION

Compatibility of cardiac pacemakers, implantable defibrillators and other types of active implantable medical devices with magnetic resonance imaging (MRI) and other types of hospital diagnostic equipment has become a major issue. If one proceeds to the websites of the major cardiac pacemaker manufacturers in the United States, which include St. Jude Medical, Medtronic and Boston Scientific (formerly Guidant), one will see that the use of MRI is generally contra-indicated for patients with implanted pacemakers and cardioverter defibrillators. See also recent press announcements of the Medtronic Revo MRI pacemaker which was recently approved by the U.S. FDA. With certain technical limitations as to scan type and location, this was the first pacemaker designed for MRI scanning.

However, an extensive review of the literature indicates that, despite being contra-indicated, MRI is indeed often used to image patients with pacemaker, neurostimulator and other active implantable medical devices (AIMDs). As such, the safety and feasibility of MRI in patients with cardiac pacemakers is an issue increasing in significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF pulsed field (Specific Absorption Rate—SAR level), programming the pacemaker to fixed or asynchronous pacing mode, and careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. This suggests that SAR level alone is not a good predictor of whether or not an implanted device or its associated lead system will overheat.

There are three types of electromagnetic fields used in an MRI unit. The first type is the main static magnetic field designated Bo which is used to align protons in body tissue. The field strength varies from 0.5 to 3.0 Tesla in most of the currently available MRI units in clinical use. Some of the newer MRI system fields can go as high as 4 to 5 Tesla. At the International Society for Magnetic Resonance in Medicine (ISMRM), which was held on 5-6 Nov. 2005, it was reported that certain research systems are going up as high as 11.7 Tesla. This is over 100,000 times the magnetic field strength of the earth. A static magnetic field can induce powerful mechanical forces and torque on any magnetic materials implanted within the patient. This would include certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of about 21 MHz to about 500 MHz depending upon the static magnetic field strength. The frequency of the RF pulse for hydrogen scans varies by the Lamour equation with the field strength of the main static field where: RF PULSED FREQUENCY in MHz=(42.56) (STATIC FIELD STRENGTH IN TESLA). There are also phosphorous and other types of scanners wherein the Lamour equation would be different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 2-5 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted lead system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted lead systems actually act as antennas where voltages (EMFs) are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the leadwire system (for example, at the header block of a cardiac pacemaker). This has to do with the wavelength of the signals involved and where they couple efficiently into the system.

Magnetic field coupling into an implanted lead system is based on loop areas. For example, in a cardiac pacemaker unipolar lead, there is a loop formed by the lead as it comes from the cardiac pacemaker housing to its distal tip electrode located in the right ventricle. The return path is through body fluid and tissue generally straight from the tip electrode in the right ventricle back to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal pacemaker implant, the implanted loop area is much larger (around 400 square centimeters).

Relating now to the specific case of MRI, the magnetic gradient fields would be induced through enclosed loop areas. However, the pulsed RF fields, which are generated by the body coil, would be primarily induced into the lead system by antenna action. Subjected to RF frequencies, the lead itself can exhibit complex transmission line behavior.

At the frequencies of interest in MRI, RF energy can be absorbed and converted to heat. The power deposited by RF pulses during MRI is complex and is dependent upon the power (or SAR Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur. Also, distal tip design is very important as it can heat up due to MRI RF induced energy.

The cause of heating in an MRI environment is twofold: (a) RF field coupling to the lead can occur which induces significant local heating; and (b) currents induced between the distal tip and tissue during MRI RF pulse transmission sequences can cause local Ohms Law (resistive) heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD lead geometries. There can also be localized heating problems associated with various types of electrodes in addition to tip electrodes. This includes ring electrodes or pad electrodes. Ring electrodes are commonly used with a wide variety of implanted devices including cardiac pacemakers, and neurostimulators, and the like. Pad electrodes are very common in neurostimulator applications and for cuff electrodes for vagal nerve stimulation. For example, spinal cord stimulators or deep brain stimulators can include a plurality of pad electrodes to make contact with nerve tissue. A good example of this also occurs in a cochlear implant. In a typical cochlear implant there would be sixteen pad electrodes placed up into the cochlea. Several of these pad electrodes make contact with auditory nerves.

Although there are a number of studies that have shown that MRI patients with active implantable medical devices, such as cardiac pacemakers, can be at risk for potential hazardous effects, there are a number of reports in the literature that MRI can be safe for imaging of pacemaker patients when a number of precautions are taken (only when an MRI is thought to be an absolute diagnostic necessity). While these anecdotal reports are of interest, they are certainly not scientifically convincing that all MRI can be safe. For example, just variations in the pacemaker lead length and implant trajectory can significantly affect how much heat is generated. A paper entitled, HEATING AROUND INTRAVASCULAR GUIDEWIRES BY RESONATING RF WAVES by Konings, et al., Journal of Magnetic Resonance Imaging, Issue 12:79-85 (2000), does an excellent job of explaining how the RF fields from MRI scanners can couple into implanted leads. The paper includes both a theoretical approach and actual temperature measurements. In worst-case, they measured temperature rises of up to 74 degrees C. after 30 seconds of scanning exposure. The contents of this paper are incorporated herein by reference.

The effect of an MRI system on the function of pacemakers, ICDs, neurostimulators and the like, depends on various factors, including the strength of the static magnetic field, the pulse sequence, the strength of RF field, the anatomic region being imaged, among many others. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring)

electrodes. This can lead to overheating of body tissue at, near or adjacent to the distal tip.

Distal tip electrodes can be unipolar, bipolar and the like. It is very important that excessive current not flow at the interface between the lead distal tip electrode and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. Excessive current at the distal electrode to tissue interface can cause excessive heating to the point where tissue ablation or even perforation can occur. This can be life threatening for cardiac patients. For neurostimulator patients, such as deep brain stimulator patients, thermal injury can cause coma, permanent disability or even be life threatening. Similar issues exist for spinal cord stimulator patients, cochlear implant patients and the like.

Interestingly, the inventors performed an experiment in an MRI scanner with a human body gel-filled phantom. In the phantom and placed in an anatomic position, was an operating pacemaker and a lead. This was during evaluation of the efficacy of bandstop filters at or near the distal tip electrode for preventing the distal tip electrode from overheating. Bandstop filters for this purpose are more thoroughly described in U.S. Pat. No. 7,363,090, the contents of which are incorporated herein by reference. During the experiments, there was a control lead that had no bandstop filter. During a particularly RF intense scanning sequence, Luxtron probes measured a distal helix tip electrode temperature rise of 30 degrees C. Of course, the 30 degrees C. temperature rise in a patient, would be very alarming as it could lead to pacing capture threshold changes or even complete loss capture due to scar tissue formation. An identical lead with the bandstop filter in place only had a temperature rise of 3 degrees C. This validation of the efficacy of bandstop filters for implantable electrodes was of notable significance. However, it was discovered that something very interesting happened when the pacemaker was disconnected. When the pacemaker was disconnected, a silicone lead cap was placed over the proximal end of the lead, and then the gel phantom with capped disconnected lead was placed back inside the MR scanner. This time an 11 degree C. temperature rise on the capped lead with the bandstop filter was measured. This was proof positive that the housing of the AIMD acts as part of the system. The prior art feedthrough capacitor created a fairly low impedance at the input to the pacemaker and thereby drew RF energy out of the lead and diverted it to the housing of the pacemaker. It has recently been discovered that the impedance, and in particular, the ESR of these capacitors, is very important so that maximal energy can be pulled from the lead and diverted to the pacemaker housing while at the same time, not unduly overheating the feedthrough capacitor.

Accordingly, there is a need for novel low ESR diverting capacitors and circuits which are frequency selective and are constructed of passive components for implantable leads and/or leadwires. Further, there is a need for very low ESR diverter element capacitor(s) which are designed to decouple a maximum amount of induced RF energy from an implanted lead to an AIMD housing while at the same time not overheat. The present invention fulfills these needs and provides other related advantages.

SUMMARY OF THE INVENTION

An exemplary embodiment of the present invention includes a hermetically sealed filtered feedthrough for an implantable medical device having an insulator hermetically sealed to a conductive ferrule or housing. A conductor is hermetically sealed and disposed through the insulator in non-conductive relation to the ferrule or housing between a body fluid side and a device side. A two-terminal chip capacitor is disposed on a circuit board located on the device side. The two-terminal chip capacitor has a first and a second end metallization, wherein the first end metallization is connected to at least one active electrode plate and wherein the second end metallization is connected to at least one ground electrode plate, wherein the at least one active electrode plate is interleaved and disposed parallel to the at least one ground electrode plate. The at least one active and ground electrode plates are disposed within a capacitor dielectric. A first low impedance electrical connection is between the first end metallization and the conductor. A second low impedance electrical connection is between the second end metallization and the ferrule or housing. The second low impedance electrical connection includes either (a) an oxide-resistant electrical connection forming the hermetic seal between the insulator and the ferrule or housing and an electrical connection coupling the second end metallization electrically and physically directly to the oxide-resistant electrical connection, or, (b) an oxide-resistant metal addition attached directly to the ferrule or housing and an electrical connection coupling the second end metallization electrically and physically directly to the oxide-resistant metal addition.

In other exemplary embodiments, the oxide-resistant electrical connection may be a noble metal. The oxide-resistant electrical connection may be a pure gold or a gold based braze, a platinum or platinum based braze, a palladium or palladium based braze, or a silver or silver based braze. Non-limiting noble metal based braze examples are gold-palladium, gold-boron, and palladium-silver. It is anticipated that proprietary brazes such as but not limited to the Pallabraze product family (palladium-containing) and Orobraze product family (gold-containing) offered by Johnson Matthey may be used. The braze material may be a rod, a ribbon, a powder, a paste, a cream, a wire and a preform such as but not limited to stamped washers. The oxide-resistant metal addition may be a different material as compared to the ferrule or housing. The oxide-resistant metal addition may be a noble metal. The oxide-resistant metal addition may be gold, platinum, palladium or silver, or combinations thereof. The oxide-resistant metal addition may be laser welded to the ferrule or housing. The oxide-resistant metal addition may be a brazed metal. The brazed metal oxide-resistant metal addition may be gold, gold based, palladium, palladium based, platinum, platinum based, silver or silver based.

A grounding loop may be defined on the device side including the first low impedance electrical connection and the second low impedance connection from the conductor through the two-terminal chip capacitor to the ferrule or housing. The total resistance of the grounding loop may be less than 1 milliohm. The total inductance of the grounding loop may be less than 10 nanohenries or less than 1 nanohenry.

The two-terminal chip capacitor may be a monolithic ceramic chip capacitor, a stacked film capacitor, a tantalum chip capacitor, an electrolytic chip capacitor or a reverse geometry two-terminal chip capacitor.

A circuit board may be disposed adjacent to the insulator. The circuit board may include a flexible portion. At least one nonconductive adhesive washer or epoxy may be disposed between the circuit board and the ferrule or housing or insulator. The circuit board may also have other filter circuits consisting of surface mounted chip capacitors or embedded chip capacitors, surface mounted inductors, embedded inductors or the like. Even solenoid or toroidal inductors could be mounted on the circuit board. The resulting filters could be low pass filters, bandstop filters or L-C trap filters. The circuit board could also contain hybrid electronic circuit chips, protection diodes or other type of protection circuits or even RFID circuits for identification of the AIMD or AIMD particular properties. In a particular application, the circuit board may be attached to a feedthrough capacitor and the circuit board itself may have an inductor in parallel with a capacitor in series with a circuit extending to a distal electrode attachable to human tissues. After the feedthrough capacitor, for example, one could place a bandstop filter consisting of an inductance in parallel with the capacitance and one could even then add an L-C trap filter between this circuit and the ground plane. In this case, the ground plane would be the equipotential shield surface formed by the AIMD housing 116.

The conductor may be a leadwire, and the leadwire may include platinum, palladium, silver or gold.

The insulator may be flush with the ferrule or housing on the device side. The insulator may include an alumina substrate having at least 96% alumina and the conductor may include a substantially closed pore and substantially pure platinum fill disposed within a via hole and extending between the body fluid side and the device side of the alumina substrate. The solid filled vias may be filled with other material, such as palladium, gold, silver or any alloys thereof, or any other suitable material that forms both a hermetic seal and a low conductivity path through the hermetic seal insulator. In all cases, the via hole fill material must be non-toxic and biocompatible. A hermetic seal may be between the platinum fill and the alumina substrate, wherein the platinum fill forms a tortuous and mutually conformal knitline or interface between the alumina substrate and the platinum fill, wherein the hermetic seal has a leak rate that is no greater than $1\times10^{-7}$ std cc He/sec. An inherent shrink rate during a heat treatment of the alumina dielectric substrate in a green state may be greater than that of the platinum fill in the green state.

A first circuit trace may be disposed on the circuit board, wherein the first circuit trace is electrically coupled between the first end metallization of the two-terminal chip capacitor and an electronics for the implantable medical device. A second circuit trace may be disposed on the circuit board, wherein the second circuit trace is electrically coupled between the second end metallization of the two-terminal chip capacitor and the oxide-resistant electrical connection or the oxide-resistant metal addition.

The first or second low impedance electrical connection may include a ball grid array.

The oxide-resistant metal addition may include a wire, a pad, an L-shaped pad or an L-shaped pad with cutouts or combinations thereof.

The two-terminal chip capacitor may include a resonant frequency above 400 MHz. The two-terminal chip capacitor may include a capacitance of between 300 picofarads and 10,000 picofarads.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 12 gives the formula for the resonant frequency of the capacitor of FIGS. 6 and 11;

FIG. 13 is similar to FIG. 7 except now having very little electrode overlap area;

FIG. 14 is a sectional view taken along lines 14-14 from the structure of FIG. 13, FIG. 15 is a sectional view taken along lines 15-15 from the structure of FIG. 13.

FIG. 19A illustrates a partial-sectional view of a unipolar hermetic terminal;

FIG. 19B is a top view of the structure of FIG. 19A;

FIG. 56A is a sectional view similar to FIG. 55A now with a meander circuit trace;

FIG. 56B is a sectional view similar to FIG. 55B now with a meander circuit trace;

FIG. 57A is a sectional view similar to FIG. 55A now with an inductor circuit trace;

FIG. 57B is a sectional view similar to FIG. 55B now with an inductor circuit trace;

DETAILED DESCRIPTION OF THE PREFERRED EMBODIMENTS

Figure 1:
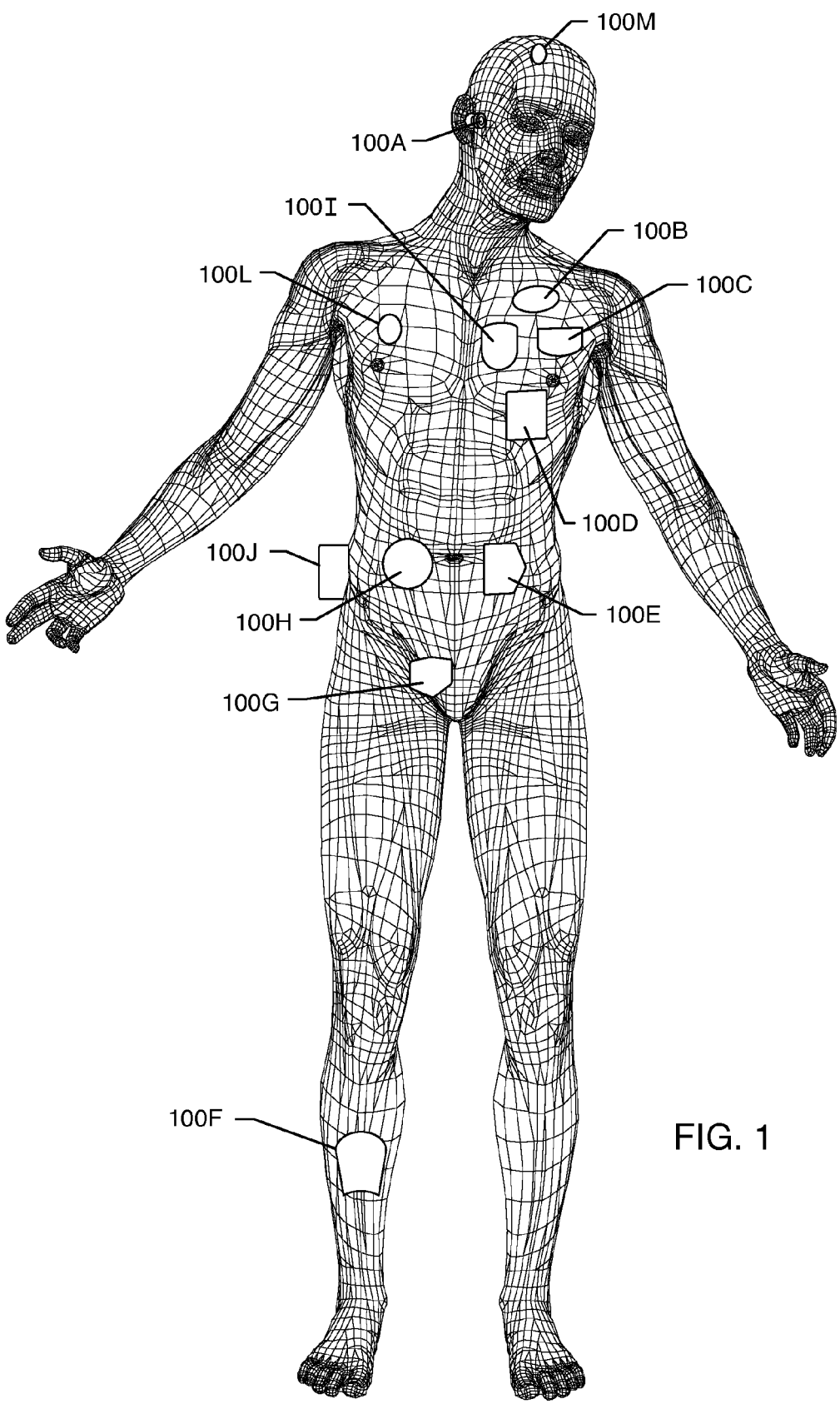
FIG. 1 illustrates a wire-formed diagram of a generic human body showing various types of active implantable and external implantable medical devices currently in use.

FIG. 1 is a wire-formed diagram of a generic human body showing various types of active implantable and external medical devices 100 that are currently in use. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for example but not limited to sensing the onset of the seizure and also providing electrical stimulation to brain tissue to prevent the seizure from actually happening, or for treating memory loss, Alzheimer's and the like. The lead wires that come from a deep brain stimulator are often placed using real time imaging. Most commonly such lead wires are placed during real time MRI. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack.

Figure 2:
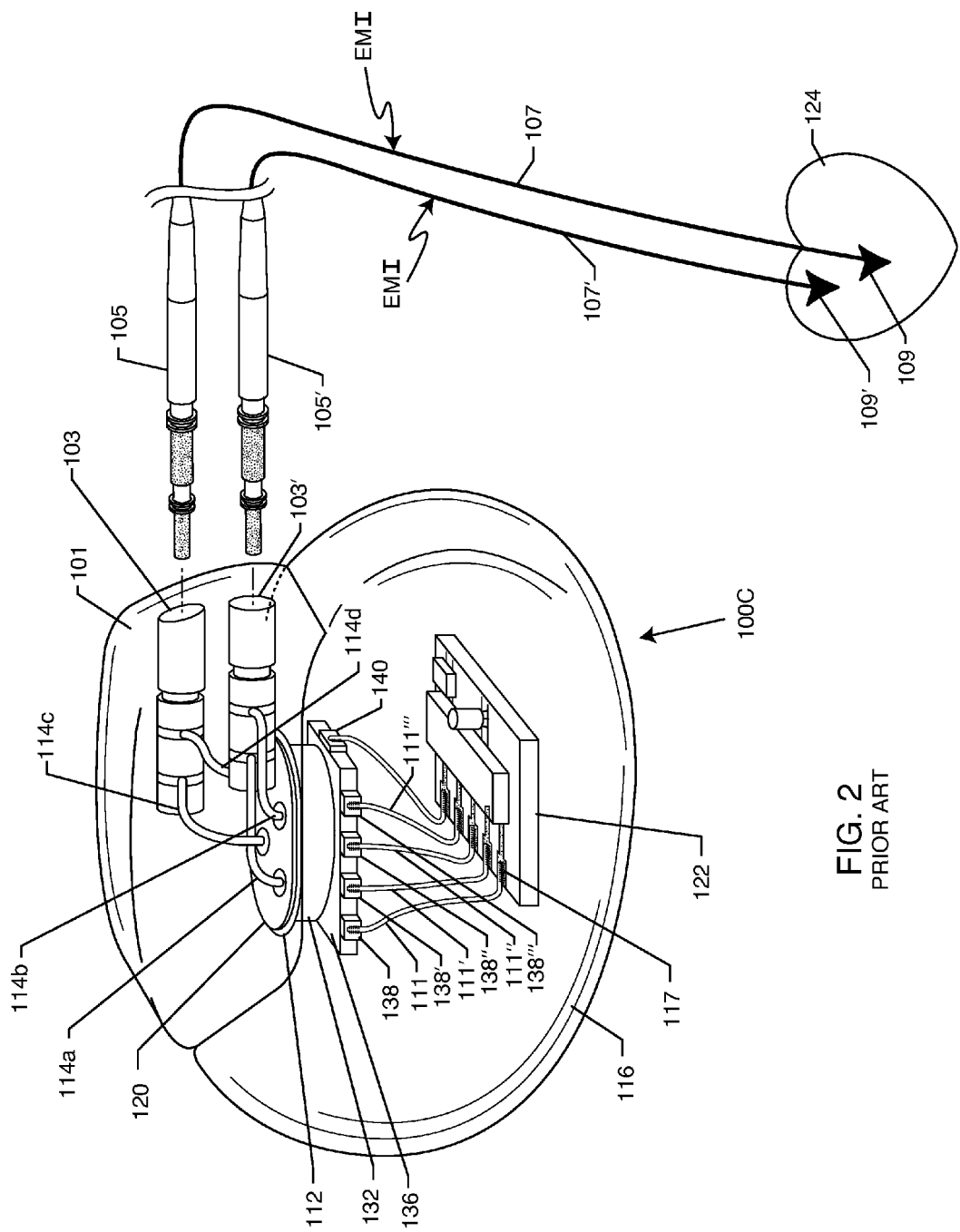
FIG. 2 is a pictorial drawing of a prior art cardiac pacemaker.

FIG. 2 is a pictorial drawing of a prior art cardiac pacemaker 100C. This pacemaker is enclosed in a hermetically sealed titanium housing 116 which also forms an electromagnetic interference (EMI) shield. There is a hermetic seal assembly 120 through which leadwires 114a through 114d pass in non-conductive relationship to the ferrule 112. There is a prior art feedthrough capacitor 132 for decoupling for high frequency EMI signals from the leadwires 114a through 114d to the electro-magnetic shield housing 116. In this case, there is a terminal block 136 which is mounted to the feedthrough capacitor 132 which has wire bond pads 138, 138', 138", 138''' and 140. Wire bond pads are described by U.S. Pat. Nos. 7,623,335; 7,310,216; 7,038,900; and 7,012,192, the contents of all of which are included herein by reference. The wire bond pads 138 provide a convenient method of connecting internal leadwires 111 to contact pads on circuit board 122. This yields a significant cost improvement because these leadwires 111 need not be biocompatible, non-toxic or even biostable. The reason for this is they are within the inert gas-filled hermetically sealed environment of the interior of the pacemaker housing 116. In the prior art without wire bond pads, such as U.S. Pat. No. 4,424,551 or U.S. Pat. No. 5,333,095 or U.S. Pat. No. 5,905,627, the leadwires pass all the way from the body fluid side of the hermetic terminal. These leadwires therefore, have to be biocompatible and generally are of noble material, such as platinum or platinum iridium. This meant that the interior wiring was also of noble metal and therefore, very expensive. Accordingly, the improved pacemaker in the prior art as shown in FIG. 2, has restricted the use of this noble and expensive leadwiring only to those exposed on the body fluid side, which includes leadwires 114a through 114d.

Referring once again to FIG. 2, one can see that there are implantable leads 107 and 107'. Typically, the device 100C would be a dual chamber bipolar pacemaker. Each of the leads 107 and 107' is routed to a different cardiac chamber. In this case, lead 107 has distal electrodes 109 located in the right ventricle. Lead 107' has distal electrodes 109' located in the right atrium. There are proximal end connectors 105 and 105' designed for insertion into ISO Standard IS-1 connector ports 103 and 103'. Therapeutic pacing pulses are delivered from circuit board electronics 122 and directed through leads 107 and 107' to stimulate myocardial tissue. At the same time, low frequency sensed biological frequencies (generally below 1 kHz) are sent on the same lead conductors and routed to sensing circuits also located on circuit board 122. It will be appreciated that circuit board 122 is just a general representation of what could be several circuit boards, flex cables, hybrid chips and the like.

Figure 3:
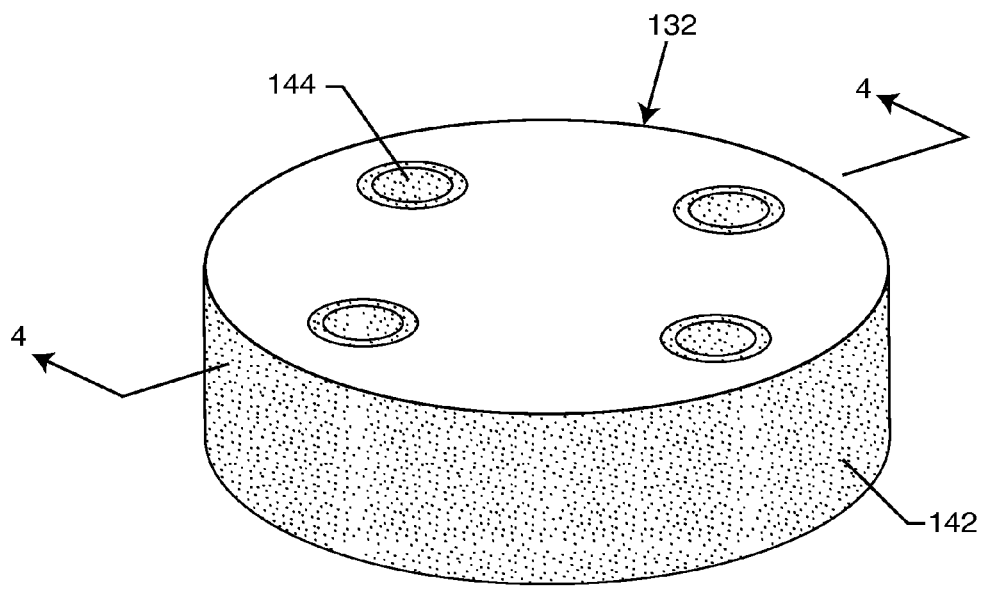
FIG. 3 is a pictorial view of the quad polar feedthrough capacitor of FIG. 2.

FIG. 3 is a pictorial view of the quad polar feedthrough capacitor 132 previously described in FIG. 2. It has four through holes which are metallized with a conductive material 144. There is also an outside diameter metallization 142.

Figure 4:
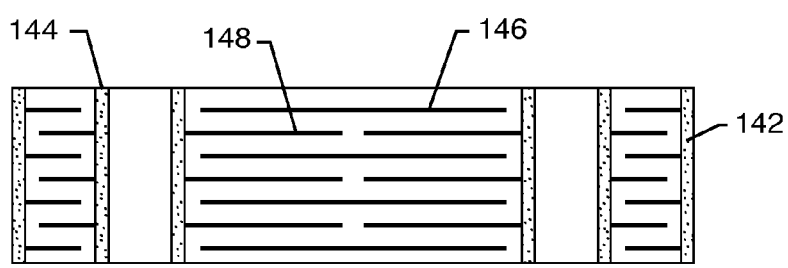
FIG. 4 is a sectional view taken from section 4-4 of the structure of FIG. 3.

FIG. 4 is a sectional view taken from section 4-4 from FIG. 3 showing the internal electrode plates of the quad polar feedthrough capacitor 132. The ground electrode plate set 146 is shown in stacked and interleaved relationship with the active electrode plate sets 148. The overlap of the active and ground electrode plates creates capacitive active areas. One can see that the ground electrode plates are connected to the outside diameter metallization 142 and the active electrode plate sets are connected to the inside diameter of their respective feedthrough holes.

Figure 5:
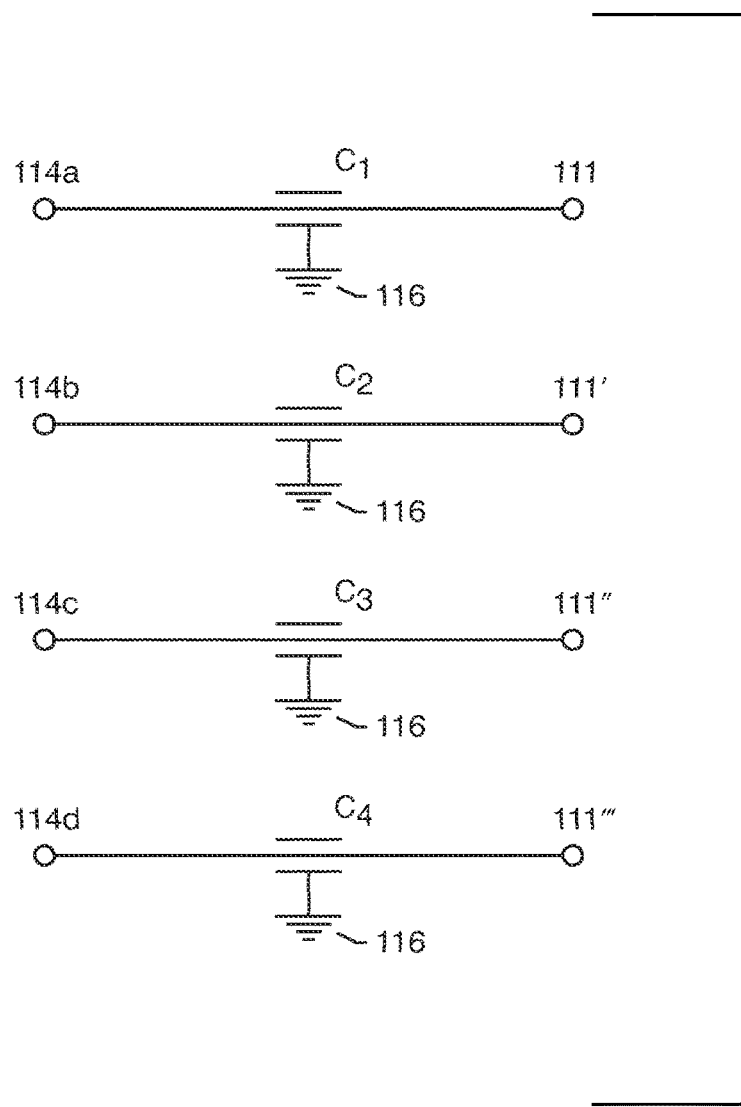
FIG. 5 is a schematic diagram of the quad polar feedthrough capacitor of FIGS. 2 and 3.

FIG. 5 is a schematic diagram of the quad polar feedthrough capacitor 132 previously illustrated in FIGS. 2 and 3. Feedthrough capacitors are very unique broadband three-terminal capacitors. Referring once again to FIG. 5, one can see the capacitor $C_1$ has an input terminal 114A, an output terminal 111 and a ground terminal 116. There is no inductance shown in this circuit since feedthrough capacitors really don't have any series inductance. It is for this reason that their self-resonant frequencies are very high in frequency and furthermore, after a slight resonant dip, feedthrough capacitors continue to perform up to very, very high frequencies (even up to 18 GHz and beyond).

Figure 5A:
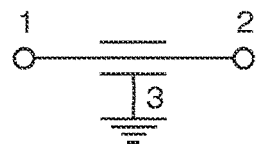
FIG. 5A is a schematic diagram of a three terminal feedthrough capacitor.

FIG. 5A is taken from just one of the circuits of the quad polar capacitor previously described in FIG. 5. Referring to FIG. 5A, one can see that the feedthrough capacitor is truly a three-terminal device. It has an input terminal 1, an output terminal 2 and a ground terminal 3, as shown.

Figure 6:
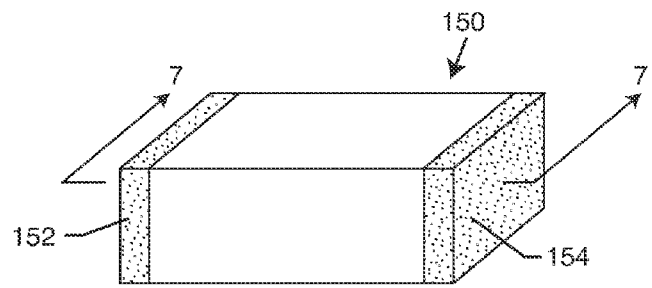
FIG. 6 is a pictorial view of a prior art MLCC chip capacitor.

FIG. 6 is a pictorial view of a prior art MLCC chip capacitor 150. In general, the capacitor of FIG. 6 is known as a two-terminal capacitor and the end terminations 152 and 154 are generally on opposing faces of the capacitor, which may be rectangular or square. This is in marked contrast to the prior art feedthrough capacitor previously illustrated in FIG. 3. Feedthrough capacitors are distinguishable as three-terminal devices, in that, they always have at least one through hole and then outside diameter or perimeter metallization. The capacitor is formed in a block of dielectric material and has a termination surface on the left 152 and a termination surface on the right 154. Note that this is a two-terminal capacitor and hence, we don't describe the active electrodes as active and grounded in this case since the capacitor can be readily reversed. Chip capacitor filters for active implantable medical devices have previously been described in U.S. Pat. Nos. 5,650,759; 5,896,267; 5,959,829; 5,973,906; and 6,459,935, the contents of all of which are incorporated herein by reference. One is also referred to U.S. Patent Publication 2010/0023086 and also U.S. Pat. Nos. 5,735,884 and 5,836,992, the contents of which are also incorporated herein by reference. MLCC chip capacitors act as two-terminal devices and therefore always have a certain amount of internal inductance. Accordingly, they are not as efficient in broadband filtering as a feedthrough capacitor. For a chip capacitor to be effective in this application, it must not only have a very low internal inductance, but it must also have a very low impedance ground connection. For this reason, the use of two-terminal chip capacitors, in a high frequency EMI filtering application, such as that for an AIMD, is counter-intuitive and even contra-indicative. There is one big advantage to two-terminal chip capacitors over feedthrough capacitors and that is cost. Chip capacitors are manufactured in billions per day compared to the relatively low volume of feedthrough, which may be only a few hundred per day. Chip capacitors may be bought for less than $0.05, whereas feedthrough capacitors generally are at least several dollars, if not more than $20 each. It is for this reason that it would be desirable to devise two-terminal chip capacitors and appropriate mounting needs such that they could be effective as AIMD electromagnetic interference filters. This is commonly lacking and is a significant shortcoming of all of the previously mentioned prior art patents referenced herein. This problem has been previously addressed for feedthrough capacitors as described in U.S. Pat. No. 6,765,779, the contents of which are incorporated herein by reference. As taught in the '779 patent, the feedthrough capacitor ground electrode plates are connected to the gold braze of the hermetic seal, thereby providing an oxide-free, low impedance connection, which is very stable. However, none of the prior art has taught how to make a low inductance and low resistance electrical connection for a hermetic filtered feedthrough utilizing chip capacitors as compared to feedthrough capacitors.

Figure 7:
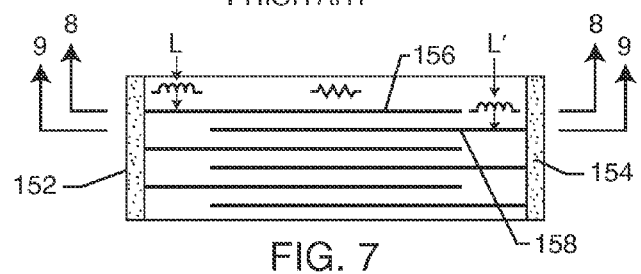
FIG. 7 is a sectional view taken along lines 7-7 from the structure of FIG. 6.

FIG. 7 is taken from section 7-7 from FIG. 6 and shows the electrode plate arrangement of the MLCC capacitor. One can see that the left hand electrodes 156 are connected to termination surface 152 and the right hand electrode plate set 158 is connected to the right hand termination material 154. It should be noted that unlike the feedthrough capacitor previously described in FIGS. 3 and 5, all prior art MLCC (two-terminal) capacitors do have series inductance. These series inductances L and L' are shown inside of the capacitor in the region of the capacitor known as its internal margin area. There would also be added inductance for many external circuit connections (not shown).

Figure 8:
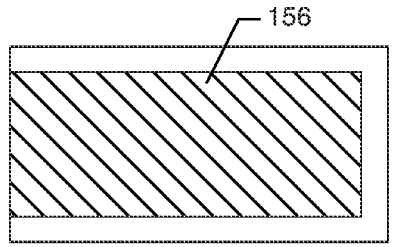
FIG. 8 is a sectional view taken along lines 8-8 from the structure of FIG. 7.

FIG. 8 illustrates the left hand electrode 156 taken from section 8-8 from FIG. 7.

Figure 9:
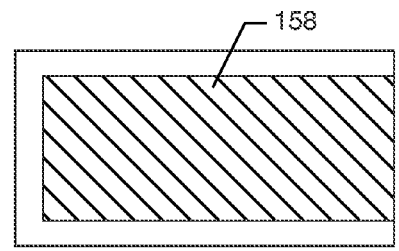
FIG. 9 is a sectional view taken along lines 9-9 from the structure of FIG. 7.

FIG. 9 illustrates the right hand electrode plate set 158 taken from section 9-9 from FIG. 7.

Figure 10:
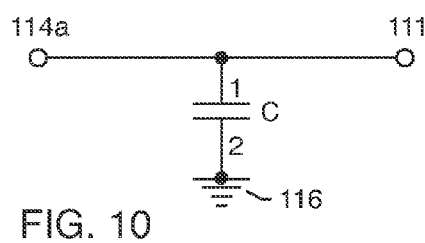
FIG. 10 is an idealized circuit schematic of the capacitor of FIG. 6.
Figure 11:
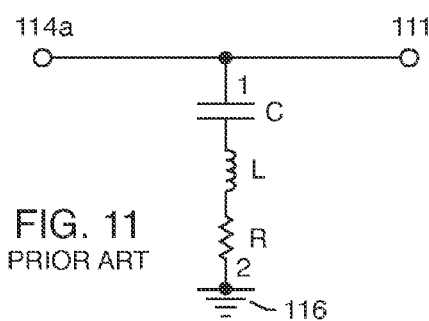
FIG. 11 is a realistic equivalent circuit schematic of the capacitor of FIG. 6.

FIG. 10 is an idealized schematic of the capacitor of FIG. 6. By idealized, this means that this would be an ideal capacitor with no real losses. This capacitor does not actually exist. A more realistic equivalent circuit for the MLCC capacitor of FIG. 6 is illustrated in the schematic of FIG. 11, which includes the capacitance C and also its parasitic inductance L and its parasitic resistance R. As shown in FIG. 10 and FIG. 11, the two-terminals 1 and 2 are illustrated. As will be shown, when this parasitic inductance gets too large and/or the parasitic resistance gets too large, this can seriously degrade the performance of the MLCC capacitor of FIG. 6 as a high frequency filter. All two-terminal capacitors have a resonant frequency. This means they can be monolithic ceramic capacitors, stacked film capacitors or any other type of capacitor that has an equivalent circuit as illustrated in FIG. 11. When the inductive reactance is equal and opposite to the capacitive reactance, the capacitor resonates at $f_r$. Since the capacitive reactance is a minus imaginary turn and the inductance is a positive imaginary turn, when they are equal and opposite they cancel each other out. This means that at resonance, in FIG. 11, the only remaining circuit element would be the resistance element R. If it were not for the presence of this parasitic resistance, at resonance, the capacitor of FIG. 6 would appear as a short circuit (and provide infinite insertion loss or attenuation).

FIG. 12 gives the formula for the resonant frequency of the capacitor of FIG. 6 and FIG. 11. As one can see, the resonant frequency varies inversely with the square root of the inductance times the capacitance.

Referring once again to FIG. 12, one can see that there is an inverse relationship between the resonant frequency $f_r$ and the inductance L and the capacitance C. In the present invention, it is important that the chip capacitor as illustrated in FIG. 6 inherently holds a self-resonant frequency greater than 400 MHz. It is also important that the chip capacitor of FIG. 6 also has a self-resonant frequency of greater than 400 MHz after mounting, which means that the inductance of its connections and circuit traces also must be included in the total inductance L. As will be shown in subsequent drawings, this is challenging and requires novel assembly techniques. It should also be noted that this minimum resonant frequency of 400 MHz corresponds with the capacitive value range required for AIMD EMI filters, namely, that capacitance value range is from 300 picofarads to 10,000 picofarads. In summary, the capacitor of the present invention, after mounting, will range in capacitance from 300 to 10,000 MHz and have a resonant frequency of no less than 400 MHz.

FIG. 13 is very similar to FIG. 7 except that in this case, there is very little electrode overlap area. However, the capacitor body itself is still very long. This means that the parasitic inductance elements L and L' are much larger. This would be an example that would resonate in a much lower frequency. The left hand electrode plate set 156 is shown in FIG. 14 and the right hand electrode plate set 158 is shown in FIG. 15. Again, in this case, L and L' are inductances interior to the capacitor body. The total parasitic inductance L as previously shown in FIG. 11, would be the sum of all of these inductances L and L' (and others not shown). Referring once again to FIG. 13, one can see that the capacitor left hand metallization 152 has been electrically attached to circuit trace 160 using solder or a thermal-setting conductive adhesive or the like 162. The right hand capacitor metallization 154 has been connected to a second circuit trace 164 again using electrical attachment material 162. These outside circuit traces add additional inductance L" and L'" which add directly to the inductance L previously shown in FIG. 11. This is highly instructive in the present invention as it will be shown that in order to use two-terminal chip capacitors one must be very cognizant of both these internal and external inductances as they can seriously degrade the high frequency performance of the EMI filter. For purposes of illustration, the physical dimensions of the chip capacitor shown in FIGS. 7 and 13 are the same (in other words, the same length, the same height and the same overall width).

Figure 16:
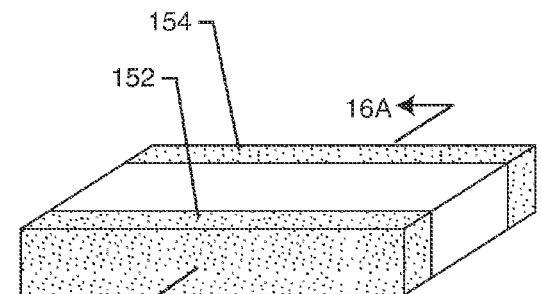
FIG. 16 is similar to FIG. 6, now showing a similar sized capacitor with the electrode plates in a perpendicular orientation.
Figure 16A:
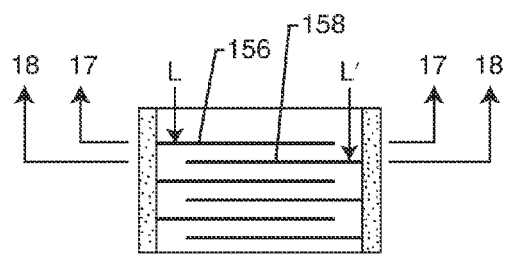
FIG. 16A is a sectional view of the structure of FIG. 16 taken along lines 16A-16A.
Figure 17:
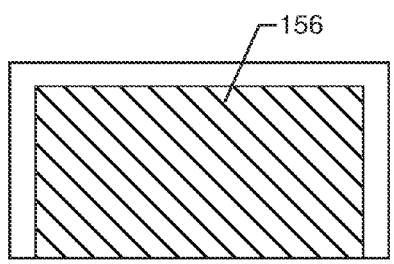
FIG. 17 is a sectional view of the structure of FIG. 16A taken along lines 17-17.
Figure 18:
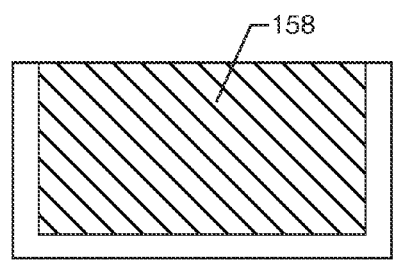
FIG. 18 is a sectional view of the structure of FIG. 16A taken along lines 18-18.

The capacitor of FIG. 16 is also the same length, the same width and the same overall height except that a reverse geometry is used wherein there is an upper and lower metallization 152 and 154. This is better understood by referring to the cross-sectional view taken generally from section 16A-16A from FIG. 16. In this case, the interior electrode plates 156 and 158 are shown. In comparison, these electrode plates 156 and 158 are much shorter in width than the electrode plates previously illustrated in FIGS. 13 and 7. This has the effect of dramatically dropping the amount of internal inductance L and L'. Accordingly, this type of capacitor structure will have a much higher self-resonant frequency and therefore, be a superior high frequency filter.

Figure 19:
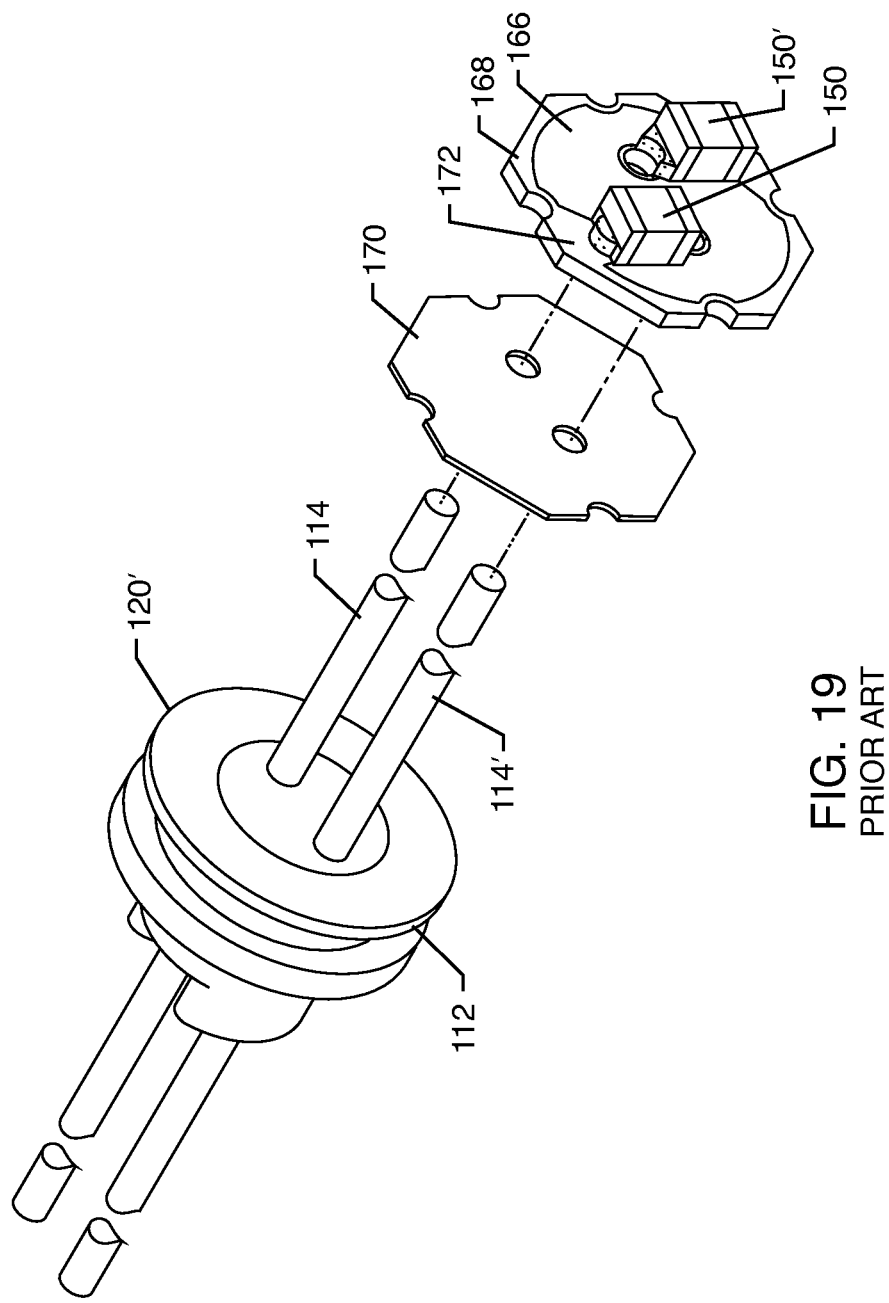
FIG. 19 illustrates a prior art bipolar hermetic feedthrough assembly.

FIG. 19 illustrates a prior art bipolar hermetic feedthrough assembly 120' along with a circuit trace 168 on which two MLCC chip capacitors 150 and 150' are mounted. FIG. 19 was taken from U.S. Pat. No. 5,896,267, the contents of which are incorporated herein by reference. Referring to FIG. 19, there are several positive features, and one undesirable feature that hindered commercialization of this structure. As illustrated in FIG. 19 the metallization of each of the chip capacitors 150 and 150' closely abuts the leadwires 114 and 114'. Since the chip capacitors are relatively short and this electrical connection path is relatively short, this means that there is very little inductance (and resistance) formed on the lead attachment side. The circuit board has a ground metallization 168 which attaches directly to the titanium ferrule 112. There is an insulating washer 170 dispersed there between. An electrical connection material (not shown) connects the ground metallization of the circuit board 168 to the titanium ferrule 112. Here is where the impediment lies. First of all, there is a significant length of circuit trace 172 which adds a slight amount of inductance to the capacitor's own internal inductance. Moreover, the electrical connection material between metallization surface 168 and the titanium ferrule provides a very high resistance connection. This is because during the gold brazing operation or other processing, all titanium surfaces form an oxide, a trioxide or the like. Oxides of titanium are so rugged and so stable that they are a common pigment used in paints. In other words, once formed, these oxides will remain in place for decades. These oxides can act as either a resistor or a semiconductor greatly increasing the amount of resistance R previously illustrated in the capacitor's equivalent circuit shown in FIG. 11. The inventors have seen cases wherein R, due to the formation of the titanium oxide, can increase to as much as 3 ohms or to even above 30 ohms. When one considers that the purpose of this capacitor is to simulate a very low impedance at high frequencies, the presence of a significant amount of R is a counterproductive consequence. Having a significant resistance in this location substantially degrades the overall attenuation performance of this filter.

FIG. 19A is a partial-sectional view of a unipolar hermetic terminal taken from FIG. 1 of U.S. Pat. No. 5,650,759 (Hittman, et al.). The contents of the U.S. Pat. No. 5,650,759 are incorporated herein by reference. Referring to FIG. 19A, one can see that there is a conductive ferrule 112, which is typically of titanium; a hermetic seal insulator 206, which in a preferred embodiment would be an alumina ceramic or a glass, and a leadwire, which is continuous and passes from a body fluid side 114 to a device side 111. The ferrule 112 has a flange which is generally laser welded into the hermetically sealed housing of an active implantable medical device (not shown). The device side, otherwise known as the inside, would be inside the hermetically sealed space where body fluids cannot penetrate. Capacitor mounting surface 258 is towards the device inside and is also an ideal location for a capacitor mounting location. In fact, many prior art feedthrough capacitors have been mounted to this surface 258.

FIG. 19B is taken from the same Hittman reference from FIG. 4 and of the same Hittman '759 patent. Shown is the top view of a monolithic ceramic chip capacitor 150 which is electrically and mechanically attached on its right end to electrical attachment 184 and then to leadwire 111. This close proximity reduces inductance and also reduces resistance. In the case where the lead is of pure platinum, the electrical resistance of connection 184 will also be extremely low. Where this invention diminishes in performance is on the left hand side of the capacitor, where an electrical attachment 184' is made directly to the top of the titanium ferrule 112, which in many cases can be heavily oxidized resulting in a resistive layer. At first glance, it would seem that the electrical attachment 184' in FIG. 19B is very close to a gold braze 260. However, in this case, 260 is an air gap. This is best understood by referring once again to FIG. 19A where one can see that the outside diameter of gold braze 212 to the alumina ceramic insulator 206 is disposed towards the body fluid side and that the circular ring, labeled 260, is nothing more than an air space. Accordingly, the Hittman '759 patent does not teach an attachment of the capacitor ground to other than an oxidizable titanium ferrule 112.

Figure 19C:
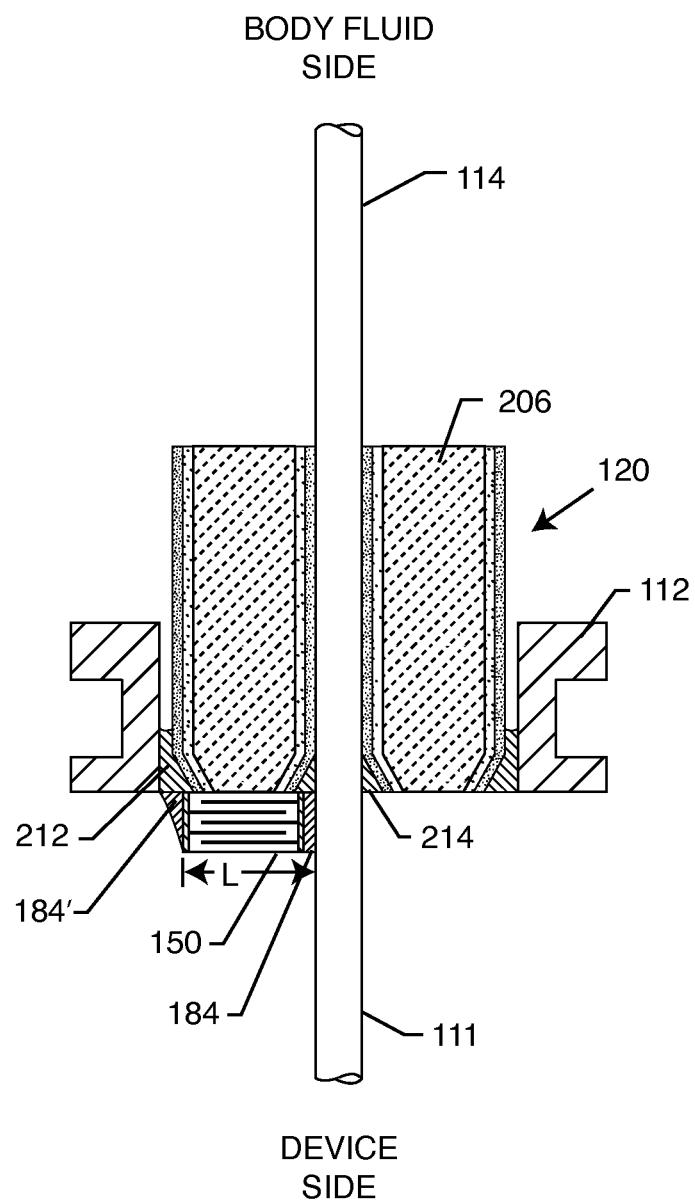
FIG. 19C is an exemplary embodiment of a novel feedthrough of the present invention.

FIG. 19C is in accordance with the present invention and teaches a desirably improved method as compared to FIG. 19B. In this case, the capacitor 150 active electrode plates are attached to its termination which is connected using electrical contact material 184 directly to the leadwire 114. In the case where the leadwire is a noble material, such as platinum or a platinum based material, then a very low resistance and inductance connection would be formed. On the ground side of the capacitor (the left side), there is another electrical attachment 184' formed directly from the capacitor ground metallization to gold braze material 212, which just happens to also form the hermetic seal between the ferrule 112 and the alumina ceramic insulator 206. In summary, the novel structure, as shown in FIG. 19C, makes a ground attachment of the capacitor directly to a noble (gold) surface, which will remain relatively oxide-free over the design and lifetime of the device.

Referring once again to FIG. 19C, one can see that the chip capacitor 150 is relatively short L. It is also relatively wide (not shown). For example, a preferred form factor is that of the chip capacitor previously described in FIG. 16. In any event, in order for the chip capacitor to be effective as a high frequency EMI filter, it must have a self-resonant frequency of no less than 400 MHz. In a particularly preferred embodiment, the chip capacitor would have a self-resonant frequency of over 800 MHz.

Referring back to FIG. 11, prior art drawing 19B marginally minimizes the inductive term L, but does an extremely poor job of minimizing the resistive term R. However, the device described in FIG. 19C, in accordance with the present invention, substantially increases minimizing the inductive term and the resistive term, leading to optimal performance of the MLCC capacitor 150 of the high frequency EMI filter.

Figure 20:
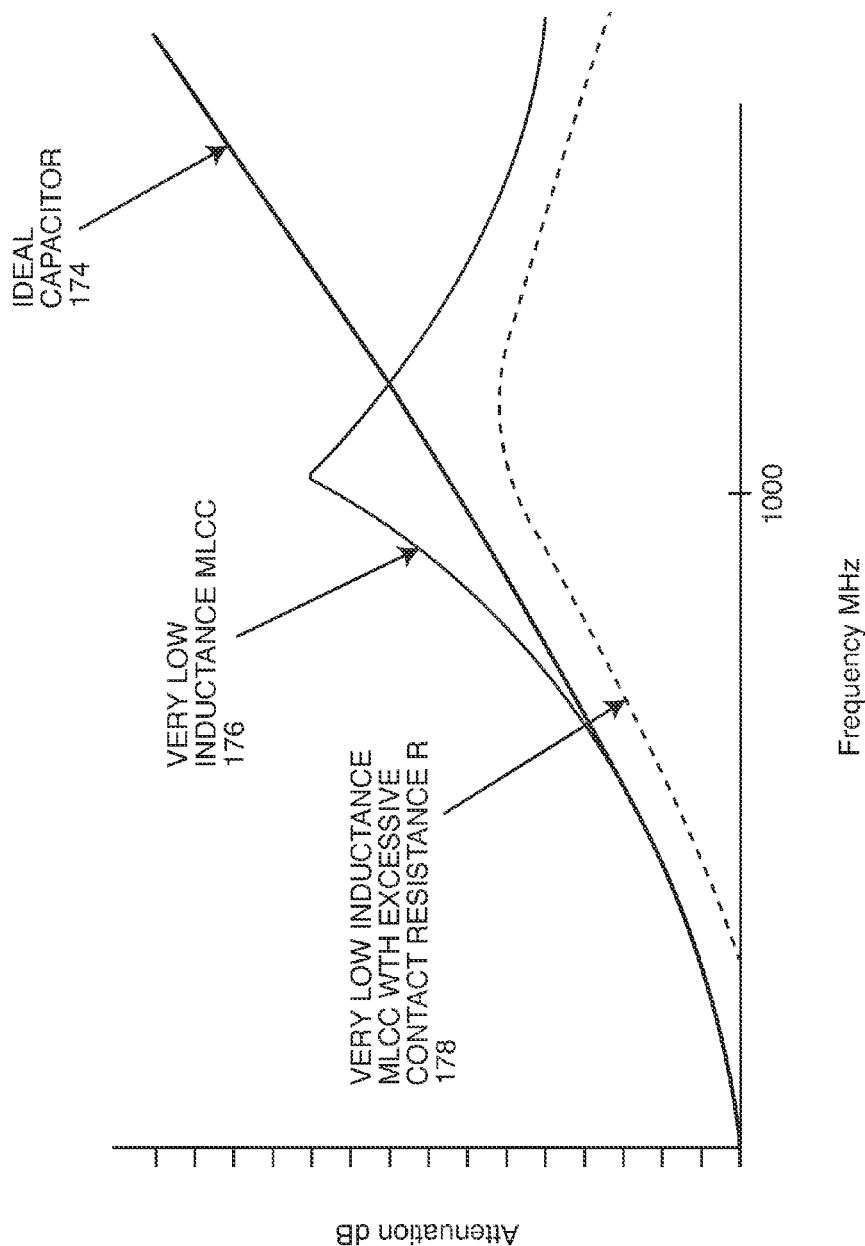
FIG. 20 is a graph of frequency versus attenuation for a variety of capacitors.

FIG. 20 illustrates the explanation given in FIG. 19. First, an ideal capacitor curve 174 is shown. The y-axis gives attenuation in decibels and the x-axis provides frequency in megahertz. In this graph, the line labeled 'ideal capacitor' (which in reality does not exist) would be the performance of the capacitor shown in FIG. 10. It should be noted that a feedthrough capacitor, which is a three-terminal device, very closely approximates the performance of an ideal capacitor. Referring once again to FIG. 20, one can see that a very low inductance MLCC construction 176 (including its internal circuit traces) would resonate at a fairly high frequency. In this case, we're showing that the MLCC capacitor would resonate at about 1000 MHz. As previously mentioned, referring to FIG. 11, when the MLCC capacitor is at resonance, the C and L reactive components cancel each other and the capacitor simulates a short circuit except for its internal resistance. As described in conjunction with a prior art FIG. 19, there is, however, a significant amount of contact resistance due to titanium oxides. Referring once again to the very low inductance MLCC curve 176, one can see that the attenuation peaks and then falls off very rapidly after resonance. The reason for this is that above resonance, the two-terminal capacitors inductance will start to dominate. In other words, referring to FIG. 11, the positive J$\Omega$L turn will become larger in value than the $-Jx_C$, meaning that the structure will look increasingly inductive and accordingly have lower and lower insertion loss versus frequency. When one gets to very high frequencies, the attenuation is seriously degraded. In the case of the structure shown in FIG. 19, this probably would have been acceptable except for the fact that the ground electrical contact 168 to the ferrule 112 was to a heavily oxidized surface. This results in a great deal of contact resistance shown as curve 178 of FIG. 20. As one can see, the entire capacitor performance curve measured in decibels has been degraded at all frequencies. This simply would not provide adequate protection for the AIMD against powerful EMI emitters such as cellular telephones and the like.

Figure 21:
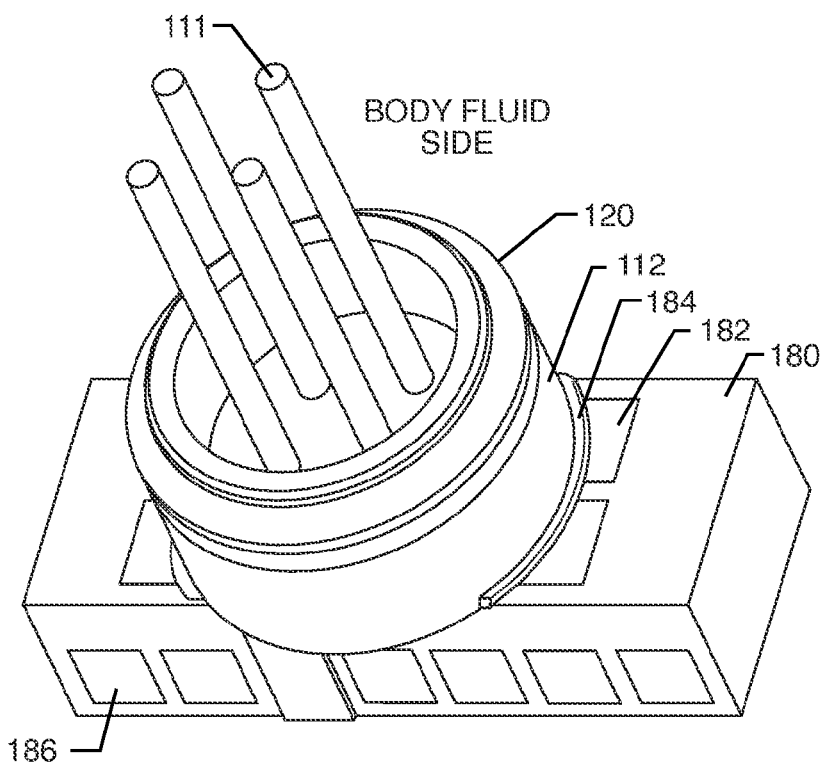
FIG. 21 is a perspective view of a prior art feedthrough.
Figure 22:
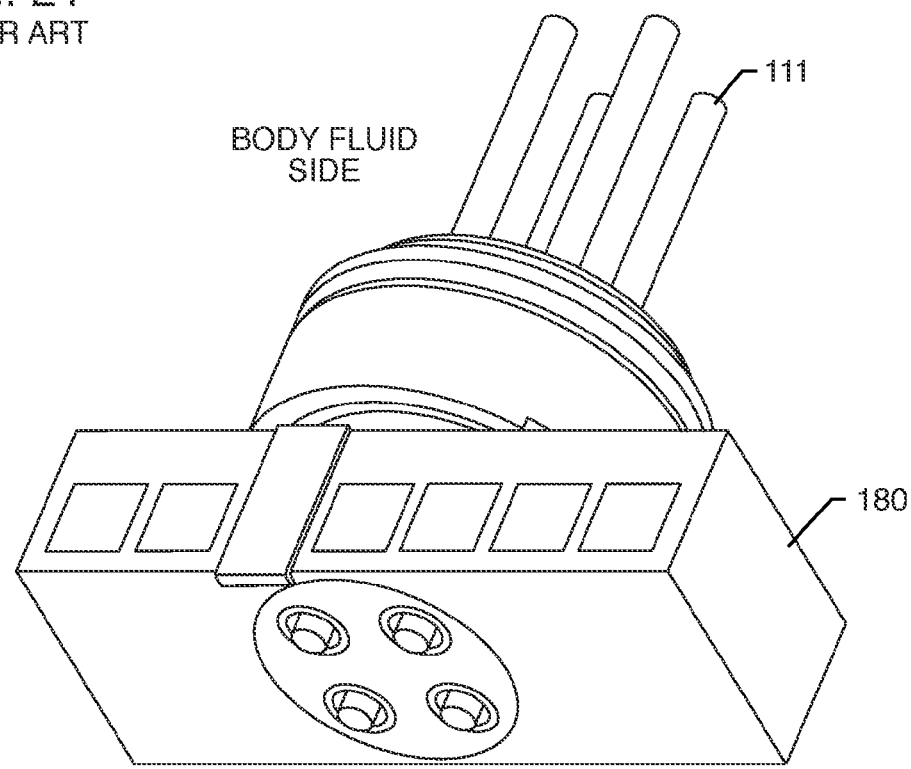
FIG. 22 is another perspective view of the structure of FIG. 21.

FIGS. 21 and 22 are taken from U.S. Pat. No. 7,693,576, the contents of which are incorporated herein by reference. In this case, there is a hermetic terminal 120 with a titanium ferrule 112. The ferrule 112 is shown electrically connected 184 to ground circuit pads 182. There are internal circuit traces (not shown) that route these ground traces to embedded MLCC chip capacitors, which are routed to other circuit traces and then routed to leadwire 111.

FIG. 22 shows the reverse view of the filtered hermetic terminal structure of FIG. 21. This prior art structure has several disastrous problems associated with it. First of all, the electrical connection material 184, which forms the primary ground for the invention, is connected directly to the heavily oxidized titanium ferrule surface 112 in a similar manner that created the high resistance of the design of FIG. 19. FIG. 21 also has another issue, in that, the routing of internal circuit traces creates a large inductive loop which adds directly to the inductance L previously illustrated in FIG. 11. Referring to the equation in FIG. 12, this means that the resonant frequency of this structure will be substantially reduced.

Figure 23:
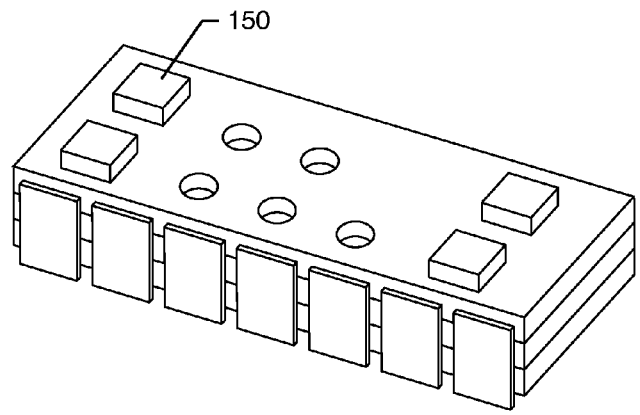
FIG. 23 is a perspective view of the filtered hermetic terminal structure of FIGS. 21 and 22.
Figure 24:
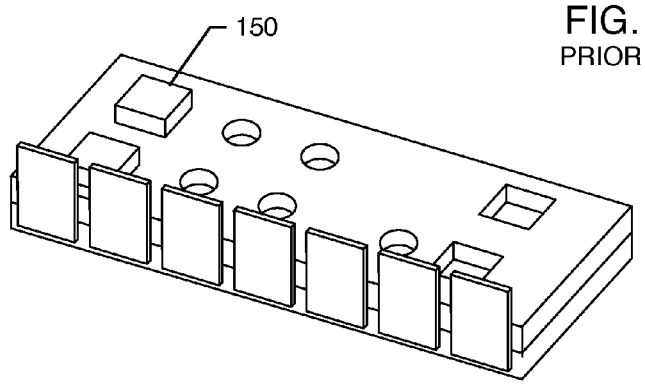
FIG. 24 is a sectional perspective view of the filtered hermetic terminal structure of FIG. 23.
Figure 25:
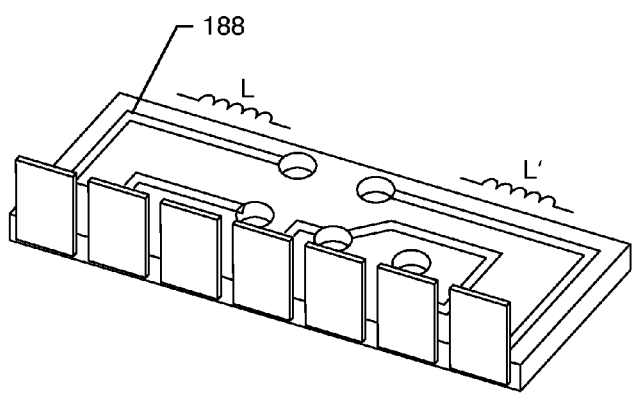
FIG. 25 is another sectional perspective view of the filtered hermetic terminal structure of FIG. 23.

FIGS. 23 through 25 are sections taken from various locations of the structure of FIG. 21. Shown are embedded chip capacitors 150 along with embedded circuit traces 188. As one can see in FIG. 25, there is a very large amount of inductance L and L' associated with these long internal circuit traces.

Figure 26:
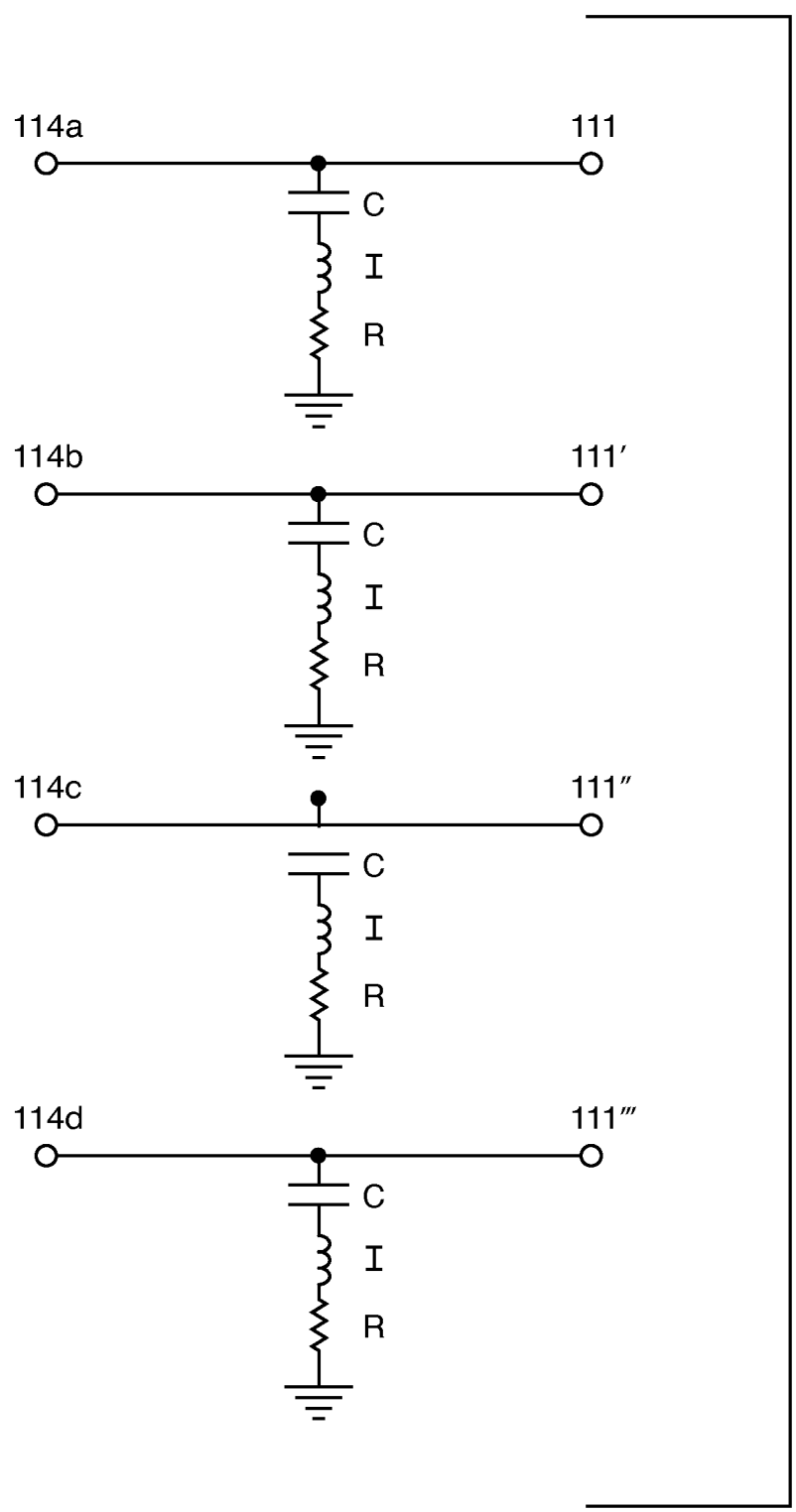
FIG. 26 is an electrical schematic of the structure of FIGS. 21-25.

FIG. 26 is the schematic diagram of the structure illustrated in FIGS. 21 and 22 showing a capacitor formed by the chip capacitor 150 and then a very significant amount of inductance and a significant amount of resistance. As previously mentioned, the large value of inductance comes from the relatively long loops embedded in the circuit board. A relatively large value of resistance also results from the ground connection that is made directly to the heavily oxidized titanium surface.

Figure 27:
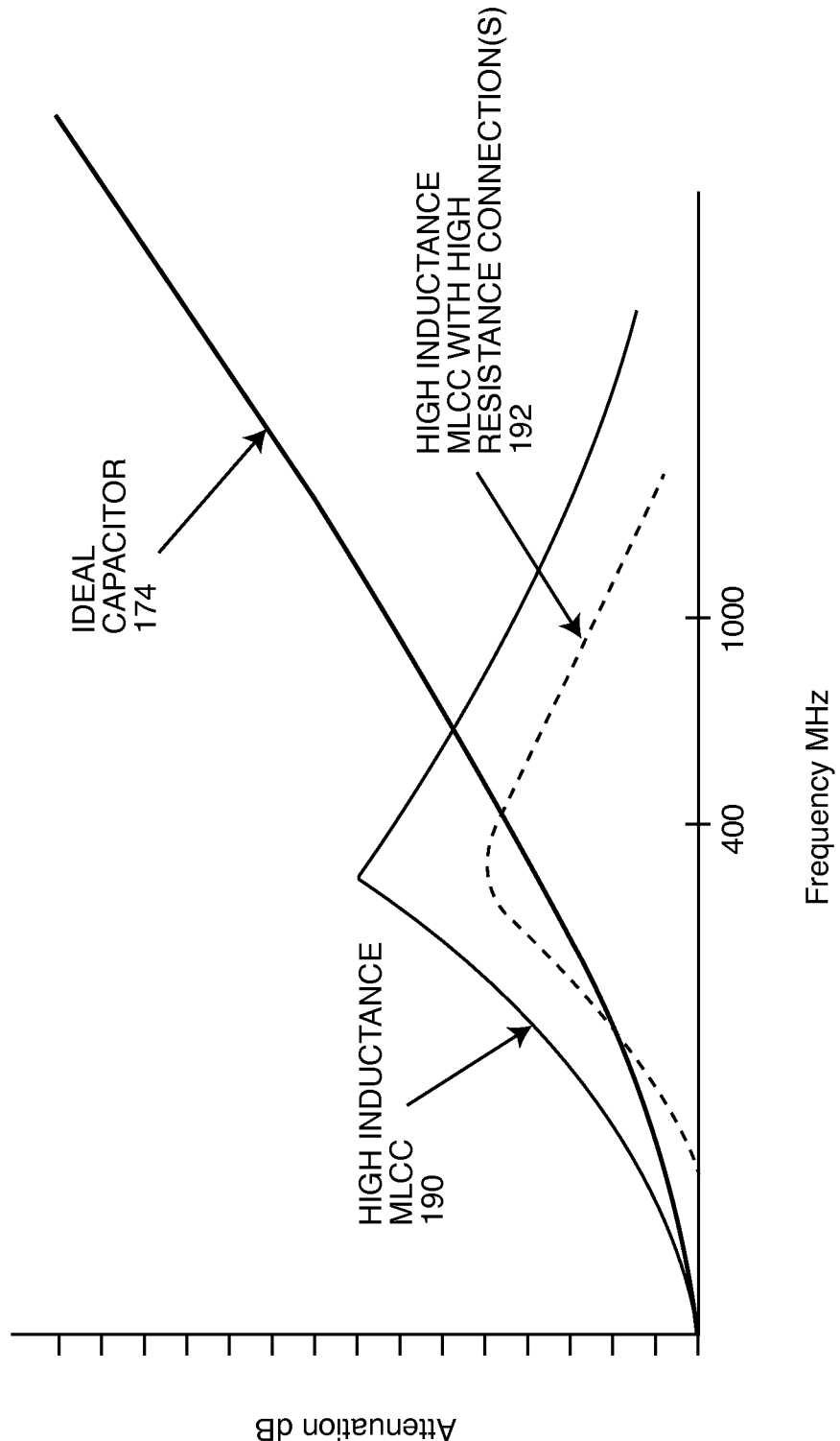
FIG. 27 illustrates the attenuation versus frequency performance of the prior art filtered hermetic terminal previously illustrated in FIG. 21.

FIG. 27 illustrates the attenuation versus frequency performance of the prior art filtered hermetic terminal previously illustrated in FIG. 21. Again, the ideal capacitor performance curve 174 is illustrated. One can see that the high inductance MLCC curve 190 now resonates at a much lower frequency (below 400 MHz) so that by the time it reaches 1000 MHz, the attenuation is significantly degraded such that it would not provide adequate attenuation against cell phones and other emitters. Furthermore, not only is this a high inductance structure, it is also a high resistance structure. So the real curve, or the resulting curve, is actually 192 wherein the resonant dip and the overall filter performance are both seriously degraded. Again, as with the structure shown in FIG. 19, the structure illustrated in FIG. 21 lacked commercial success.

Figure 28:
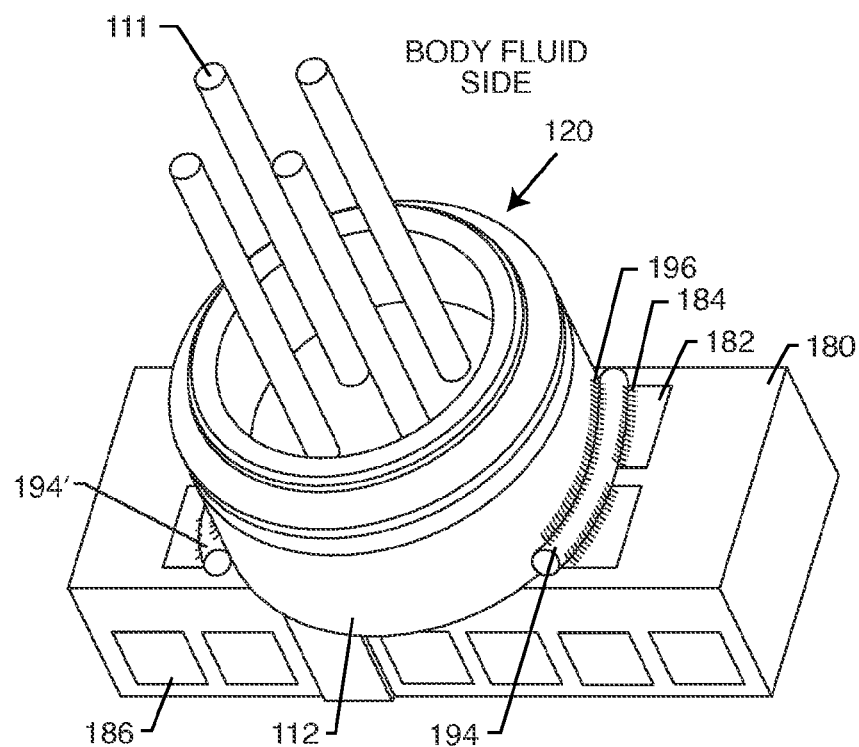
FIG. 28 is similar to FIG. 21, now showing a noble metal leadwire laser welded to the ferrule.

FIG. 28 is very similar to the filtered feedthrough structure previously illustrated in FIG. 21. However, in this case, there is a very important difference. A noble leadwire, such as a platinum leadwire 194, has first been laser welded or brazed 196 to the titanium ferrule 112. Brazing or welding penetrates oxides forming a very low resistance metallurgical connection. This metallurgical connection is very stable and will not form oxides over time. By using a suitable oxide-resistant material, such as platinum, one can then make an essentially oxide-free electrical connection 184 to the ground electrode circuit traces 182. Material 184 can be a solder, thermal-setting conductive adhesive or the like. A laser weld 196 at leadwire 194 can be a number of materials, including: platinum, gold, tungsten, iridium, palladium, niobium, tantalum, ruthenium, rhodium, silver, osmium, or combinations thereof. Nonlimiting examples of platinum based materials include platinum-rhodium, platinum-iridium, platinum-palladium, or platinum-gold. Naturally occurring alloy examples include platiniridium (platinum-iridium), iridiosmium and osmiridium (iridium-osmium) are also usable. There is a corresponding platinum leadwire 194' shown on the opposite side of the capacitor. This is important to minimize the inductive loop area.

Figure 29:
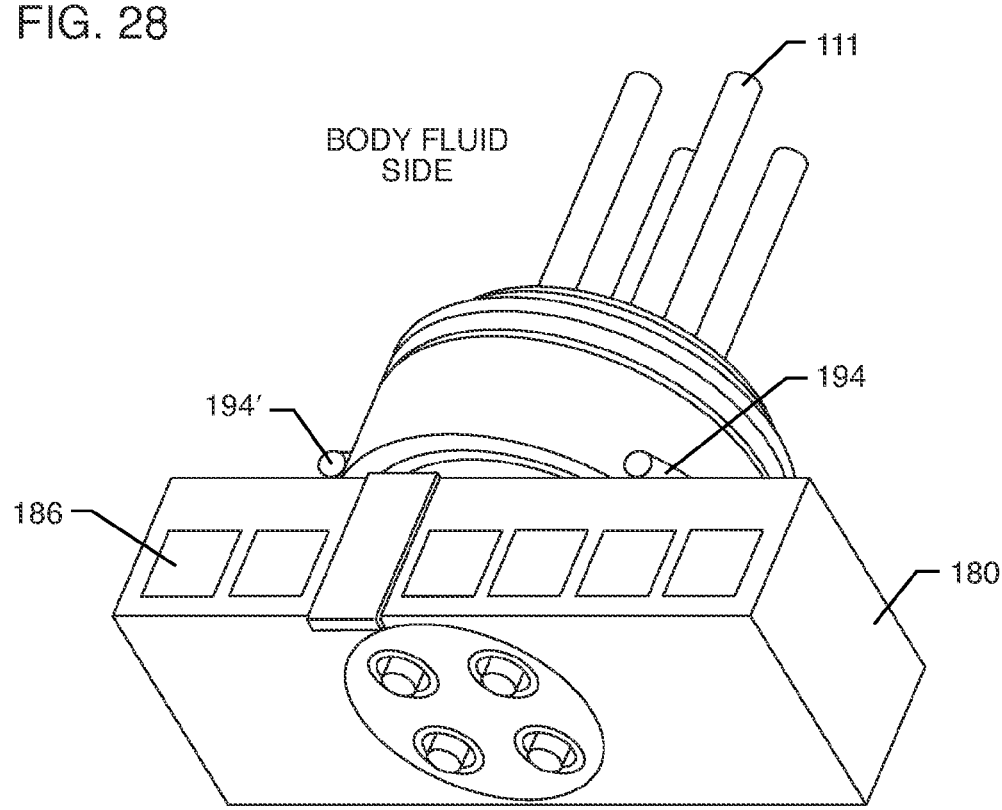
FIG. 29 is a bottom perspective view of the structure of FIG. 28.

FIG. 29 is the structure of FIG. 28 shown inverted. It will be appreciated that the novel structure of FIG. 28 has significantly reduced the value of R in FIG. 11. However, the value of the inductance L has not been significantly changed and is still problematic.

Figure 30:
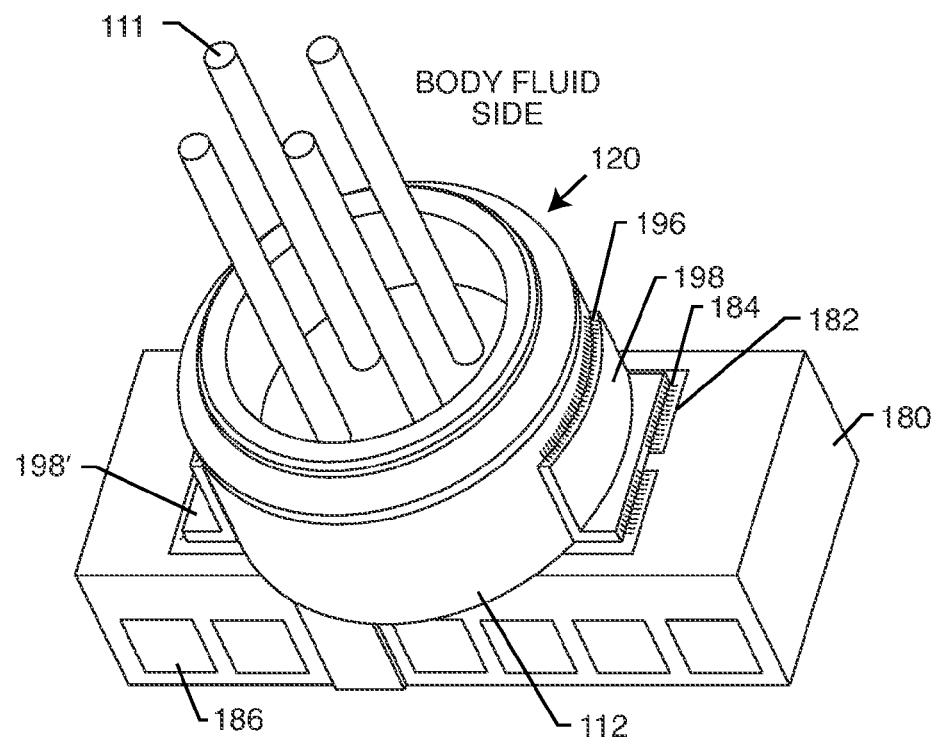
FIG. 30 is similar to FIG. 21, now showing a noble metal bracket laser welded to the ferrule.

FIG. 30 is very similar to FIG. 28 except that the platinum laser welded leadwire 194 has been replaced by an L-shaped bracket 198 which is laser welded 196 to the ferrule 112. Like for the case of the platinum leadwire 194, this bracket is of a non-oxidized material suitable for soldering or connection by a thermal-setting conductive material 184 to the ground circuit pad 182.

Figure 31:
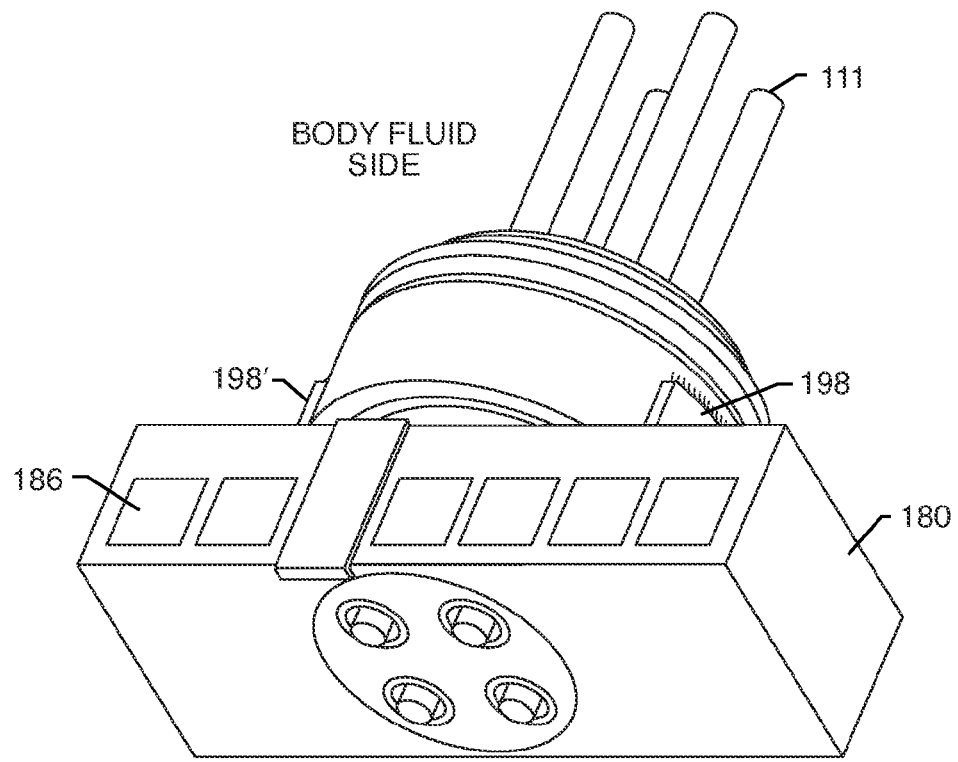
FIG. 31 is a bottom perspective view of the structure of FIG. 30.

FIG. 31 is the inverse view of the structure of FIG. 30.

Figure 32:
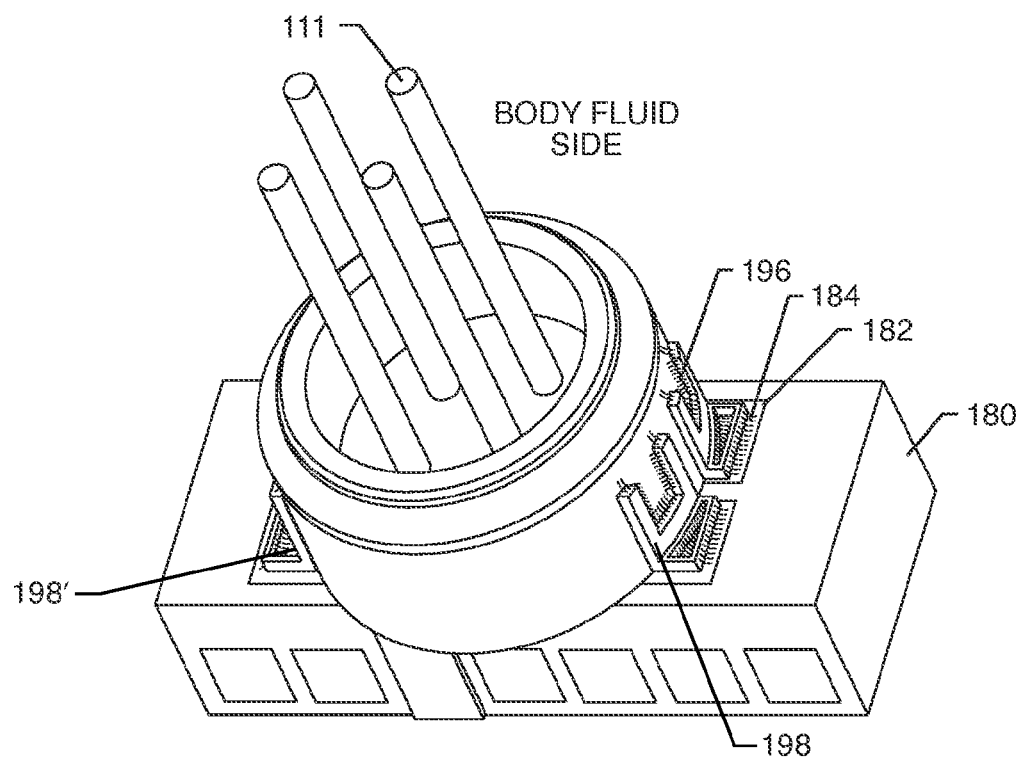
FIG. 32 is similar to FIG. 21, now showing another noble metal bracket laser welded to the ferrule.
Figure 33:
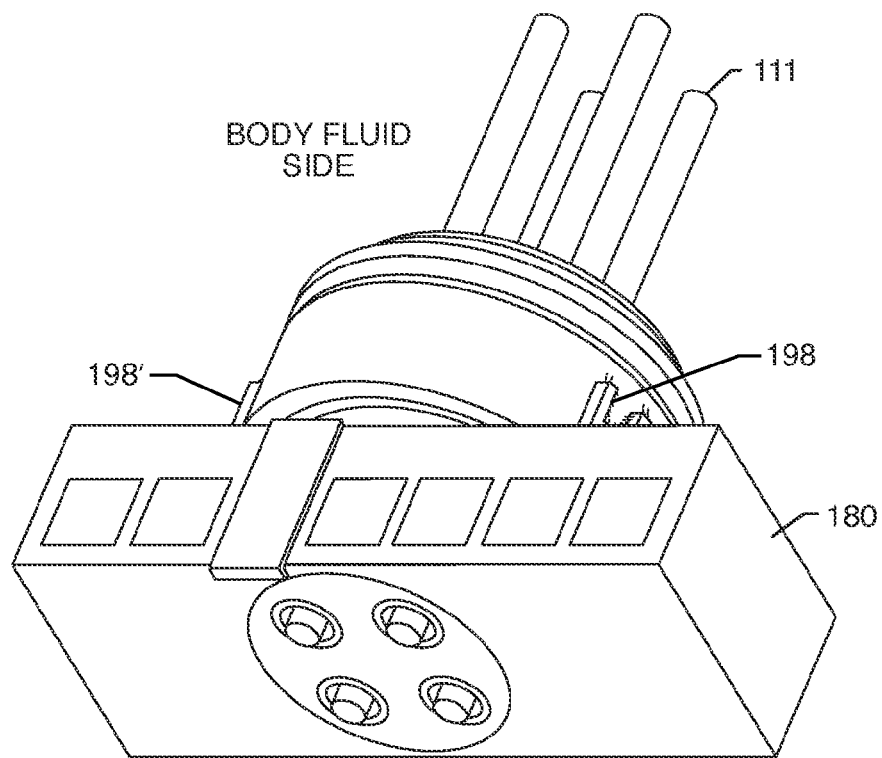
FIG. 33 is a bottom perspective view of the structure of FIG. 32.

FIG. 32 is very similar to FIGS. 28 and 30 except in this case, there are four L-shaped brackets 198 with cut outs to increase the laser weld area 196. At this point, it has been demonstrated that there are a number of ways to make a very low resistance oxide-free electrical connection to a circuit board or circuit traces or pads.

Figure 34:
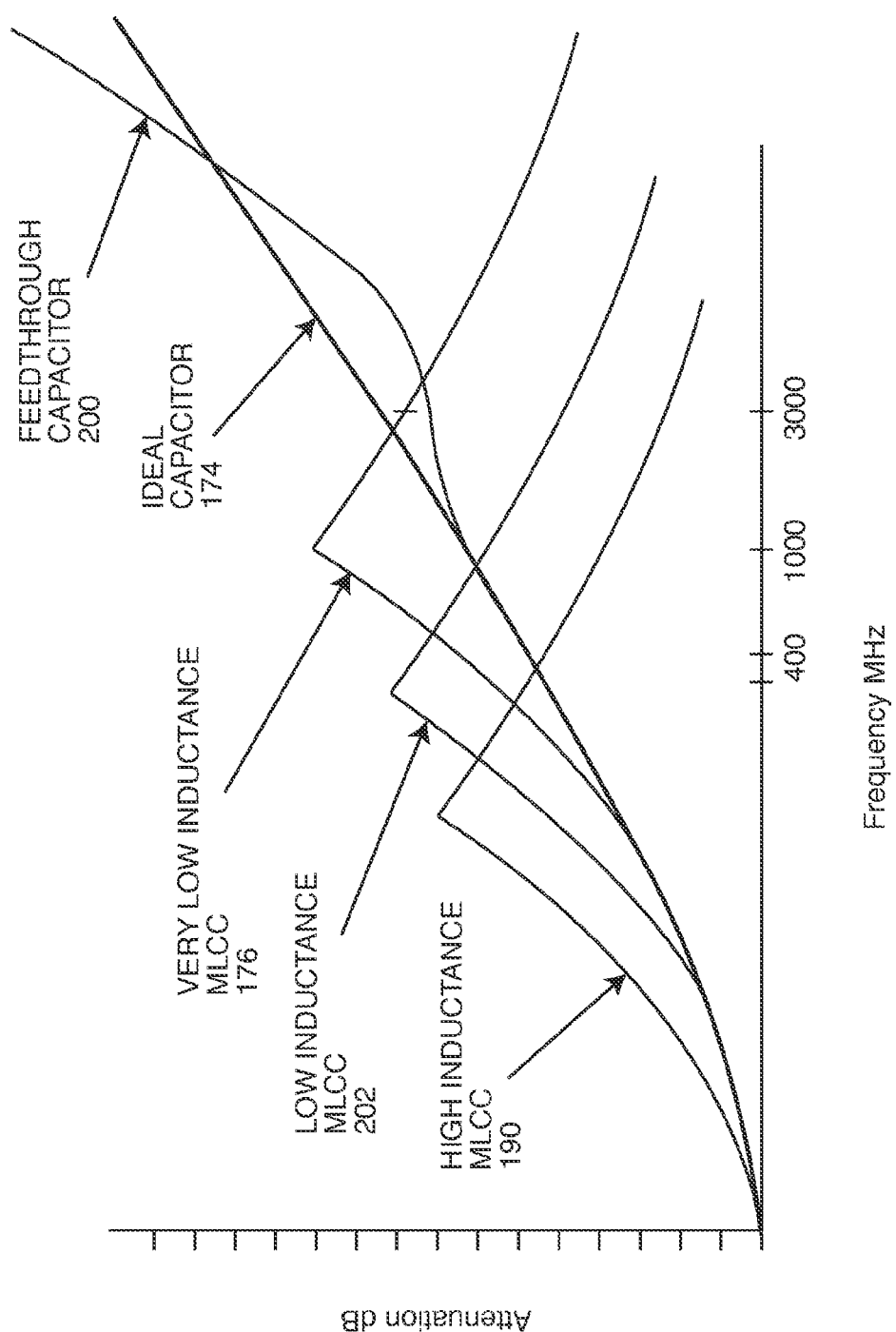
FIG. 34 illustrates the attenuation versus frequency performance of a family of filter designs.

FIG. 34 assumes that a very low resistance connection has been made. Referring once again to FIG. 11, the resistance R in this case, has been minimized and essentially encompasses the internal resistance of the capacitor's electrode plates, otherwise known as the capacitor's series resistance. This will be described in more detail later. FIG. 34 represents a family of filter performance curves versus frequency. Again, the ideal capacitor curve 174 is shown. The attenuation curve for a typical feedthrough capacitor 200 is also shown. A low resistance, high inductance MLCC 190 is shown, which clearly indicates that this type of construction is not suitable at high frequencies. Even a low inductance MLCC 202 still does not provide enough high frequency attenuation at cellular telephone, microwave oven, or radar frequencies. It is only a very low inductance MLCC 176 that also has a very low resistance connection that would provide a high enough resonant frequency (around 1000 MHz) such that after resonance, its degradation does not drop so much before 3 GHz (3000 MHz). The reason 3 GHz is a very important number is that it has been shown by a number of standards body and experimenters that the human body itself becomes a very effective reflector and absorber of electromagnetic interference at 3 GHz and above. In other words, filters for AIMDs really do not need to be effective at frequencies much above 3 GHz. Referring back to FIG. 34, one can see that a very low inductance, very low resistance construction 176 can make an MLCC effective enough to offer substantial attenuation all the way to 3 GHz before it continues to degrade. The attenuation numbers in dB, of course, also vary with the capacitance value. So this area is left blank deliberately.

Figure 35:
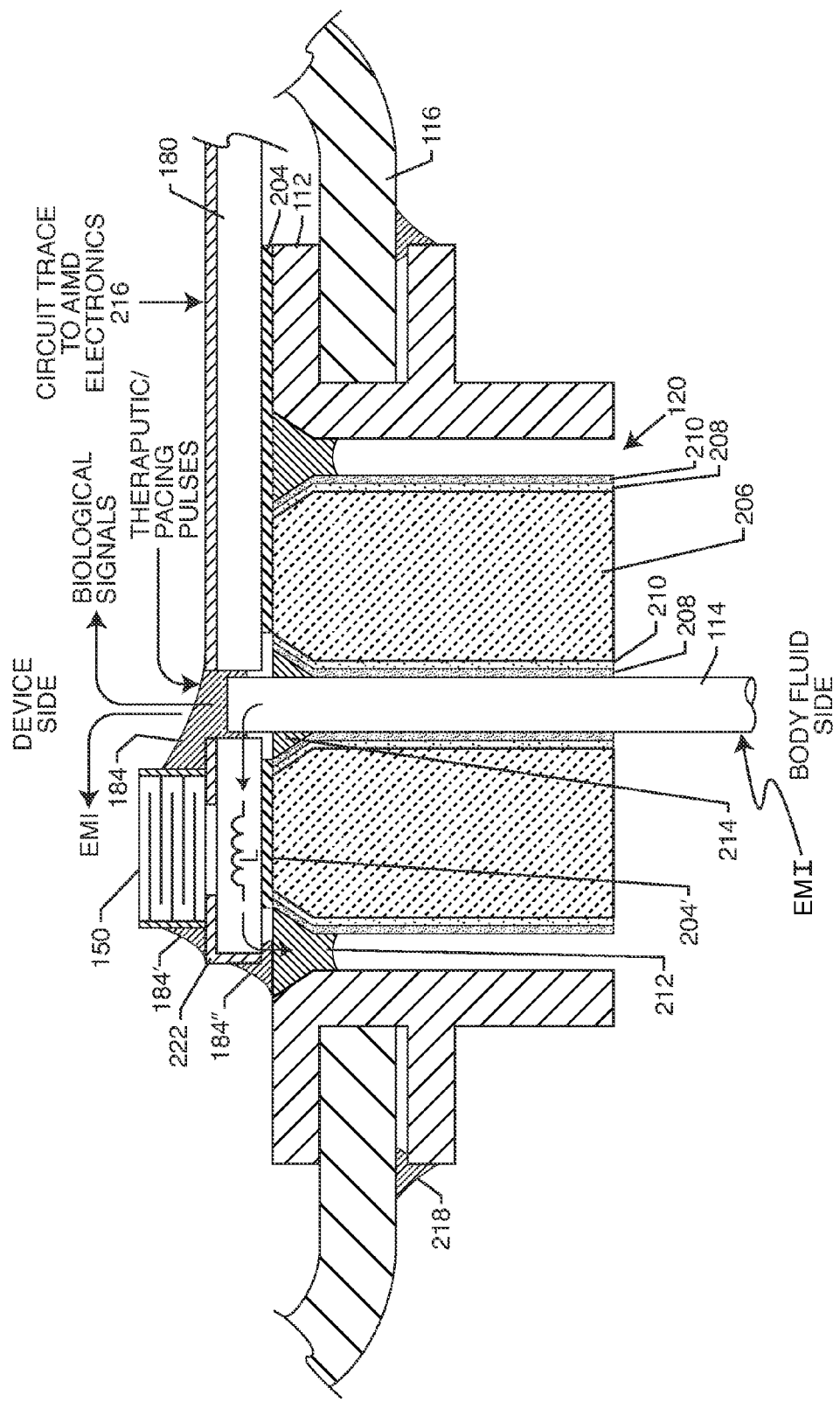
FIG. 35 illustrates a cross-sectional view of a hermetic terminal subassembly of the present invention.

FIG. 35 illustrates a cross-sectional view of a hermetic terminal subassembly 120 with a ferrule 112 onto which a circuit board 180 has been attached. Referring to the hermetic terminal subassembly 120, a biocompatible leadwire 114 passes through the ferrule in non-conductive relation. There is an insulator structure 206 typically of alumina ceramic, glass or equivalent material. For example, when the material is of alumina ceramic, there is an adhesion layer 208 which is applied by sputtering. On top of the adhesion layer is sputtered a wetting layer 210. The purpose of the adhesion and the wetting layer is to allow a gold braze 212 to essentially flow uninhibited and then stay connected to the base material. The outside diameter gold braze 212 is formed by elevating the entire assembly with a gold braze preform to the point above the melting point of gold. At the same time, the ID gold braze 214 is formed creating a mechanical and hermetic seal between the leadwire 114 and the adhesion layer on the inside diameter of the insulator 206. The circuit board has a via hole through which the lead wire 114 protrudes. Circuit trace 216 is routed to AIMD electronics and to this via hole. There can be via hole ID metallization (not shown) or an electrical connection material 184 which connects the capacitor 150 metallization to both the via hole, the circuit trace and the lead 114. The other side of the capacitor is electrically connected 184' to the end of the circuit board 180 including metallization that goes down and across the end of the circuit board ground trace 222. There is another electrical connection 184" that connects the circuit board ground trace 222 directly to the gold braze 212. This is an extremely important feature of the present invention in that the gold braze 212 has been deliberately exposed such that the capacitor 150 can be directly attached to it or through the intermediate uses of a circuit board and circuit traces as shown. This makes for a very low resistance, oxide-free and biostable connection. Another important feature as illustrated in FIG. 35 is that the capacitor is of very low inductive design as previously described in FIG. 16. This is considered a preferred embodiment, but not essential. Importantly, the inductive loop L is extremely short thereby minimizing the parasitic inductance L as previously illustrated in FIG. 11. By eliminating the contact resistance and minimizing the inductance, one obtains the attenuation curve 176 as previously illustrated in FIG. 34. Referring once again to FIG. 35, the overall construction geometry is also very important. Lead 114 on the body fluid side, is connected to an implanted lead that has a distal electrode that is contactable to biological cells. It is well known in the art that this leadwire can act undesirably as an antenna and pick up stray electromagnetic interference signals from a patient environment. Referring back to FIG. 2, one can see that electromagnetic interference (EMI) signals are impinging on implanted leads 107 and 107'. These electromagnetic interference signals are thereby transferred along lead 114 to the device side. The device side is the space inside of the overall AIMD hermetically sealed housing 116. One does not want to create "the genie in the bottle" effect. Once high frequency EMI gets inside of an AIMD housing, it can cross-couple or reradiate over to sensitive circuits thereby causing undesirable malfunctions. Referring to FIG. 35, once the EMI starts to enter the inside of the device housing, it is immediately shunted through capacitor 150 to the gold braze and in turn to the ferrule 112. As mentioned, the gold braze forms an oxide-free connection to the titanium ferrule. The ferrule is in turn laser welded 218 to the overall electromagnetic shield housing 116 of the AIMD. This dissipates the EMI over this equipotential surface where it is dispersed as a few milliwatts of harmless heat energy. It is well known that capacitor element 150 will appear as a very high impedance or open circuit at low frequencies, such as biologic frequencies, which include pacing pulses generally in the area of 1 to 2000 kHz. Accordingly, the biologic signals or sense signals that are sensed from biologic tissues are directed along circuit trace 216 to AIMD electronics. At the same time, therapeutic/pacing pulses are also directed along circuit traces 216 and down through leadwire 114 to the distal electrode (not shown). Referring once again to FIG. 35, one can see that there is a non-conductive insulative adhesive 204 and 204' which connects circuit board 180 to the hermetic seal subassembly 120. This is important since the circuit board 180 forms a cantilever beam and could be fractured during shock and vibration or even assembly stresses. In summary, material 204 is added to provide structural strength and integrity to the overall assembly.

Figure 35A:
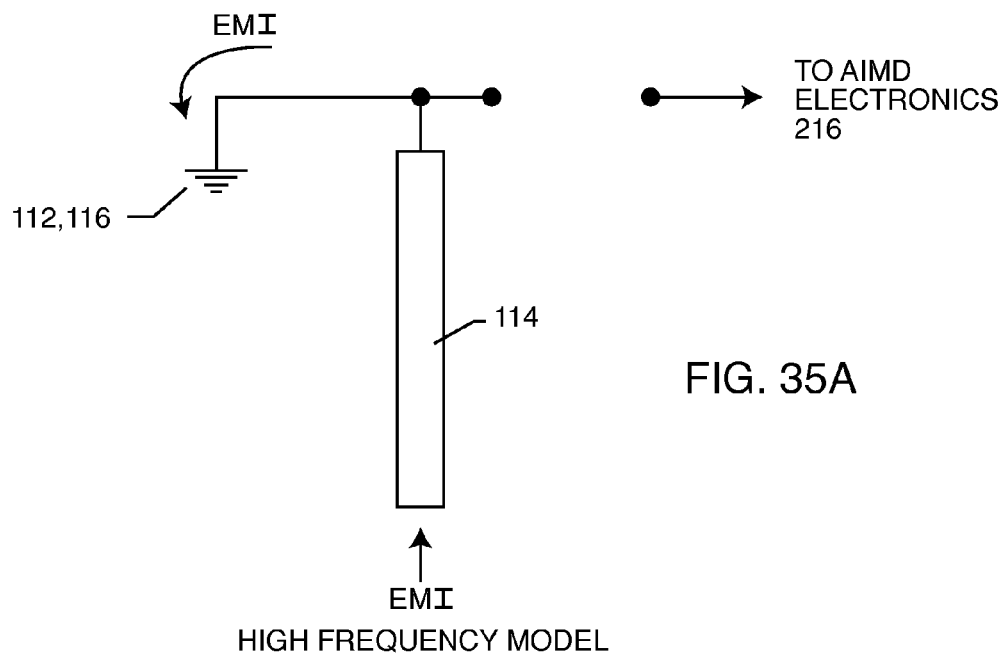
FIG. 35A illustrates a high frequency schematic of the structure of FIG. 35 wherein the capacitor tends to look like a short circuit.

FIG. 35A is a high frequency schematic model of the structure previously illustrated in FIG. 35. At high frequencies, the capacitor 150 tends to simulate a short circuit thereby shunting EMI picked up on an implanted lead 107, 114 to ground 112, 116. A ground, as defined throughout this patent, is a shielded housing 116 of an AIMD which forms an equipotential surface. In the high frequency model, an open circuit is shown in-line with the AIMD electronics. Again, this is a schematic representation simply indicating that the bulk of the high frequency energy will flow to ground and not to the AIMD electronics (even though a higher impedance electrical connection which is not shown is present there). In FIG. 35A, high frequency is defined as those frequencies at which the capacitive reactance of capacitor 150 substantially simulates a short (below 3 ohms). This generally happens at frequencies at 400 MHz and above.

Figure 35B:
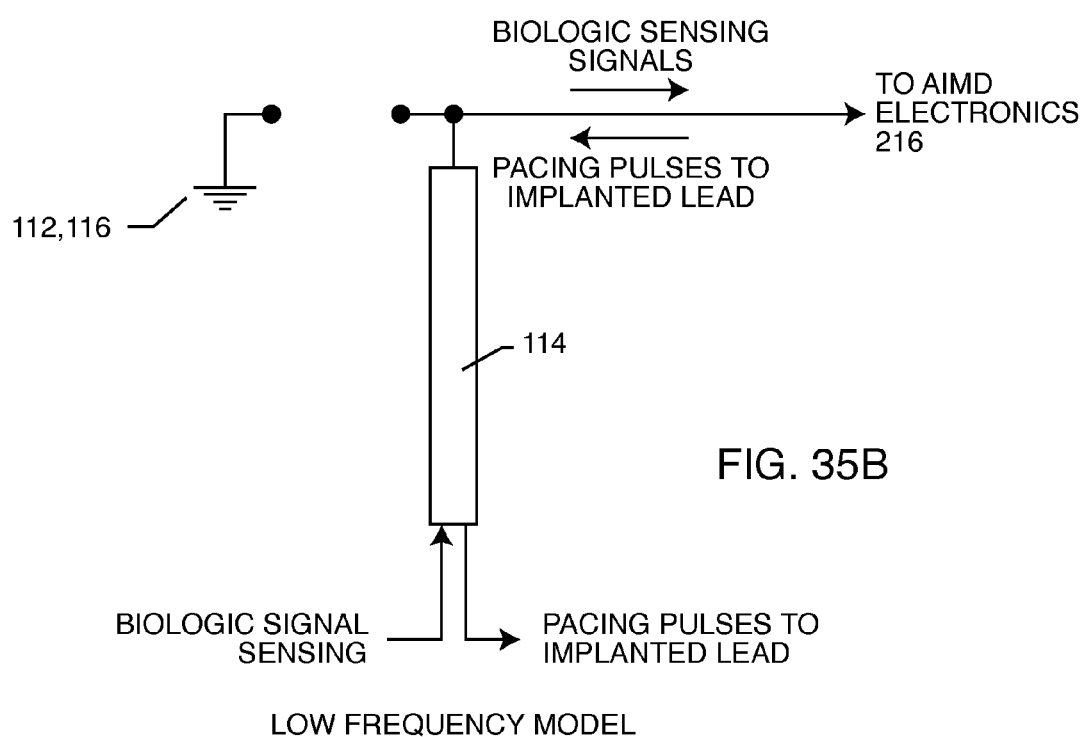
FIG. 35B illustrates a low frequency schematic of the structure of FIG. 35 wherein the capacitor tends to look like an open circuit.

FIG. 35B illustrates the low frequency model of the structure of FIG. 35. In this case, the capacitor 150 simulates an open circuit. Low frequencies, as defined for the low frequency model, include the biologic frequency range generally from zero to 2000 hertz. Referring once again to FIG. 35B, one can see that therapy/pacing pulses freely pass along the circuits from AIMD electronics to a distal electrode on an implanted lead. At the same time, the same lead (or a different lead) can detect biologic signals which the AIMD electronic circuits use such that algorithms may control or adjust therapy. An example of this would include a cardiac pacemaker application in which the cardiac pacemaker listens to not only heart beats, but also listens for dangerous cardiac arrhythmias so that appropriate therapy can be provided.

Figure 36:
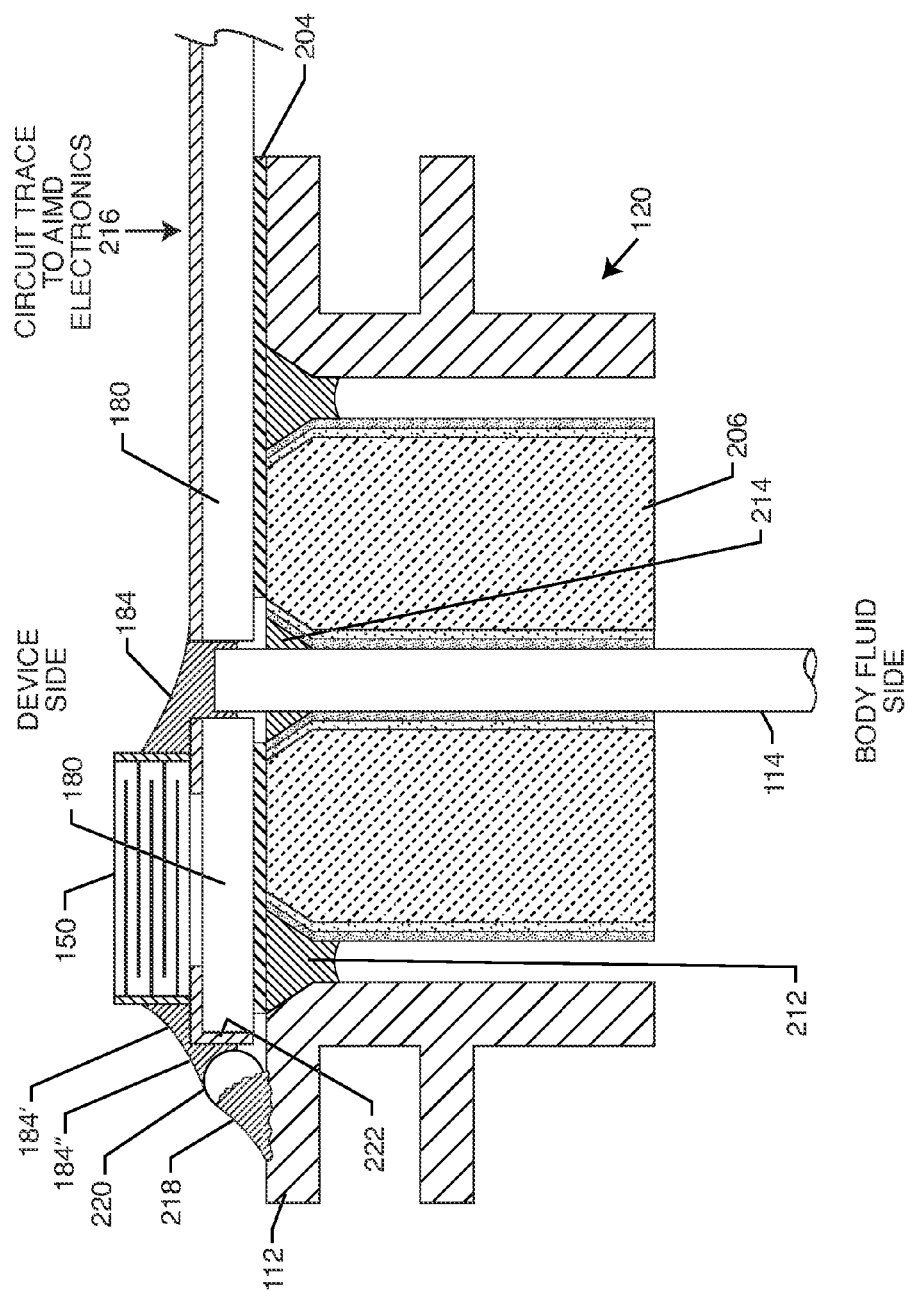
FIG. 36 is similar to FIG. 35 now using a noble metal welded to the ferrule.

FIG. 36 is very similar to FIG. 35 except that in this case the circuit board geometry 180 is longer on the left side and does not conveniently fit over the gold braze area 212. As previously mentioned, it would be highly undesirable to connect the left hand termination surface 222 of the capacitor 150 directly to the titanium ferrule surface 112. The reason for this is that titanium oxides can appear very resistive. In accordance with the present invention, there is a platinum leadwire 220 which is first laser welded 218 to the titanium ferrule 112. As previously discussed, this laser penetrates through any oxidation so that a very low impedance and highly stable metallurgical bond is formed between the platinum wire 220 and the ferrule 112. Also, as previously described, there are a number of alternate noble and other metals that can be used in place of the platinum wire 220, but provide the same functionality. For example, the round laser welded wire 220 could be gold, gold alloys, niobium, tantalum, platinum, platinum alloys such as but not limited to platinum iridium alloys, palladium, palladium alloys, silver, silver alloys, zirconium, hafnium, nitinol, Co—Cr—Ni alloys such as MP35N, Havar®, Elgiloy®, stainless steel, ZrC, ZrN, TiN, NbO, TiC and TaC, and the superalloys with nonlimiting examples such as the Hastelloys, Inconels, Monels, Waspaloys, and Renés. Referring once again to FIG. 36, one can see that there is an electrical connection material 184' which in a preferred embodiment, would actually be done in two steps. First, the circuit board would be populated 180 by robots and the capacitor 150 attached. Then, the board would be attached to the hermetic seal subassembly 120 and adhesive washers or bonds 204 would be made to mechanically attach them together. Then both electrical connections 184 and 184' would embody a secondary electrical connection connecting the active circuit trace on the right hand side 184 to lead 114 and the ground circuit trace on the left hand side, from the ground circuit trace 222 to the wire 220. In other words, electrical connection material 184' and 184 can actually be done in two operations and then flowed together as shown. Suitable materials include solders, brazes, thermal-setting conductive adhesives and the like.

Figure 37:
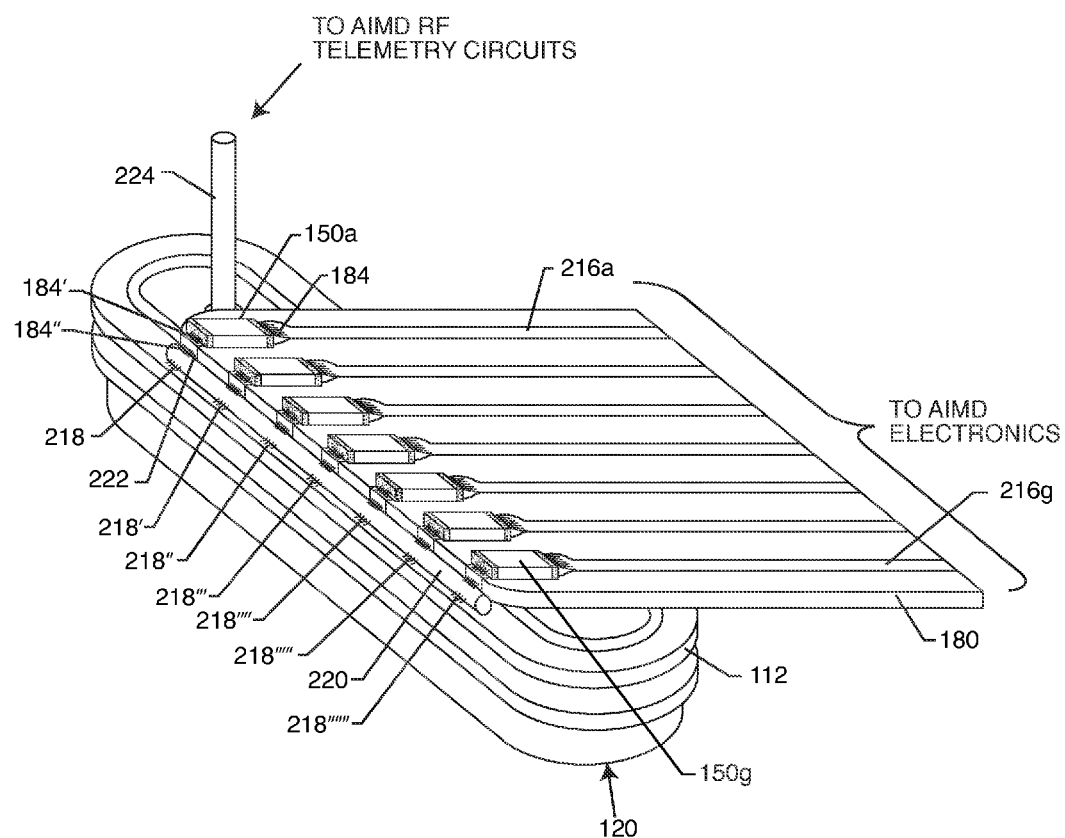
FIG. 37 is an isometric view showing one possible embodiment of the cross-section shown in FIG. 36.

FIG. 37 is an isometric view showing one possible embodiment of the cross-section shown in FIG. 36. In this case, there are seven active circuits and corresponding leadwires 114a through 114g (not shown). What is clearly shown is the ground connection to each one of the capacitors. For example, capacitor 150a has an electrical connection material 184' used to connect to the end of the circuit board ground trace 222 and there is a second electrical connection 184" which is made to the noble wire 220 as previously shown in FIG. 36. As one can see, the distances from the capacitor ground termination to the very low impedance ground connection is quite short. This has the desirable effect of keeping both the parasitic inductance of the loop very low and also the resistance of the connection very low. In this way, a maximum amount of undesirable high frequency EMI can be diverted from leadwires 114 (not shown) directly to the ferrule 112 and then in turn, to the AIMD overall electromagnetic shield housing 166 (not shown).

One can see that there is an electrical attachment material 184" to the noble leadwire 220 (such as platinum) which has been laser welded 218 directly to the ferrule 112. One can see that the laser weld is discontinuous with a significant spacing between laser weld 218 and 218" and so on. This laser weld 218 could also be continuous along the entire length of the wire 220 (not shown). Wire 220 need not be round as shown. It could be square, flat, oval or any other geometry. Referring once again to FIG. 37, one can see that there is an RF telemetry pin 224 which also connects to AIMD circuits. On the body fluid side, pin 224 connects to a telemetry pin antenna which is generally a relatively small structure located within the header block or adjacent to it. In many cases, the RF telemetry antenna is tuned to the MICS band, which is in the 402 MHz area. In this case, the antenna structure is much smaller than, for example, a cardiac lead, which could be typically around 42 to 52 cm. The entire telemetry antenna is, at best, just a few centimeters. Accordingly, it does not act as an efficient antenna at most EMI frequencies of concern. Yet still, one has to use caution when routing leadwire 224 inside of the AIMD housing just in case the patient is in the presence of a very high power emitter that does couple to the external telemetry antenna. Best practice dictates that the RF telemetry pin 224 be kept very short and that RF-to-digital circuitry be kept relatively close to this pin. The purpose for this is to avoid long circuit traces where EMI could re-radiate inside the AIMD housing and cross-couple to sensitive AIMD circuitry. Another way to accomplish the circuit board arrangement of FIG. 37 would be to have the circuit board 180 also encompass the telemetry pin 224 with a via hole and a circuit trace. In this case, there would be no bypass EMI capacitor 150. The reason for this is that the presence of the bypass capacitor would divert the desired telemetry signals to the ferrule 112 or the AIMD housing 116. By diverting them in this way, they would not be usable and detectable by AIMD telemetry transceiver circuitry. In summary, the seven-pole filter of FIG. 37 is representative of the fact that any number of active circuit traces can be employed and filtered in accordance with the present invention. Common configurations include bipolar, quad polar, octipolar and the like.

Figure 38:
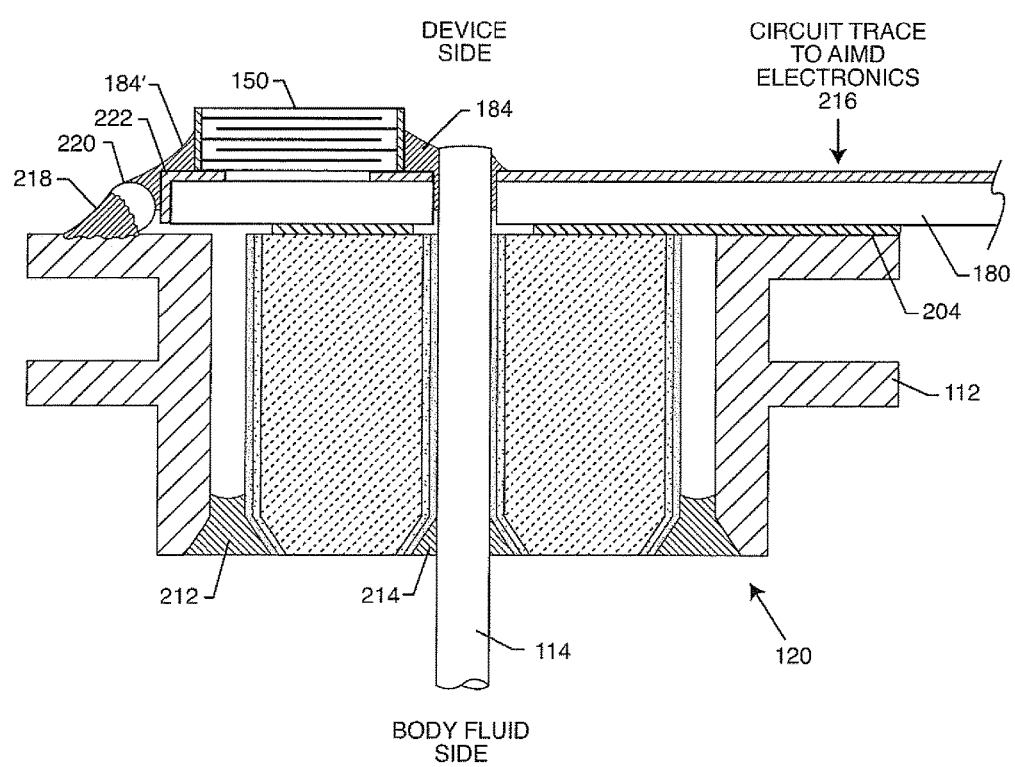
FIG. 38 is similar to FIG. 36 except that the hermetic seals are disposed on the body fluid side of the hermetic seal subassembly.

FIG. 38 is nearly identical to FIG. 36 except that the hermetic seals 212 and 214 are disposed on the body fluid side of the hermetic seal subassembly 120. By disposing the gold brazes and hermetic seals towards the body fluid side, it is literally impossible to make a ground connection from the capacitor 150 directly to the gold braze 212 as previously illustrated in FIG. 35. Accordingly, the addition of noble wire 220 becomes even more important in that a low impedance oxide-free electrical connection 184' to the ground electrode plates of MLCC capacitor 150 may be accomplished.

Figure 39:
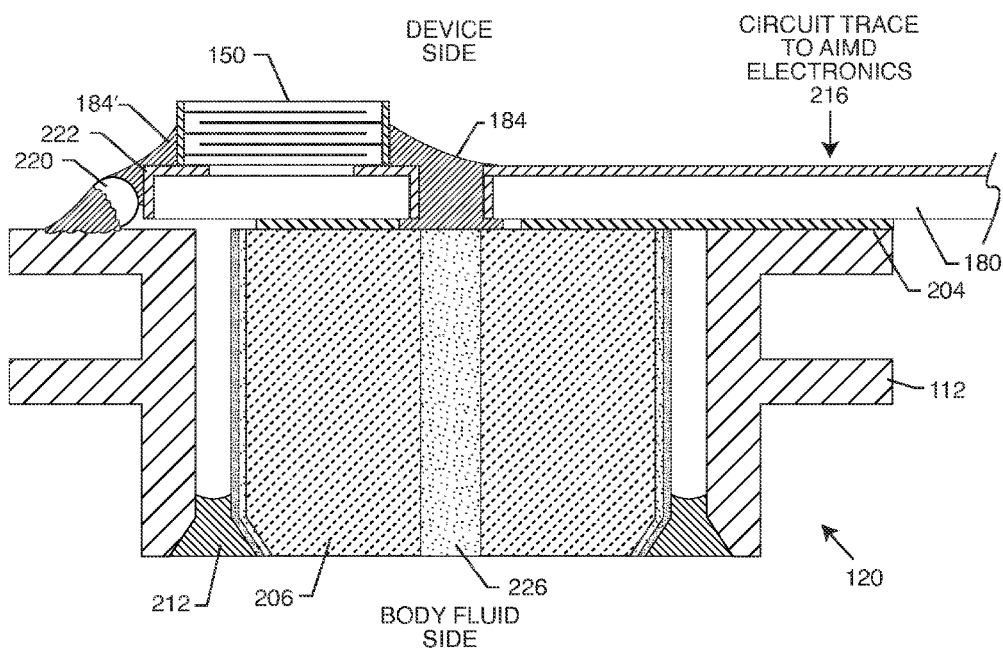
FIG. 39 is similar to FIG. 38 except that the hermetically brazed and attached leadwire has been eliminated and replaced with a solid metal-filled via.

In FIG. 39, the hermetically brazed and attached leadwire 114 of FIG. 38 has been eliminated and replaced with a solid metal-filled via 226 in accordance with U.S. Patent Publication 2013/0184797, the contents of which are incorporated herein by reference. In a preferred embodiment, as described in the 2013/0184797, the solid filled via would comprise platinum. As previously illustrated in FIG. 38, electrical connection material 184 makes contact with the capacitor's right hand side (or active electrode plate set) and directly to the circuit trace 216 and to the solid filled via material 226. On the body fluid side, a lead conductor is attached which is routed from the AIMD or an AIMD header block via a lead conductor to a distal electrode contactable to biological cells (not shown). In a preferred embodiment (not shown), the circuit board 180 would first be populated with a capacitor 150 and it would be electrically connected 184' through automated robotic techniques to the circuit board ground circuit trace 222 and to the electrical connection 184 and to active circuit trace 216. In other words, electrically connecting materials 184 and 184' can be two steps. In step one, the capacitor 150 is attached to circuit board 180 and then, in step two, the entire circuit board is mounted to the hermetic seal subassembly 120.

Figure 40:
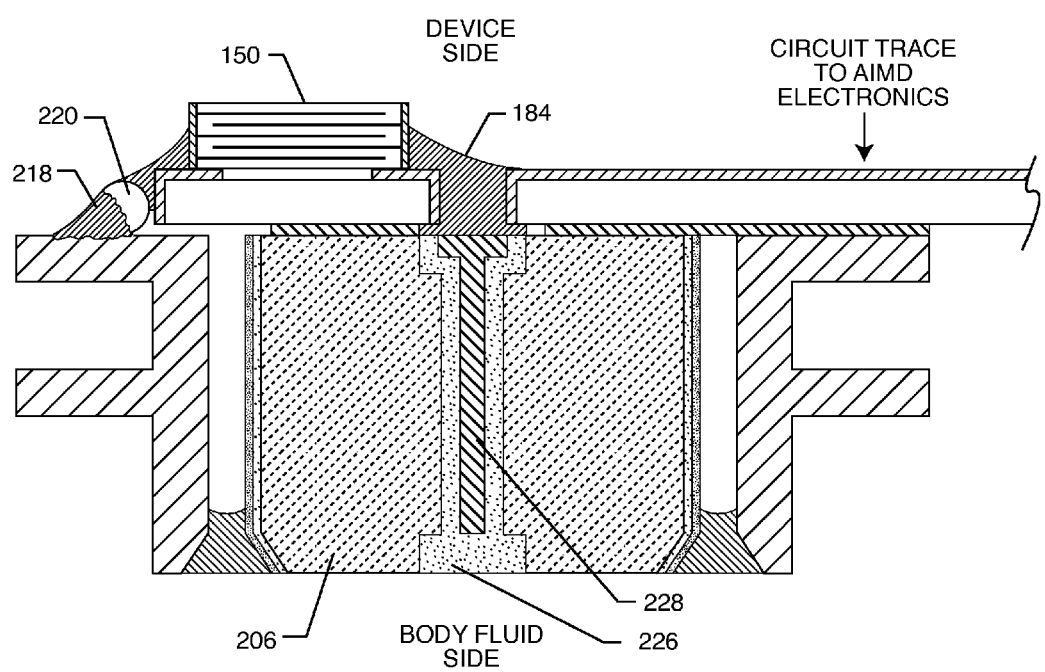
FIG. 40 is similar to FIG. 39 except the metal-filled via has a platinum or other compatible metal pin co-fired into it.

FIG. 40 is very similar to FIG. 39 except that in this case, the metal-filled via 226 has a platinum or other compatible metal pin 228 co-fired into it. This provides for a convenient wire bond pad location for attachment of electrical material or for placement of electrical attachment material 184. Importantly, pin 228 can be of very low resistivity material thereby lowering the contact resistance from the top of the solid filled via to the bottom or body fluid side. In this case, the co-fired pin 228 does not extend all the way to the body fluid side; therefore, it really does not need to be biocompatible. This means that there are a number of additional possible material choices (other than noble materials such as platinum and gold) that could be used for this pin. As a rule of thumb, when the ratio of the volume of the pin to the via paste is >1, than other material options with similar thermal expansion coefficients to platinum are preferred. Thermal coefficient of expansion may range from 4-6 micro-inches/inch ° F. Nonlimiting material examples include titanium and titanium alloys, various stainless steels such as Grades 416, 420, 436, 446 among others, and various nickel based alloys such as the Hastelloy C, Once again, as a rule of thumb, when the ratio of the volume of the pin to the via paste is >1, then material options with thermal expansion coefficients above 6 micro-inches/inch ° F. and below 4 micro-inches/inch ° F. may be used; however, in these cases considerations regarding aspect ratio of the via and of the pin become important. Nonetheless, material options in this category include tungsten, osmium, molybdenum, chromium, iridium, tantalum, niobium, rhodium, vanadium, steel and various stainless steels such as Grade 304, 316, 410, 422, 501, 502, among others, nickel and various nickel based alloys such as alloy 52, the Inconels, the Incoloys, the Monels, the Hastelloys such as Hastelloy C-276 and C-22, copper and copper alloys including cupronickel, aluminum and aluminum alloys, brasses, bronzes and the like. In all cases, material melting temperatures also need to be considered.

Figure 41:
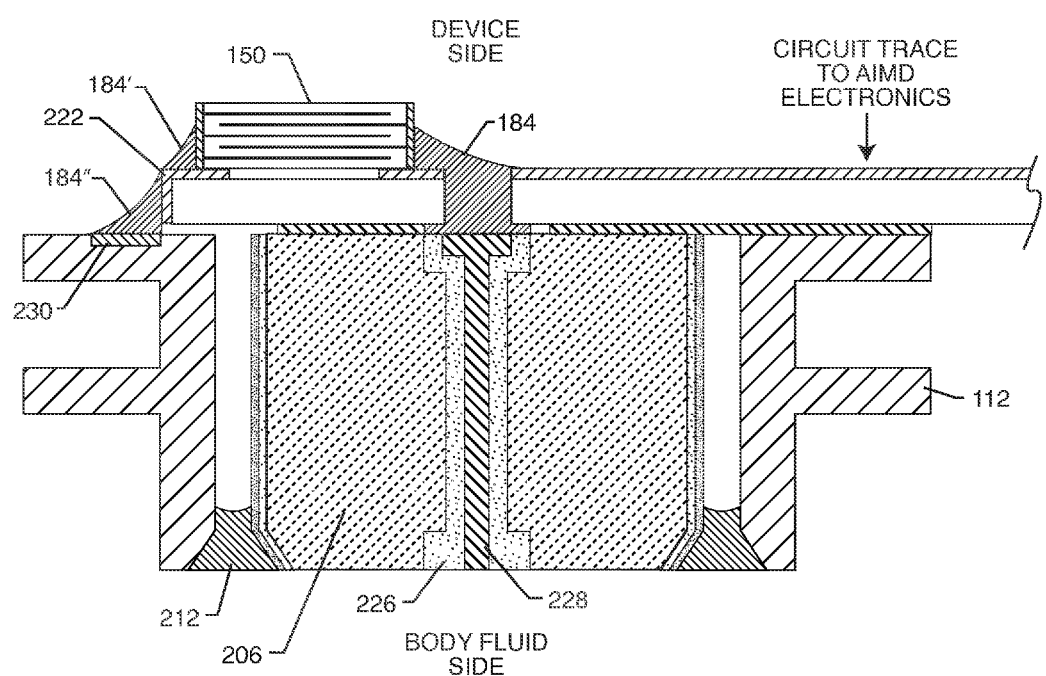
FIG. 41 is similar to FIG. 40 except the co-fired pin extends all the way from the device side to the body fluid side.

FIG. 41 is very similar to FIG. 40. The first obvious difference is that the co-fired pin 228 extends all the way from the device side to the body fluid side. It is co-fired along with the via filled material 226. As previously mentioned, material 226 would comprise a platinum fill that after firing would form a strong mechanical and hermetic bond to the alumina ceramic insulator material 206. Gold brazes 212 are still required in order to make a strong mechanical and hermetic bond between the alumina ceramic 206 and the ferrule 112. As described in FIG. 40, electrical connection material 184 makes contact with the top pin head portion of co-fired pin 228. Referring once again to FIG. 41, there is another important difference. That is, on the left or ground side of the capacitor 150, there is an electrical connection material 184' which connects the ground plates of the capacitor to circuit board ground 222. In this case, there is no wire 220 which has been laser welded directly to the ferrule 112. Instead, there is an extra gold braze pad 230 provided, which is formed at the same time as the braze connection 212 is formed. This braze pad 230 is most conveniently formed in a recess within the face of the ferrule 112, such that the gold braze preform will be held in the proper place. As previously described, the gold braze will form a mechanically robust and very low resistant oxide-free electrical connection to the titanium ferrule 112. Since gold is a noble metal, it will not oxidize over time. This means that the electrical connection 184" will form a very low resistance and inductance bond to the gold bond pad 230 and in turn, to ferrule 112.

Figure 42:
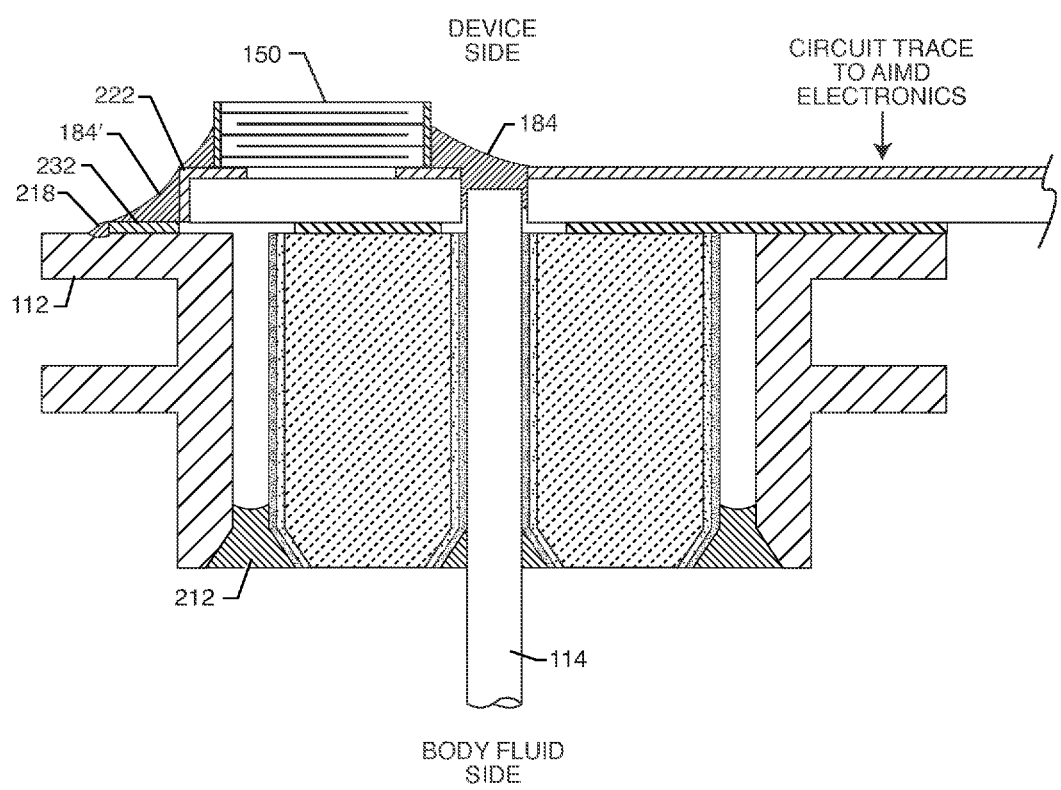
FIG. 42 is similar to FIG. 38 except that the wire has been replaced by a flat plate which has been laser welded to the ferrule.

FIG. 42 is very similar to FIG. 38 except that the wire 220 has been replaced by a flat plate 232 which has been laser welded 218 in accordance with the principles of the present invention. The flat plat 232 would, of course, be of a material that is laser welded to the titanium ferrule 112. It is also a material to which an electrical connection 184' can be made. As previously mentioned, electrical connection 184' can be a weld, can be a braze, can be a solder, can be conductive glass, can be a thermal-setting conductive material or the like.

Figure 43:
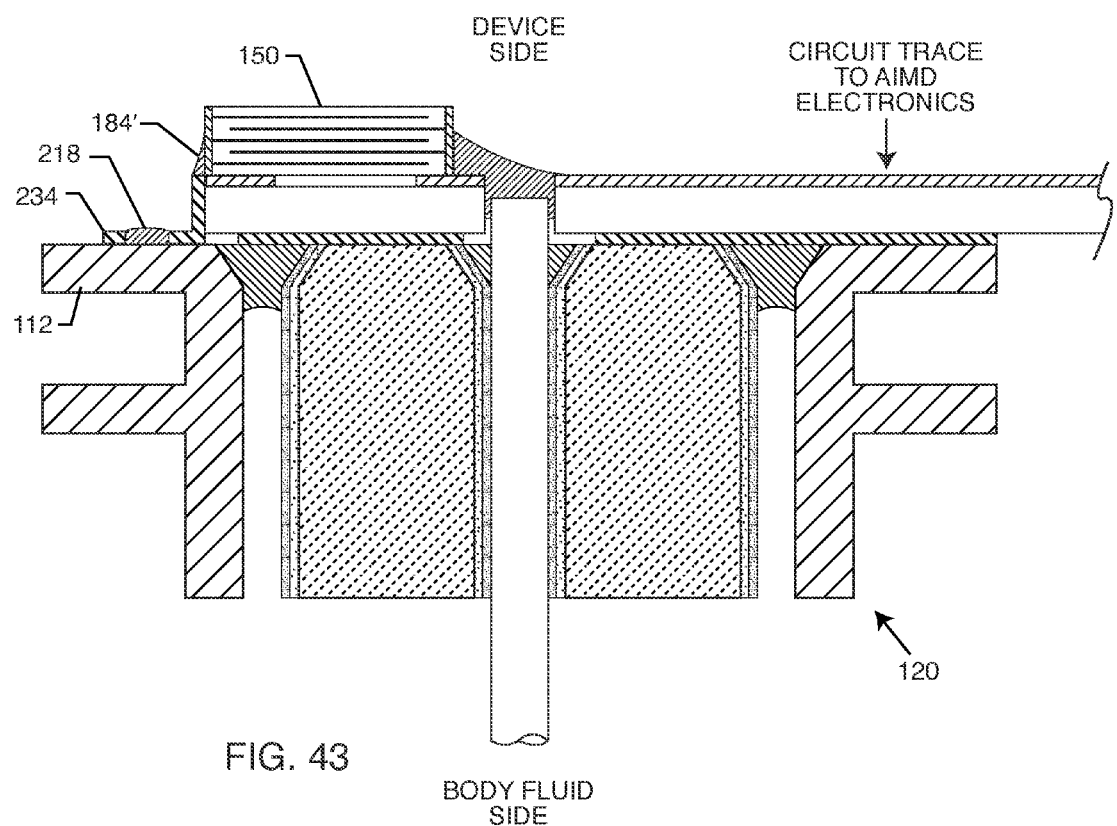
FIG. 43 is similar to FIGS. 40 and 42 except that instead of a wire or a flat place an L-shaped bracket 234 has been used.

FIG. 43 is very similar to the device described in FIGS. 40 and 42 except that instead of a wire or a flat plate, an L-shaped bracket 234 has been used. This L-shaped bracket is laser welded 218 directly to the titanium ferrule 112 of the hermetic seal subassembly 120. Then a suitable electrical connection 184' is made to the capacitor ground electrode plates.

Figure 44:
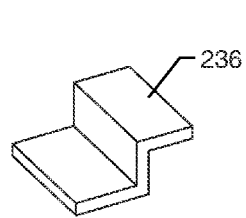
FIG. 44 illustrates a different shape bracket for use in the present invention.
Figure 45:
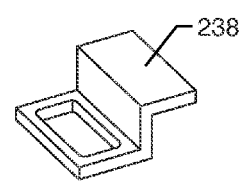
FIG. 45 illustrates a different shape bracket for use in the present invention.
Figure 46:
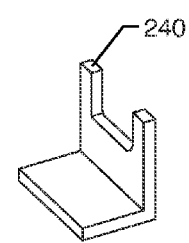
FIG. 46 illustrates a different shape bracket for use in the present invention.

FIGS. 44, 45 and 46 illustrate different shape bracket assemblies 236, 238 and 240 that can all be laser welded directly to ferrule 112 and then in turn, using an electrical connection material 184', can be connected directly to the capacitor left hand metallization and, in turn, to its ground electrode plates.

Figure 47:
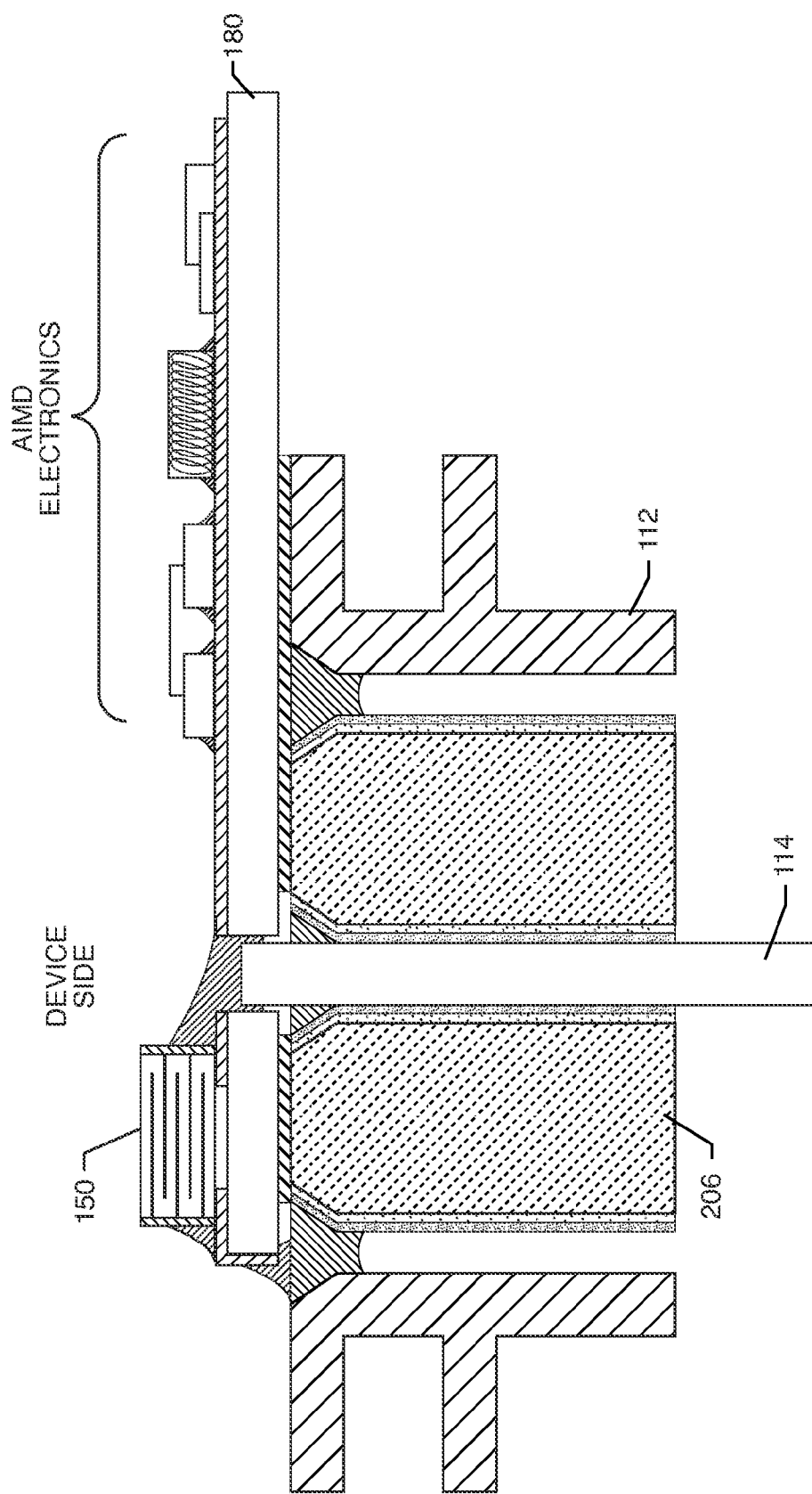
FIG. 47 is similar to FIG. 35 except that it illustrates that circuit board can be populated with a number of circuit traces and various AIMD electronic components.

FIG. 47 is the same as FIG. 35 except that it illustrates that circuit board 180 can be populated with a number of circuit traces (not shown) and various AIMD electronic components, including diode arrays, telemetry circuits, microprocessors, pulse generators and the like.

Figure 48:
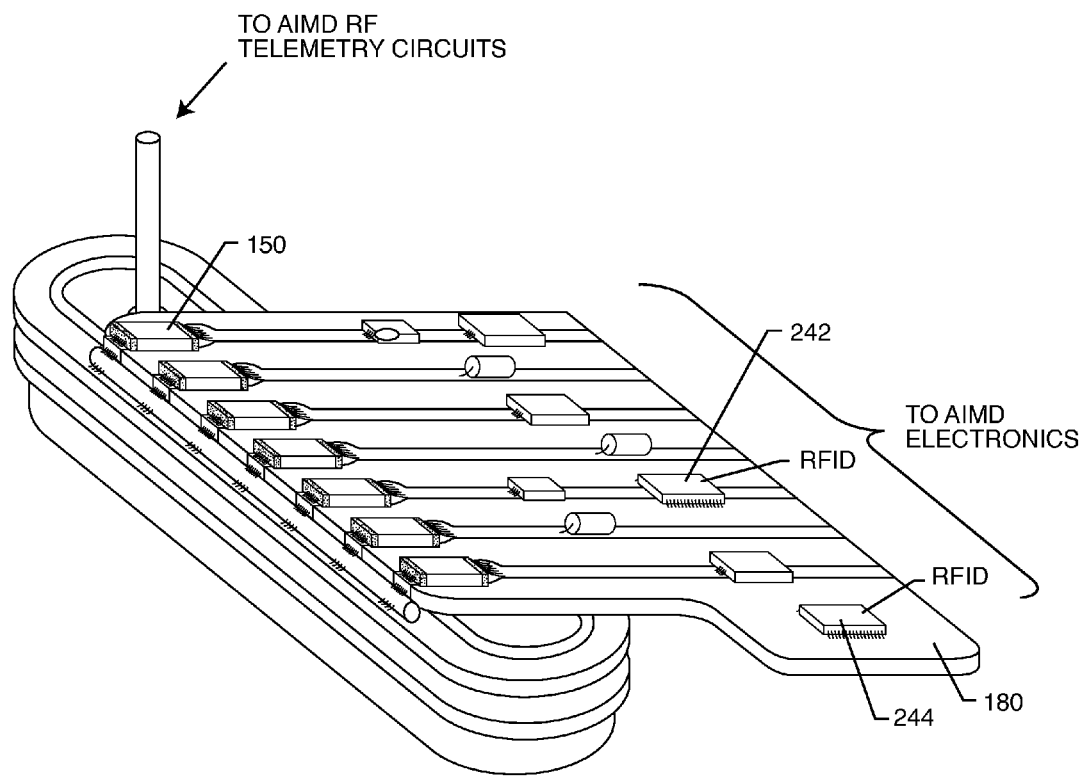
FIG. 48 is a perspective view of the structure of FIG. 47.

FIG. 48 is taken from FIG. 47 showing an isometric realization. This isometric realization is very similar to the one previously described in FIG. 37, except in this case, the circuit board has been populated with a number of other circuit components in addition to the filter capacitors 150. In particular, there are two RFID chips shown 242 and 244. RFID chip 242 is wired to circuit traces and it is possible through circuits (not shown) to connect this RFID chip to an AIMD power source, such as a primary or secondary battery. RFID chip 244 is not connected to any circuit trace and is therefore known as a passive RFID tag. It would have an antenna, a charged storage capacitor and a microcircuit (all not shown) which would pick up energy from an external RFID reader, and which would temporarily power up so that it can emit a signal and send a telemetry signal. In both cases, the RFID chips 242 and 244 could be used to rapidly identify the manufacturer's model number, serial number, make and model number of implanted leads and other important information, such as MRI compatibility of the implanted system. With informed patient consent, the RFID chip could also include information about the patient, which would be very useful at the time, for example, of entrance to a hospital emergency room to enable rapid identification of the type of medical implant. Rapidly identifying the type of medical implant can be critical in a life-threatening situation so that a proper AIMD programmer could be located, for example, to reprogram a pacemaker, increase its output or determine whether it has a depleted battery.

Figure 49:
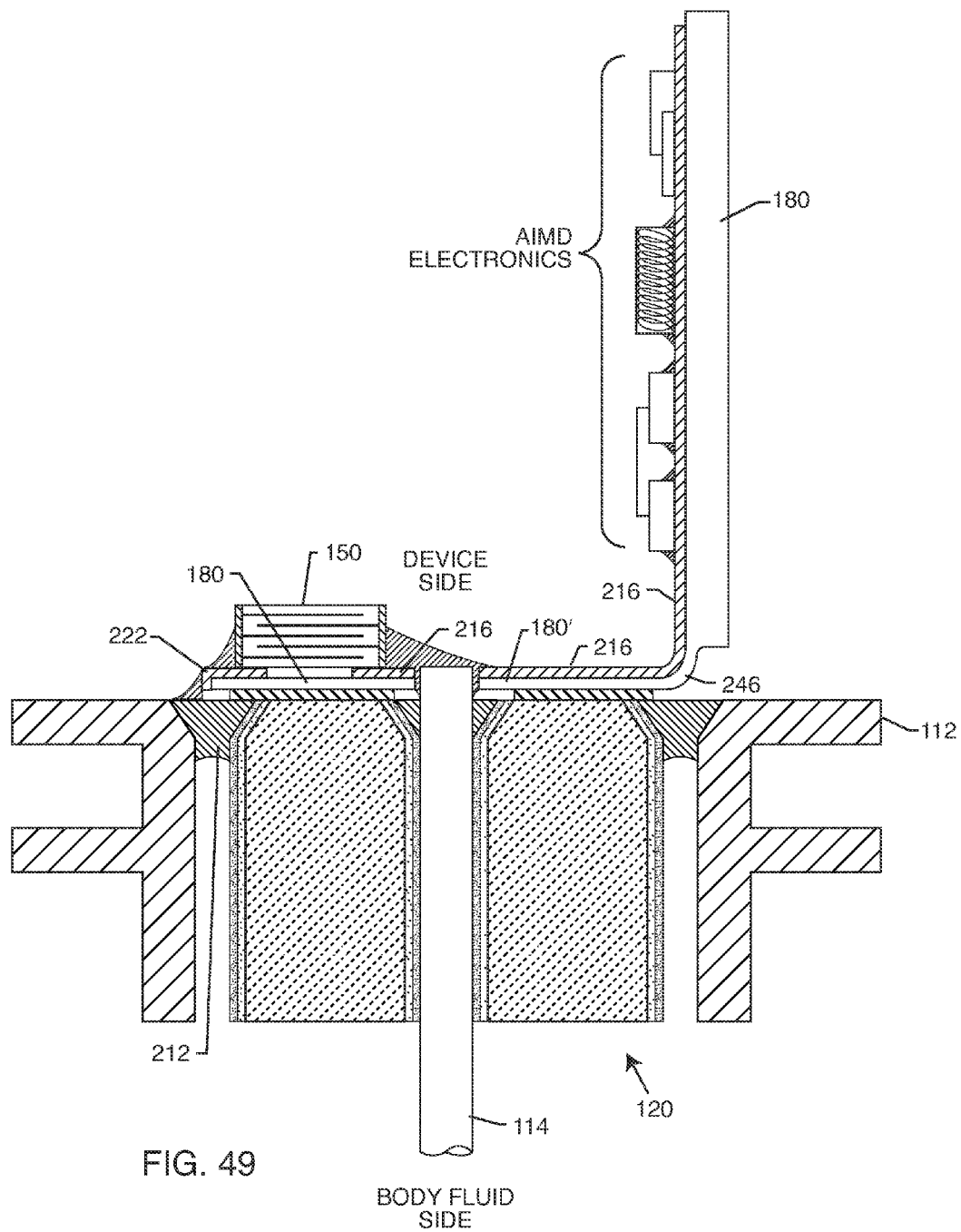
FIG. 49 illustrates that the exemplary circuit board can be rigid, flexible or a combination of both.

FIG. 49 illustrates that the exemplary circuit board 180, as previously illustrated in FIG. 48, can be rigid, flexible or a combination of both a rigid section 180 and a flexible portion 246. In accordance with the present invention, the capacitor has a low impedance oxide-free electrical connection to its ground electrode plates to gold braze material 212.

Figure 50:
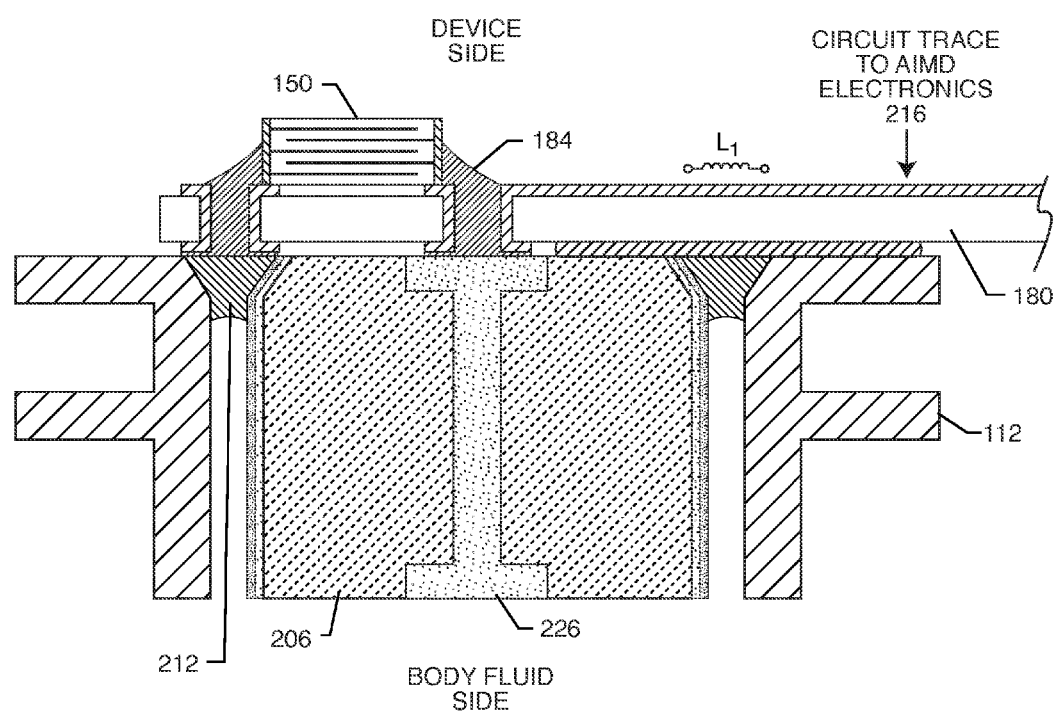
FIG. 50 is similar to FIG. 39 in that there is a solid-filled via hole contained within the alumina ceramic insulator.

FIG. 50 is very similar to FIG. 39 in that there is a solid-filled via hole 226 contained within the alumina ceramic insulator 206. As before, the outside diameter is gold brazed 212. In this case, in comparison to FIG. 39, the solid platinum (or other suitable metal) filled via 226 has a T-shaped wire bond pad in both its top and bottom. This is to increase the electrical contact area, for example, of material 184 to the MLCC chip capacitor 150 right hand termination. This nail head type configuration for the solid-filled via 226 can be on top and bottom as shown or just on the device side or just on the body fluid side. Again, one is referred to U.S. Patent Publication 2013/0184797, the contents of which are incorporated herein by reference. Patent Publication 2013/0184797 shows many different alternative solid-filled vias, all of which can be used in conjunction with the present invention.

Figure 51:
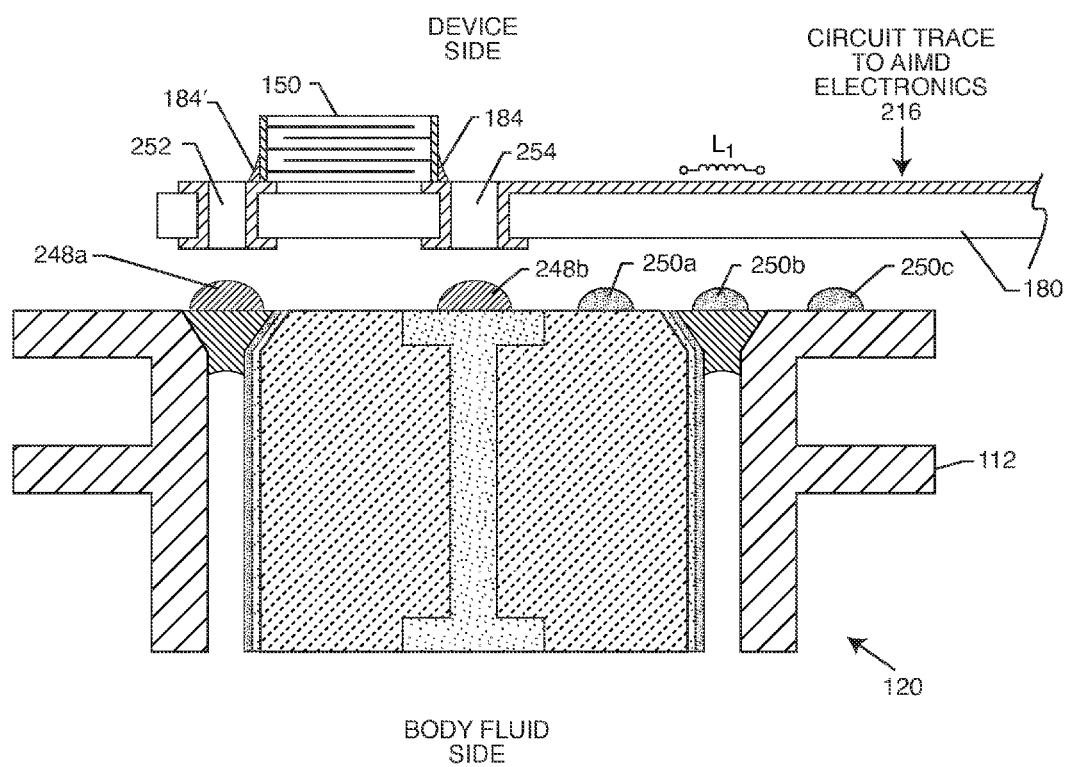
FIG. 51 is an exploded sectional view showing a production assembly of the device previously described in FIG. 50.

FIG. 51 is an exploded view showing a production assembly of the device previously described in FIG. 50. Circuit board 180 is prefabricated, including its circuit traces and via holes. Also, capacitor 150 is also preassembled along with its corresponding electrical and mechanical connections 184 and 184'. Also, a number of other components could be prefabricated, described as AIMD electronics in FIG. 49. All of these electronic components could be subjected to electrical pretesting prior to assembly onto the hermetic terminal subassembly 120. In a robotic assembly method, the ferrule hermetic terminal assembly 120 would be located into a rack or carrier and then conductive epoxy or solder bumps 248a and 248b would be dispensed. A number of non-conductive epoxy adhesive dots 250a, 250b and 250c could also be applied to provide structural rigidity and connection to circuit board 180. Then the robot places circuit board 180 in place at which time, the entire assembly is raised to an elevated temperature. This would reflow the solder or cure the conductive thermal-setting material 248 thereby making both a mechanical and electrical connection to via holes 252 and 254. This elevated temperature would also cure the non-conductive epoxy adhesive material 250a, 250b and 250c that provides a mechanical attachment to the circuit board 180. This mechanical attachment is particularly important during shock and vibration loads so that the whole assembly does not delaminate.

Figure 52:
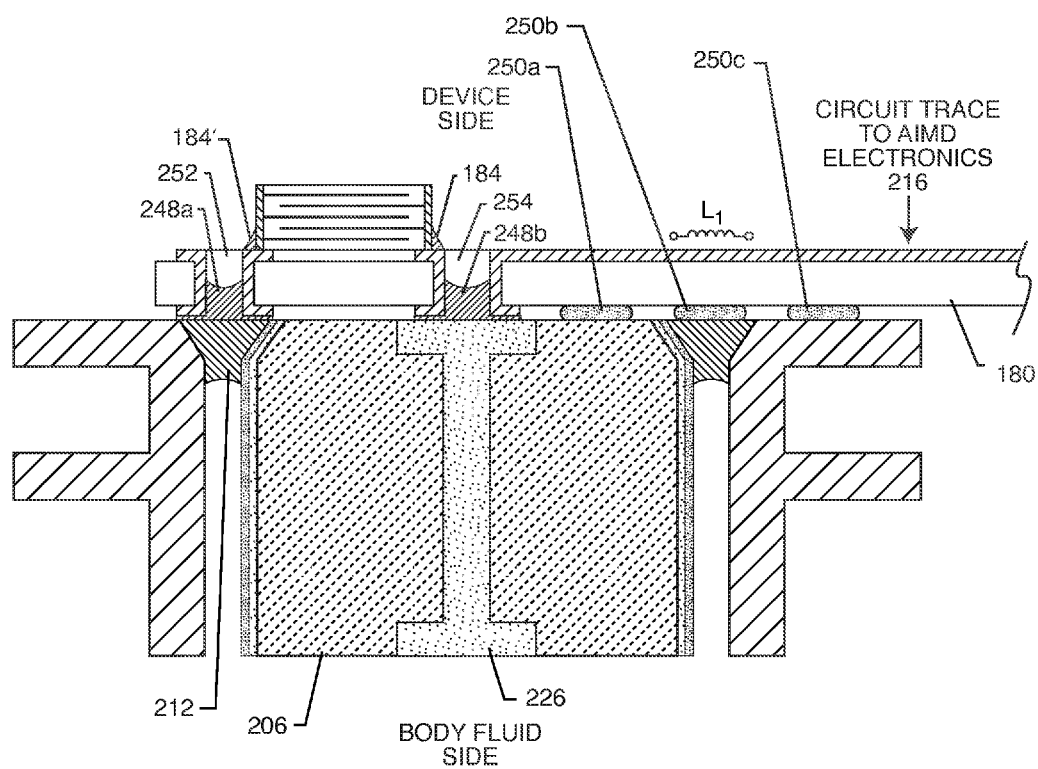
FIG. 52 is the assembly of FIG. 51 after circuit board attachment and high temperature reflow of materials showing all electrical connections and mechanical connections.

FIG. 52 is the assembly of FIG. 51 after circuit board attachment and high temperature reflow of materials showing all electrical connections and mechanical connections.

Figure 53:
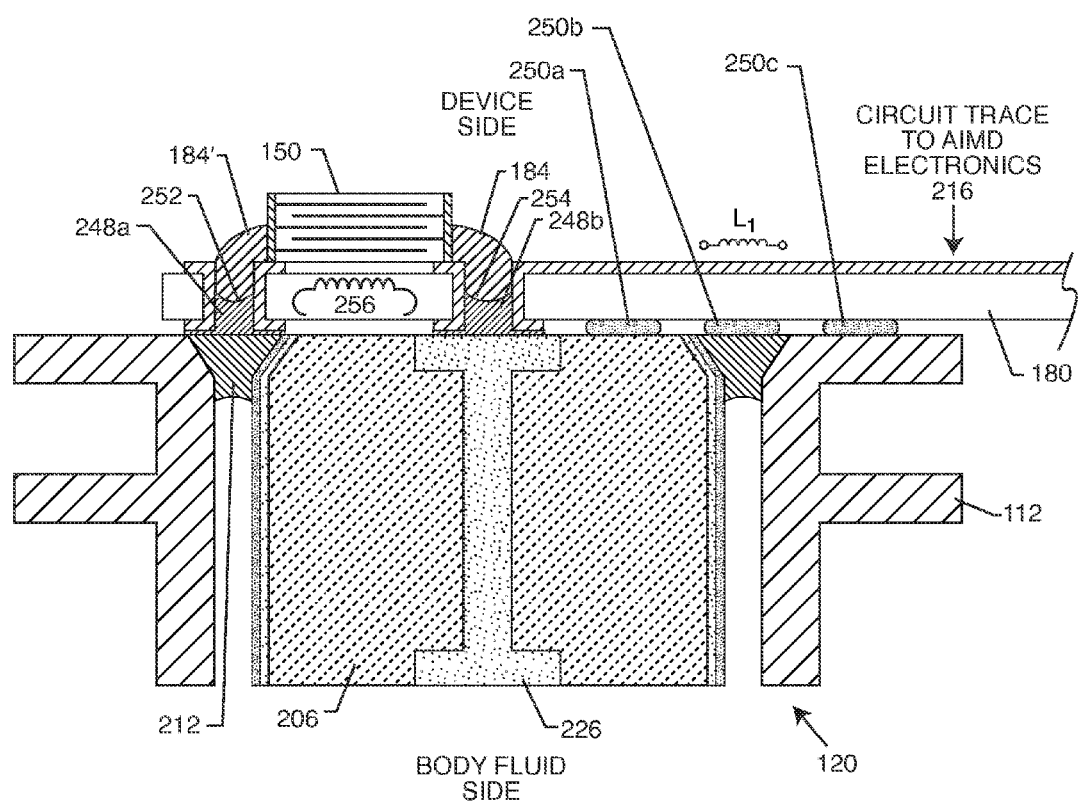
FIG. 53 is an alternative configuration of that previously described in FIGS. 51 and 52.

FIG. 53 is an alternative configuration of that previously described in FIGS. 51 and 52. In this case, the capacitor 150 has not been previously attached to the circuit board. Instead, the circuit board is laid down on the hermetic seal subassembly 120 and the electrical connections 248a and 248b are formed to the inside diameter metallization of via holes 252 and 254 (see FIG. 51). In this case then, the capacitor 150 would be subsequently added. A robot could dispense a non-adhesive epoxy dot (not shown) to hold the MLCC capacitor 150 in place. At this time, the robot could dispense a relatively higher quantity of electrically connective material 184 and 184'. This material could be a solder, a solder paste or a thermal-setting conductive adhesive or the like. By increasing the mass of the material 184 and 184', one could further reduce the resistance to the capacitor contacts and also the inductance of the loop 256 that is formed between the capacitor ground connection point to the gold braze 212, and the capacitor active electrode plate connection point to the solid-filled via 226.

Referring to FIG. 53 again, one can see that there is an inductive loop 256. In general, this inductive loop refers to the inductance all the way from the gold braze 212 through the electrical connection materials 248a and 184' and then through the capacitor 150 electrode plates and then through connection 184 through electrical contact material 248b to the solid-filled via 226. As previously stated, it is critical that the inductance of this inductive loop be kept as small as practical. Ideally, this loop inductance should be less than 10 nanohenries and in a particularly preferred embodiment, less than one nanohenry. In accordance with the present invention, the resonant frequency of the capacitor 150 and its corresponding inductive loop (no less than 400 MHz). In addition, in accordance with the present invention, the contact resistances from material 148a to the ferrule 112 should be less than 1 milliohm. In addition, the contact resistance from material 148a, which lines the inside of the circuit board 180 via hole 254, should also be 1 milliohm or less. The total resistive loop is also greatly affected by the capacitor's equivalent series resistance. For high RF power handling applications, such as when the AIMD is exposed to the intense RF fields inside of an MRI scanner, the total resistive load ideally should be less than ½ ohm and in a particularly preferred embodiment, less than 100 milliohms. In a particularly preferred embodiment, the ESR of the MLCC capacitor 150 should be less than 50 milliohms. For more information about the ESR properties of filtered capacitors for AIMD MRI applications, one is referred to U.S. Patent Publication 2012/0256704, the contents of which are incorporated herein by reference.

Figure 54:
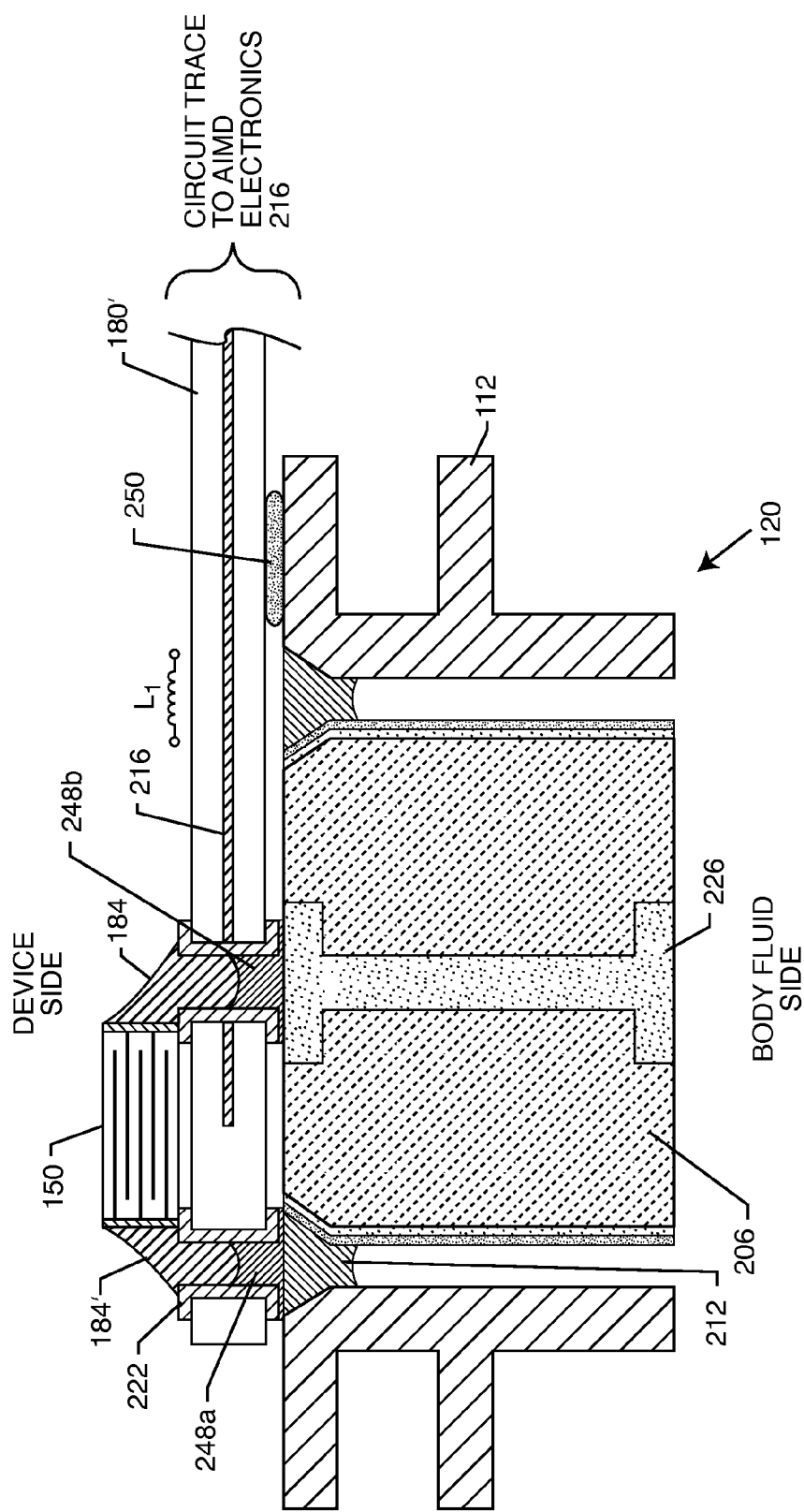
FIG. 54 is similar to FIG. 53 except now showing a multilayer circuit board.

FIG. 54 is very similar to FIG. 53 except that the circuit board 180, which has a circuit trace 216, has now been modified to be a multilayer circuit board 180' with an embedded circuit trace 216'. It is possible to add as many internal circuit traces as is needed for a particular application.

Figure 55:
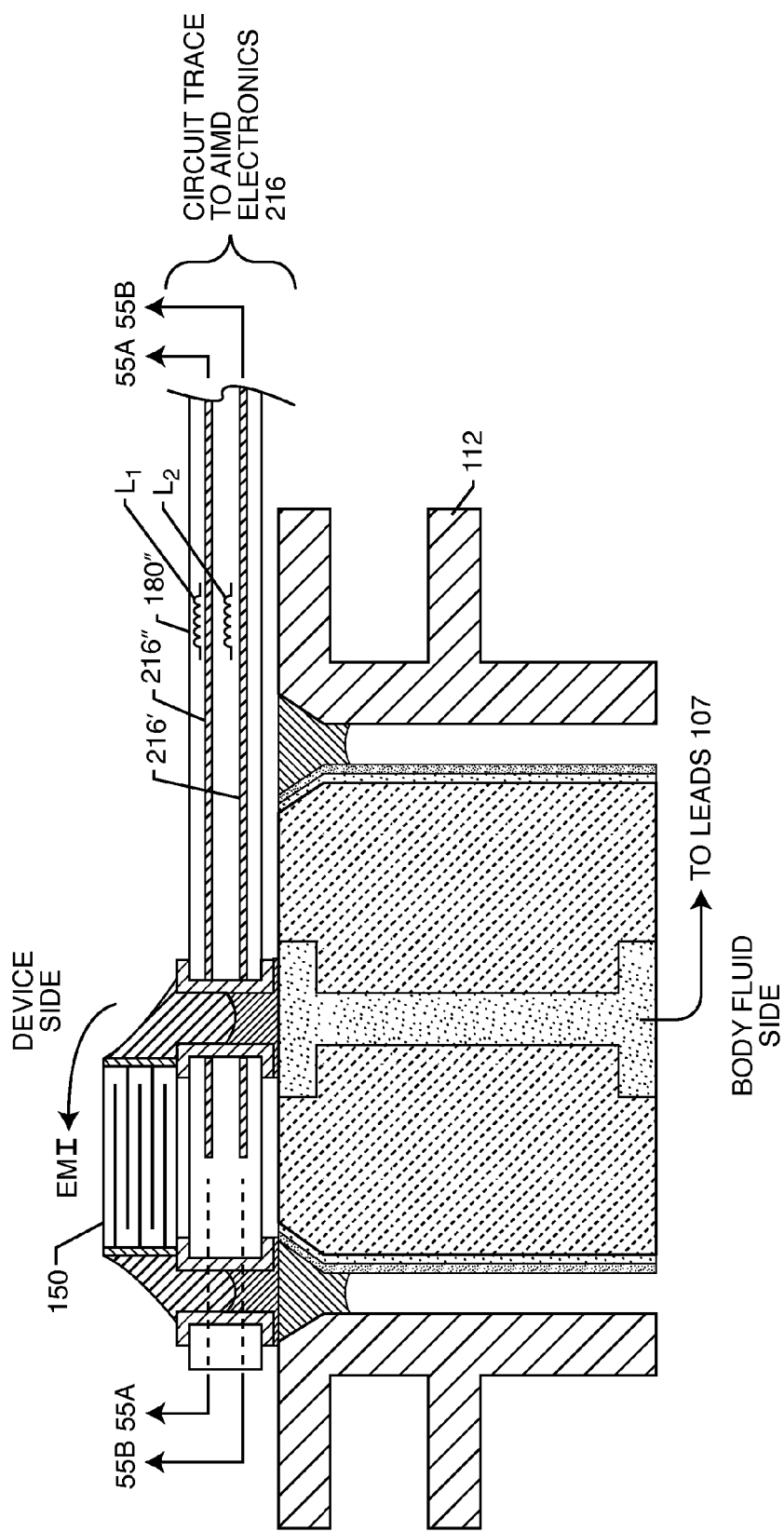
FIG. 55 is similar to FIG. 54 except there are two embedded circuit traces.

FIG. 55 is essentially the same as FIG. 54 except there are two embedded circuit traces 216' and 216" embedded in multilayer circuit board 180".

Figure 55A:
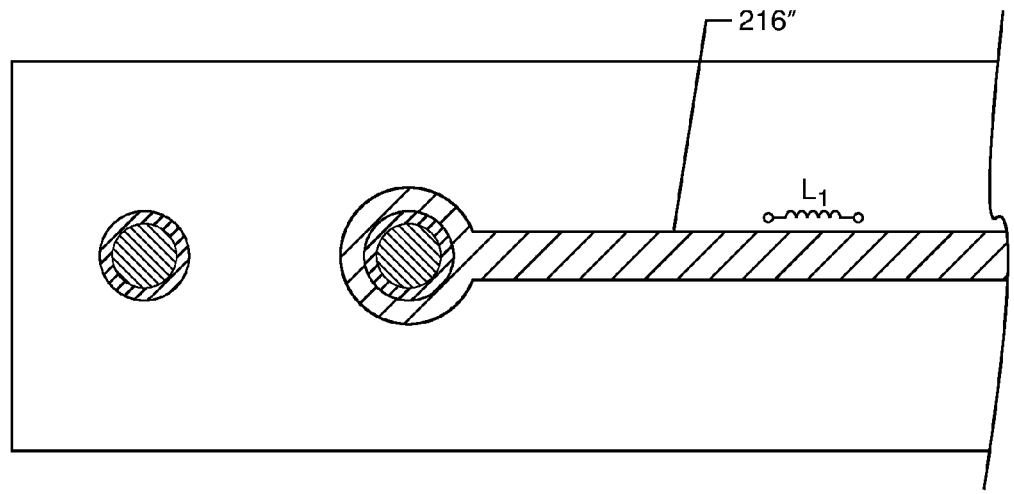
FIG. 55A is a sectional view of the structure of FIG. 55 taken along lines 55A-55A.
Figure 55B:
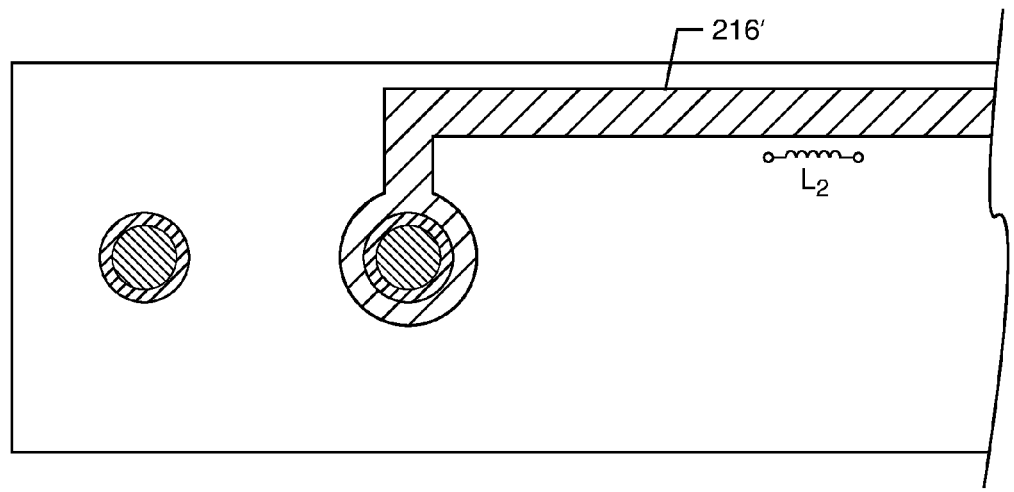
FIG. 55B is a sectional view of the structure of FIG. 55 taken along lines 55B-55B.

FIG. 55A is a sectional view taken generally from section 55A-55A from FIG. 55 showing embedded circuit trace 216". FIG. 55B is taken from section 55B-55B from FIG. 55 showing circuit trace 216'. Reference is made to multilayer shielded circuit boards of U.S. Pat. No. 7,957,806, the contents of which are incorporated by reference. Many of the circuit boards of the '806 patent are readily adaptable to the present invention. Referring once again to the circuit traces 216" and 216' illustrated in FIGS. 55A and 55B, it should be noted that the inductance of the circuit traces is no longer of any significance. In fact, it is desirable to have inductance in these circuit traces as they would tend to prevent high frequency EMI from being directed towards AIMD electronics. In other words, in the present invention, the inductance of circuit traces has been relocated to put it in a more desirable position versus the positions of the prior art. Referring once again to FIG. 55, one can see that pacing and therapeutic pulses are designed to pass through circuit traces 216' and 216". Since these are very low frequency biologic signals (generally below 2000 Hz) any inductance reactance in these circuit traces is going to be near zero. This is because inductive reactance is equal to 2PI×the frequency×the inductance. When the frequency term f is very low, the inductive reactance is trivially small. On the other hand, it is very important that the inductance of the capacitor loop 150 be kept very small so that high frequency EMI is shunted away from device AIMD electronics and directed instead to the ferrule 112 and in turn, to the AIMD shielded equipotential housing 116. Referring to inductances $L_1$ and $L_2$, these are the inherent inductances of the circuit traces 216' and 216". In the novel configuration of the present invention, these inductances are actually desirable. This is because at low frequency, the inductive reactance is essentially zero and at high frequency, the inductor will help to impede high frequency EMI currents.

FIG. 55A is taken from section 55A-55A from FIG. 55 and shows the internal circuit trace 216". FIG. 55B is taken from FIG. 55B-55B from FIG. 55 and shows circuit trace 216'. FIGS. 55A and 55B are simple representations that the internal circuit traces can be routed in any direction or any configuration.

FIG. 56A and FIG. 56B are very similar to FIGS. 55A and 55B except that inductor meanders 262 have been added. This increases the inductance $L_1$ and $L_2$ as previously described in FIG. 55 thereby adding additional protection to AIMD electronics. In other words, the series inductor adds as a high frequency RF impeder. At the same time, the chip capacitor 150 adds as a high frequency EMI diverter in that it diverts high frequency energy from the circuit traces 216 to the equipotential housing 116 of the AIMD.

FIGS. 57A and 57B are similar to FIGS. 56A and 56B except that a wheel or spiral inductor 264 has been added. In FIG. 57A, the Wheeler spiral 264 is known as a square or rectangular Wheeler spiral, whereas the Wheeler spiral 264 in FIG. 57B is known as a round Wheeler spiral. In summary, FIGS. 56A, 56B, 57A and 57B dramatically illustrate that one of the major differences of the present invention over the prior art is that the inductance of circuit traces has been relocated to actually help to increase filtering efficiency while at the same time, freely pass biological signals and therapeutic/pacing pulses. At the same time, a very low inductance and low resistance loop through the capacitor chip has been provided to efficiently divert EMI energy away from the circuit traces 216.

Referring once again to FIGS. 55A and 55B, one can see an inductance of L1 and L2. This is the inherent inductance that occurs in any straight wire or circuit trace and is dependent upon its length, width and other factors. In the present invention, having the inductance L1 and L2 in this location is actually an advantage as previously noted, in that, at high frequency, these inductances become an RF impeder.

This means that RF energy is impeded from reaching sensitive AIMD electronic where it may cause electromagnetic interference and circuit disruption.

FIGS. 56A and 56B are very similar to FIGS. 55A and 55B except that the circuit traces 216" and 216' are inductor meanders. In other words, the circuit trace has been deliberately reshaped, such that, a higher inline inductance is formed.

FIGS. 57A and 57B illustrate a square and a round Wheeler spiral inductor. A Wheeler spiral is a very efficient inductor meaning that you will have a higher inductance value within the same amount of space.

Figure 58:
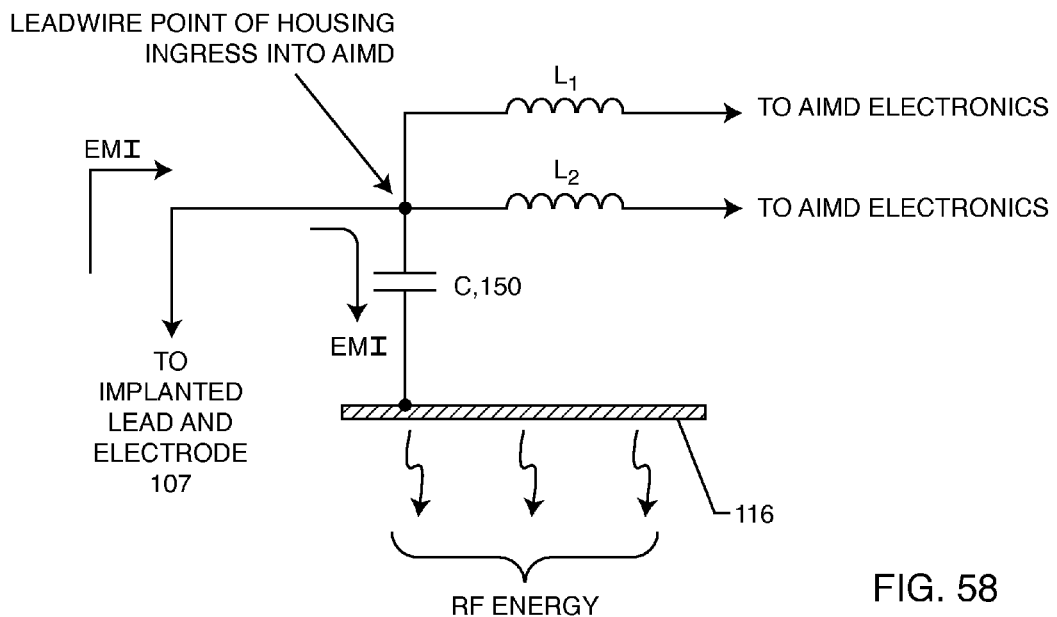
FIG. 58 is an electrical schematic of the present invention.

FIG. 58 is a schematic diagram of an EMI filter circuit board structure previously illustrated in FIG. 55. FIG. 58 shows inductances L1 and L2 as previously taught in FIGS. 55A, 55B, 56A, 56B, 57A and 57B. The location and importance of inductors L1 and L2 is best illustrated in the schematic diagram shown in FIG. 58. An implanted lead 107 (not shown) is connected on the left hand side and as previously described; it can undesirably act as an antenna and pick up stray EMI signals in the patient environment. In the present invention, this EMI is diverted by capacitor C, 150 at the point of leadwire ingress into the AIMD housing 116. The capacitor C, 150 diverts the high frequency energy to the overall electromagnetically shielded housing 116 of the AIMD. Once this energy is diverted to the housing 116, it can circulate as eddy currents, which would produce a miniscule amount of heat energy and/or RF energy may be dissipated directly to body tissues in a surrounding device pocket area. Inductors L1 and L2, particularly when they are designed to be of large value, impede or block high frequency RF energy from flowing undesirably from RFID electronics. In the art, this is known as an L-section filter. This is because the orientation of the capacitor and the inductors are similar to the letter L.

Figure 59:
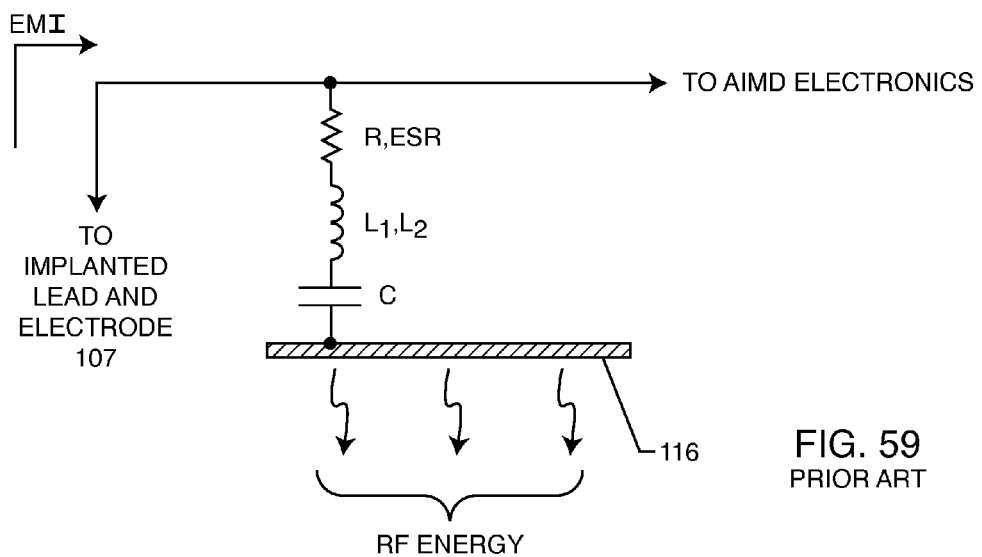
FIG. 59 is an electrical schematic of the prior art.

In contrast, FIG. 59 illustrates the prior art. In every piece of the prior art, there is either too much series resistance, R, ESR, which for example, would be due to connection to a titanium oxide, or, there would be too much inductance L1, L2 caused by circuit traces or long connections to ground. FIG. 59 illustrates in the prior art, the circuit traces are in the wrong place in that they add inductance in series with the bypass capacitor C. At high frequencies, the inductive reactance then acts as an impeder in the wrong place. Referring once again to FIG. 59, the amount of RF energy dissipated into or out of the AIMD housing 116 would be significantly diminished as compared to the present invention, as illustrated in FIG. 58.

Figure 60:
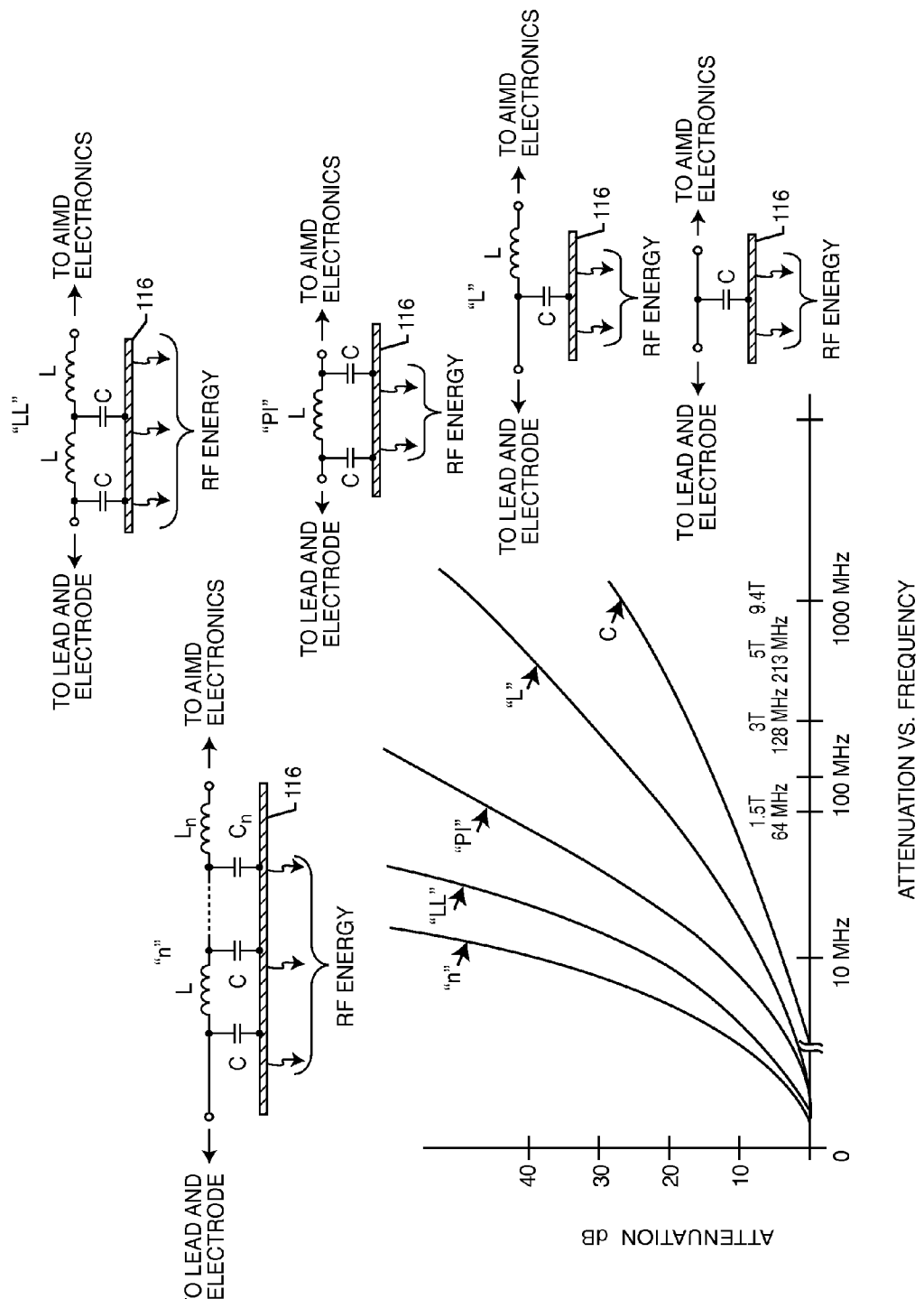
FIG. 60 is a graph of various broadband low pass filters of the present invention.

FIG. 60 illustrates a family of attenuation versus frequency curves for various types of broadband low pass filters. A single element capacitor C, 150 as previously illustrated in FIG. 58 also acts as a single element broadband low pass filter. The attenuation curve C is illustrated in FIG. 60 for this single element capacitor. When one adds a significant inductance, one forms an L-section filter which is illustrated as the "L" curve shown in FIG. 60. One can also add additional components to the present invention (not physically shown) to create a PI circuit, an LL, or "n"-element broadband low pass filter. In other words, any number of additional inductances and capacitances can be added to the present invention to further improve broadband filter performance.

Figure 61:
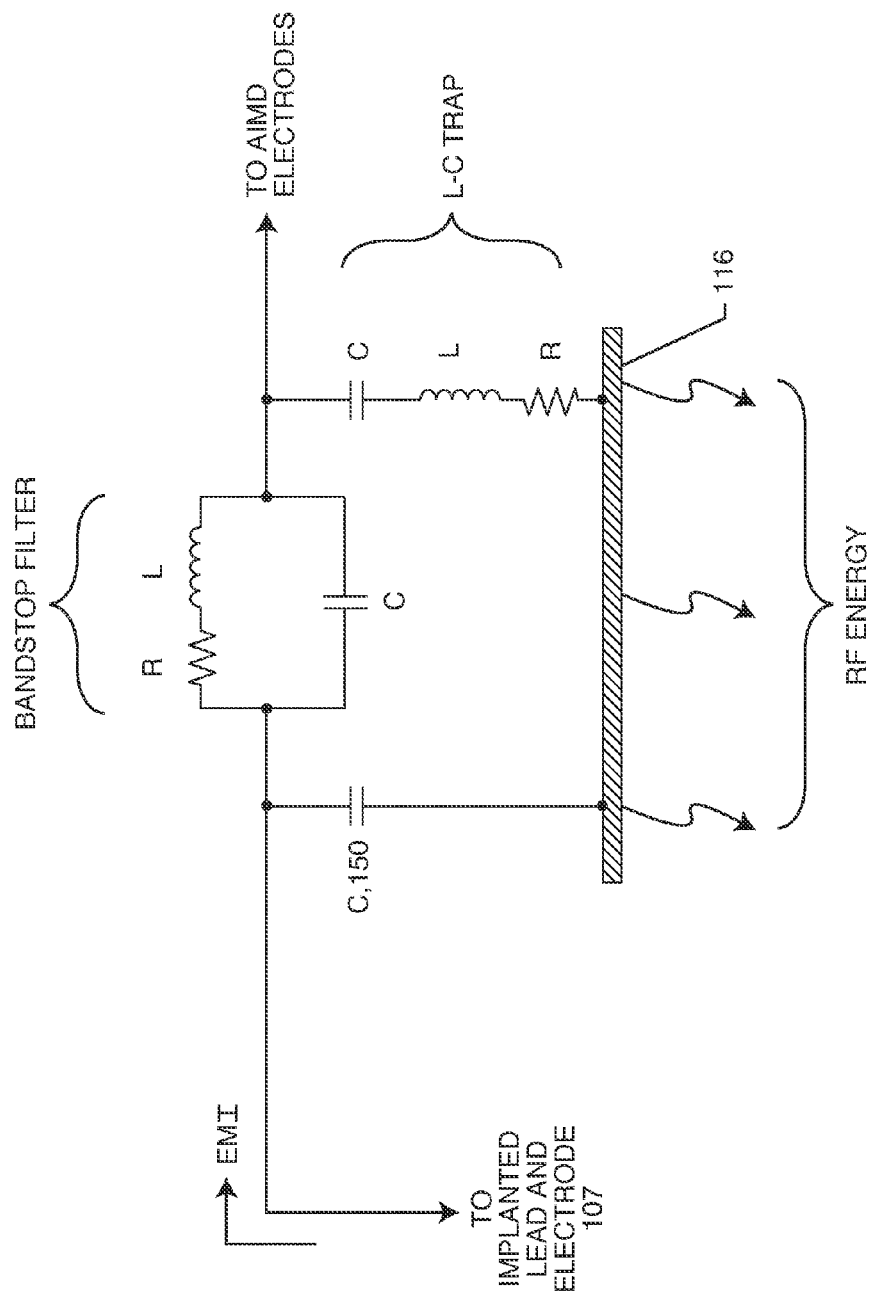
FIG. 61 is an electrical schematic of an alternative embodiment of the present invention.

FIG. 61 is very similar to FIGS. 58 and 59 and illustrates a multi-stage input filter for the AIMD. All the components shown in FIG. 61 are mounted on the circuit board of the present invention. In accordance with the present invention, the circuit board attachment provides a very low inductance and very low resistance attachment to ground, which is the overall AIMD housing 116. This ground may be through an intermediate titanium ferrule or directly to the AIMD housing 116. Referring once again to FIG. 61, we can see that there is a chip capacitor C, 150 which acts as a single element low pass filter. In series with that is a bandstop filter consisting of an inductance L in parallel with capacitance C. A resistance is shown for the inductor, which is a parasitic resistance of its windings. There is also a resistance (not shown) for the capacitor. The values of inductance and capacitance are selected such that the bandstop filter becomes resonant at MRI RF-pulsed frequency. In this case, the bandstop filter will present a very high impedance to the MRI RF-pulsed frequency thereby preventing it from reaching sensitive AIMD electronics where it could cause electromagnetic interference. There is an optional L-C trap also shown, which could be used in combination with the chip capacitor C, 150 and the bandstop filter. The L-C trap consists of a capacitor in series with a resistance between the implanted lead circuit and the AIMD housing as an energy dissipating surface 116. The L-C trap is also designed to be resonant at the same MRI RF-pulsed frequency. At resonance, the L-C trap will tend to look like a short circuit. It will not be a perfect short circuit because there will always be some resistance R associated with the inductor and the capacitor. Referring once again to the bandstop filter and the L-C trap filter of FIG. 61, controlling the amount of resistance is important so one controls the Q of the resonant filter and accordingly, its 3 dB bandwidth. Not all labeled MRI scanners are the same. In other words, a scanner that is labeled at 1.5 Tesla may not be exactly 1.5 Tesla due to variations in the cryogenic magnet used to create the main static field. Variations of >0.5 MHz between various scanners have been noted. In addition, there is a gradient field produced by an MRI machine which grades the main static field. The Larmor Equation states that the RF-pulsed field is equal to 42.56×the static magnetic field measured in Teslas. This is for a hydrogen scanner. This means that there is a different RF frequency depending upon the slice of tissue being imaged. This also requires that the 3 dB bandwidth be broad enough to capture the graded fields as well as the variation due to change and differences in manufacturing tolerances from one manufacturer or even from one machine to another. Accordingly, a 3 dB bandwidth of >128 kHz is absolutely required, but in a particularly preferred embodiment, the 3 dB bandwidth would be >0.5 MHz.

Referring now to U.S. Pat. No. 7,957,806, entitled SHIELDED THREE-TERMINAL FLAT-THROUGH EMI/ENERGY DISSIPATING FILTER and U.S. Pat. No. 8,195,295, entitled SHIELDED THREE-TERMINAL FLAT-THROUGH EMI/ENERGY DISSIPATING FILTER, the contents of both of which are herein incorporated by reference. A major difference between the present invention and the '806 and '295 patents is that the circuit traces within the '806 and '295 patents are shielded between parallel plates that form a flat-through capacitor. The reason that is not required in the present invention is the very low resistance and very low connection that is formed right at the point of lead wire ingress and egress by capacitor C, 150. An important feature of the present invention is that the capacitor C, 150 is located in such a way at or near the point of leadwire ingress into the device housing, where, due to the present design geometries and attachments, it has an insignificant amount of series resistance and inductance in series with the capacitor. This is in marked contrast to the prior art as shown in FIG. 59 where there is either a significant amount of resistance or a significant amount of inductance or both.

Although several embodiments have been described in detail for purposes of illustration, various modifications may be made to each without departing from the scope and spirit of the invention. Accordingly, the invention is not to be limited, except as by the appended claims.

What is claimed is:

1. A hermetically sealed feedthrough filter assembly for an implantable medical device, the feedthrough filter assembly comprising:
   a) a ferrule comprising an electrically conductive material defining a ferrule opening, wherein the ferrule is configured to be attachable to an opening in a housing of an active implantable medical device;
   b) an insulator at least partially residing in the ferrule opening where a first hermetic seal connects the insulator to the ferrule, wherein the insulator extends to spaced apart insulator first and second sides with an insulator via hole extending through the insulator to the insulator first and second sides;
   c) an electronic circuit board comprising an active circuit trace and a ground circuit trace, wherein the active circuit trace extends from an active circuit trace first portion to an active circuit trace second portion, and the ground circuit trace extends from a ground circuit trace first portion to a ground circuit trace second portion, and wherein the circuit board has at least one circuit board active via hole extending therethrough;
   d) a conductor extending to a conductor first portion and a conductor second portion, wherein the conductor is disposed through the insulator via hole where a second hermetic seal connects the conductor to the insulator so that the conductor is in a non-electrically conductive relation with the ferrule, and wherein the conductor first portion resides in the circuit board active via hole and the conductor second portion is electrically connectable to an implantable lead having an electrode configured for contact with body tissue;
   e) a two-terminal chip capacitor comprising at least one active electrode plate interleaved within a capacitor dielectric with at least one ground electrode plate, wherein an active metallization is electrically connected to the at least one active electrode plate and a ground metallization is electrically connected to the at least one ground electrode plate of the two-terminal chip capacitor;
   f) a first electrical connection electrically connecting the active metallization of the two-terminal chip capacitor to both:
      A) the active circuit trace first portion; and
      B) the conductor first portion residing in or adjacent to the circuit board active via hole,
      C) wherein the active circuit trace second portion is electrically connectable to electronic circuits for an implantable medical device; and
   g) a second electrical connection electrically connecting the ground metallization of the two-terminal chip capacitor to both:
      A) the ground circuit trace first portion; and
      B) the ground circuit trace second portion to the first hermetic seal contacting the ferrule.

2. The feedthrough filter assembly of claim 1, wherein at least one of the first and second electrical connections comprise a noble metal structure.

3. The feedthrough filter assembly of claim 1, wherein at least one of the first and second electrical connections comprise a gold braze.

4. The feedthrough filter assembly of claim 1, wherein the conductor first portion extends into, but not completely through the circuit board active via hole.

5. The feedthrough filter assembly of claim 1, wherein the second electrical connection comprises a solder contacting the first hermetic seal and an electrical connection material connecting the solder to the ground metallization of the two-terminal chip capacitor.

6. The feedthrough filter assembly of claim 1, wherein a ground impedance loop extends from the conductor through the first electrical connection to the two-terminal chip capacitor and then from the two-terminal chip capacitor to the second electrical connection to the first hermetic seal contacting the ferrule.

7. The feedthrough filter assembly of claim 6, wherein a total resistance of the ground impedance loop is greater than zero, but less than 0.5 ohms.

8. The feedthrough filter assembly of claim 6, wherein a total inductance of the ground impedance loop is greater than zero, but less than 10 nanohenries.

9. The feedthrough filter assembly of claim 1, wherein the two-terminal chip capacitor is selected from the group consisting of a monolithic ceramic chip capacitor (MLCC), a stacked film capacitor, a tantalum chip capacitor, an electrolytic chip capacitor, and a reverse geometry two-terminal chip capacitor.

10. The feedthrough filter assembly of claim 1, wherein the circuit board is at least partially supported by the insulator.

11. The feedthrough filter assembly of claim 1, wherein the conductor comprises a leadwire.

12. The feedthrough filter assembly of claim 11, wherein the leadwire comprises platinum or gold.

13. The feedthrough filter assembly of claim 1, wherein at least one of the insulator first and second sides is flush with a corresponding first and second side of the ferrule.

14. The feedthrough filter assembly of claim 1, including at least one nonconductive adhesive washer or epoxy that is disposed between one of:
   i) the circuit board and the ferrule;
   ii) the circuit board and the insulator; and
   ii) the circuit board and both the ferrule and the insulator.

15. The feedthrough filter assembly of claim 1, wherein the insulator comprises an alumina substrate comprised of at least 96% alumina.

16. The feedthrough filter assembly of claim 1, wherein the conductor first portion extends through the circuit board active via hole and the first electrical connection electrically couples to the conductor first portion extending outwardly from the circuit board active via hole.

17. The feedthrough filter assembly of claim 1, wherein the second electrical connection material electrically connects the ground circuit trace second portion to the first hermetic seal contacting the ferrule.

18. The feedthrough filter assembly of claim 1, wherein the circuit board comprises a flexible portion.

19. The feedthrough filter assembly of claim 1, wherein at least one of the first and second electrical connections comprises a ball grid array.

20. The feedthrough filter assembly of claim 1, wherein the two-terminal chip capacitor has a resonant frequency above 400 MHz.

21. The feedthrough filter assembly of claim 1, wherein the two-terminal chip capacitor has a capacitance in a range from 300 picofarads to 10,000 picofarads.

22. A hermetically sealed feedthrough filter assembly for an active implantable medical device, the feedthrough filter assembly comprising:
   a) a ferrule comprising an electrically conductive material defining a ferrule opening, wherein the ferrule is configured to be attachable to an opening in a housing of an active implantable medical device;
   b) a noble metal structure welded to the ferrule spaced from the ferrule opening;
   c) an insulator at least partially residing in the ferrule opening where a first hermetic seal connects the insulator to the ferrule, wherein the insulator extends to spaced apart insulator first and second sides with an insulator via hole extending through the insulator to the insulator first and second sides;
   d) an electronic circuit board comprising a circuit board first side and a circuit board second side, wherein the circuit board second side is located adjacent to the insulator first side, and wherein the circuit board comprises an active circuit trace and a ground circuit trace, the active circuit trace extending from an active circuit trace first portion to an active circuit trace second portion, and the ground circuit trace extending from a ground circuit trace first portion to a ground circuit trace second portion, and wherein the circuit board has at least one circuit board active via hole extending therethrough;
   e) a conductor extending to a conductor first portion and a conductor second portion, wherein the conductor is disposed through the insulator via hole where a second hermetic seal connects the conductor to the insulator so that the conductor is in a non-electrically conductive relation with the ferrule, and wherein the conductor first portion resides in the circuit board active via hole and the conductor second portion is electrically connectable to an implantable lead having an electrode configured for contact with body tissue;
   f) a two-terminal chip capacitor supported on the circuit board first side, the two-terminal chip capacitor comprising at least one active electrode plate interleaved within a capacitor dielectric with at least one ground electrode plate, wherein an active metallization is connected to the at least one active electrode plate and a ground metallization is connected to the at least one ground electrode plate of the two-terminal chip capacitor;
   g) a first electrical connection electrically and physically extending from the active metallization of the two-terminal chip capacitor to both:
      A) the active circuit trace first portion; and
      B) the conductor first portion residing in or adjacent to the circuit board active via hole,
      C) wherein the active circuit trace second portion is electrically connectable to electronic circuits for an implantable medical device; and
   h) a second electrical connection electrically and physically extending from the ground metallization of the two-terminal chip capacitor to both:
      A) the ground circuit trace first portion; and
      B) the ground circuit trace second portion to the noble metal structure welded to the ferrule spaced from the ferrule opening.

23. The feedthrough filter assembly of claim 22, wherein the conductor first portion extends into, but not completely through the circuit board active via hole.

24. The feedthrough filter assembly of claim 22, wherein the two-terminal chip capacitor has a resonant frequency above 400 MHz and a capacitance in a range from 300 picofarads to 10,000 picofarads.

25. The feedthrough filter assembly of claim 22, wherein the second electrical connection comprises a conductive material selected from a solder and a thermal-setting conductive adhesive.

26. The feedthrough filter assembly of claim 22, wherein a ground impedance loop having a total resistance that is greater than zero, but less than 0.5 ohm and a total inductance that is greater than zero, but less than 10 nanohenries extends from the conductor through the first electrical connection to the two-terminal chip capacitor and then from the two-terminal chip capacitor to the second electrical connection to the noble metal structure welded to the ferrule.

27. An implantable medical device, comprising:
   a) a hermetically sealed device housing containing device electronic circuits;
   b) a feedthrough filter assembly, comprising:
      i) a ferrule comprising an electrically conductive material defining a ferrule opening, wherein the ferrule is hermetically mounted in an opening in the device housing to thereby provide a ferrule device side inside the device housing and a ferrule body fluid side outside the device housing;
      ii) an insulator at least partially residing in the ferrule opening where a first hermetic seal connects the insulator to the ferrule, wherein the insulator has an insulator device side adjacent to the ferrule device side and an insulator body fluid side adjacent to the ferrule body fluid side, and wherein an insulator via hole extends through the insulator to the insulator device side and the insulator body fluid side;
      iii) an electronic circuit board located inside the device housing and comprising a circuit board first side and a circuit board second side, wherein the circuit board second side is adjacent to the insulator first device side, and wherein the circuit board comprises an active circuit trace and a ground circuit trace, the active circuit trace extending from an active circuit trace first portion to an active circuit trace second portion, and the ground circuit trace extending from a ground circuit trace first portion to a ground circuit trace second portion, and wherein the circuit board has at least one circuit board active via hole extending therethrough;
      iv) a conductor extending to a conductor first portion and a conductor second portion, wherein the conductor is disposed through the insulator via hole where a second hermetic seal connects the conductor to the insulator so that the conductor is in a non-electrically conductive relation with the ferrule and the device housing, and wherein the conductor first portion resides in the circuit board active via hole and the conductor second portion is electrically connectable to an implantable lead having an electrode configured for contact with body tissue;
      v) a two-terminal chip capacitor located inside the device housing, wherein the two-terminal chip capacitor comprises at least one active electrode plate interleaved within a capacitor dielectric with at least one ground electrode plate, and wherein an active metallization is electrically connected to the at least one active electrode plate and a ground metallization is electrically connected to the at least one ground electrode plate of the two-terminal chip capacitor;

vi) a first electrical connection electrically connecting the active metallization of the two-terminal chip capacitor to both:
   A) the active circuit trace first portion; and
   B) the conductor first portion residing in or adjacent to the circuit board active via hole,
   C) wherein the active circuit trace second portion is electrically connected to the device electronic circuits; and vii) a second electrical connection electrically connecting the ground metallization of the two-terminal chip capacitor to both:
   A) the ground circuit trace first portion; and
   B) either the ground circuit trace second portion and the first hermetic seal between the insulator and the ferrule or, the ground circuit trace second portion and to the ferrule hermetically mounted in the opening in the device housing, viii) wherein, with the active circuit trace being electrically connected to the device electronic circuits and the conductor second portion being electrically connected to a lead having an electrode that is in contact with body tissue, and
   A) under a low frequency EMI condition with the two-terminal chip capacitor resonating at greater than zero, but less than 400 MHz, the two-terminal chip capacitor permits passage of biological signals having frequencies that are greater than zero up to 1 kHz to pass from the conductor to the active circuit trace of the circuit board and then to the device electronic circuits, and
   B) under a high frequency EMI condition with the two-terminal chip capacitor resonating at at least 400 MHz, the two-terminal chip capacitor acts as an open circuit that does not permit biological signals having frequencies greater than zero up to 1 kHz to pass from the conductor to the active circuit trace of the circuit board and then to the device electronic circuits.

28. The implantable medical device of claim 27, wherein a ground impedance loop having a total resistance that is greater than zero, but less than 0.5 ohm and a total inductance that is greater than zero, but less than 10 nanohenries extends from the conductor through the first electrical connection to the two-terminal chip capacitor and then from the two-terminal chip capacitor to the second electrical connection and the ground circuit trace and to the first hermetic seal contacting the ferrule.

29. The implantable medical device of claim 27, wherein, under the high frequency EMI condition, the two-terminal chip capacitor resonates at over 800 MHz.

30. The implantable medical device of claim 27, wherein the circuit board resides adjacent to the insulator device side with the conductor first portion extending into, but not completely through the circuit board active via hole.

31. The feedthrough filter assembly of claim 27, wherein, under the high frequency EMI condition, the two-terminal chip capacitor resonates at over 800 MHz.

32. The feedthrough filter assembly of claim 27, wherein the two-terminal chip capacitor has a resonant frequency above 400 MHz.

33. The feedthrough filter assembly of claim 27, wherein the two-terminal chip capacitor has a capacitance in a range from 300 picofarads to 10,000 picofarads.

34. An implantable medical device, comprising:
a) a hermetically sealed device housing containing device electronic circuits;
b) a feedthrough filter assembly, comprising:
   i) a ferrule comprising an electrically conductive material defining a ferrule opening, wherein the ferrule is hermetically mounted in an opening in the device housing to thereby provide a ferrule device side inside the device housing and a ferrule body fluid side outside the device housing;
   ii) an insulator at least partially residing in the ferrule opening where a first hermetic seal connects the insulator to the ferrule, wherein the insulator has an insulator device side adjacent to the ferrule device side and an insulator body fluid side adjacent to the ferrule body fluid side, and wherein an insulator via hole extends through the insulator to the insulator device side and the insulator body fluid side, and wherein at least one of the insulator device and body fluid sides is flush with the adjacent ferrule device and body fluid side;
   iii) an electronic circuit board located inside the device housing and comprising a circuit board first side and a circuit board second side, and wherein the circuit board comprises an active circuit trace and a ground circuit trace, the active circuit trace extending from an active circuit trace first portion to an active circuit trace second portion, and the ground circuit trace extending from a ground circuit trace first portion to a ground circuit trace second portion, and wherein the circuit board has at least one circuit board active via hole extending therethrough;
   iv) a conductor extending to a conductor inside device portion and a conductor body fluid portion, wherein the conductor is disposed through the insulator via hole where a second hermetic seal connects the conductor to the insulator so that the conductor is in a non-electrically conductive relation with the ferrule and the device housing, and wherein the conductor inside device portion resides in the circuit board active via hole and the conductor body fluid portion is electrically connectable to an implantable lead having an electrode configured for contact with body tissue;
   v) a two-terminal chip capacitor located inside the device housing and supported on the circuit board first side, wherein the two-terminal chip capacitor comprises at least one active electrode plate interleaved within a capacitor dielectric with at least one ground electrode plate, and wherein an active metallization is electrically connected to the at least one active electrode plate and a ground metallization is electrically connected to the at least one ground electrode plate of the two-terminal chip capacitor;
   vi) a first electrical connection electrically connecting the active metallization of the two-terminal chip capacitor to both:
      A) the active circuit trace first portion; and
      B) the conductor inside device portion residing in or adjacent to the circuit board active via hole,
      C) wherein the active circuit trace second portion is electrically connected to the device electronic circuits; and vii) a second electrical connection electrically connecting the ground metallization of the two-terminal chip capacitor to both:
   A) the ground circuit trace first portion; and
   B) either the ground circuit trace second portion and the first hermetic seal between the insulator and the ferrule or, the ground circuit trace second portion and directly to the ferrule hermetically mounted in the opening in the device housing,
viii) wherein, with the active circuit trace being electrically connected to the device electronic circuits and the conductor body fluid portion being electrically connected to a lead having an electrode that is in contact with body tissue, and
   A) under a low frequency EMI condition with the two-terminal chip capacitor resonating at greater than zero, but less than 400 MHz, the two-terminal chip capacitor permits passage of biological signals having frequencies that are greater than zero up to 1 kHz to pass from the conductor to the active circuit trace of the circuit board and then to the device electronic circuits, and
   B) under a high frequency EMI condition with the two-terminal chip capacitor resonating at at least 400 MHz, the two-terminal chip capacitor acts as an open circuit that does not permit biological signals having frequencies greater than zero up to 1 kHz to pass from the conductor to the active circuit trace of the circuit board and then to the device electronic circuits.

35. The implantable medical device of claim 34, wherein the circuit board resides adjacent to the insulator device side with the conductor inside device portion extending into, but not completely through the circuit board active via hole.

36. The implantable medical device of claim 34, wherein the two-terminal chip capacitor has a resonant frequency above 400 MHz and a capacitance in a range from 300 picofarads to 10,000 picofarads.

37. The feedthrough filter assembly of claim 34, wherein a ground impedance loop having a total resistance that is greater than zero, but less than 0.5 ohm and a total inductance that is greater than zero, but less than 10 nanohenries extends from the conductor through the first electrical connection to the two-terminal chip capacitor and then from the two-terminal chip capacitor to the second electrical connection and the ground trace and to the first hermetic seal contacting the ferrule.

38. A hermetically sealed feedthrough filter assembly for an implantable medical device, the feedthrough filter assembly comprising:
   a) a ferrule comprising an electrically conductive material defining a ferrule opening, wherein the ferrule is configured to be attachable to an opening in a housing of an active implantable medical device;
   b) an insulator at least partially residing in the ferrule opening where a first hermetic seal connects the insulator to the ferrule, wherein the insulator extends to spaced apart insulator first and second sides with an insulator via hole extending through the insulator to the insulator first and second sides;
   c) an electronic circuit board comprising an active circuit trace and a ground circuit trace, wherein the active circuit trace extends from an active circuit trace first portion to an active circuit trace second portion, and the ground circuit trace extends from a ground circuit trace first portion to a ground circuit trace second portion, and wherein the circuit board has at least one circuit board active via hole extending therethrough;
   d) a conductor extending to a conductor first portion and a conductor second portion, wherein the conductor is disposed through the insulator via hole where a second hermetic seal connects the conductor to the insulator so that the conductor is in a non-electrically conductive relation with the ferrule, and wherein the conductor first portion resides in the circuit board active via hole and the conductor second portion is electrically connectable to an implantable lead having an electrode configured for contact with body tissue;
   e) a two-terminal chip capacitor comprising at least one active electrode plate interleaved within a capacitor dielectric with at least one ground electrode plate, wherein an active metallization is electrically connected to the at least one active electrode plate and a ground metallization is electrically connected to the at least one ground electrode plate of the two-terminal chip capacitor;
   f) a first electrical connection electrically connecting the active metallization of the two-terminal chip capacitor to both:
      A) the active circuit trace first portion; and
      B) the conductor first portion residing in or adjacent to the circuit board active via hole,
      C) wherein the active circuit trace second portion is electrically connectable to electronic circuits for an implantable medical device; and
   g) a second electrical connection electrically connecting the ground metallization of the two-terminal chip capacitor to the ground circuit trace first portion; and
   h) a third electrical connection electrically connecting the ground circuit trace second portion to the first hermetic seal between the insulator and the ferrule or directly to the ferrule.

39. The feedthrough filter assembly of claim 38, wherein the conductor first portion extends into, but not completely through the circuit board active via hole.

40. The feedthrough filter assembly of claim 38, wherein the two-terminal chip capacitor has a resonant frequency above 400 MHz and a capacitance in a range from 300 picofarads to 10,000 picofarads.

41. The feedthrough filter assembly of claim 38, wherein the second electrical connection comprises a conductive material selected from a solder and a thermal-setting conductive adhesive.

42. The feedthrough filter assembly of claim 38, wherein a ground impedance loop having a total resistance that is greater than zero, but less than 0.5 ohm and a total inductance that is greater than zero, but less than 10 nanohenries extends from the conductor through the first electrical connection to the two-terminal chip capacitor and then from the two-terminal chip capacitor to the second electrical connection to the ground circuit trace first portion and the third electrical connection from the ground circuit trace second portion to the first hermetic seal contacting the ferrule.

* * * * *